US011242540B2

(12) United States Patent
Bowen et al.

(10) Patent No.: US 11,242,540 B2
(45) Date of Patent: *Feb. 8, 2022

(54) INSECT INHIBITORY TOXIN FAMILY ACTIVE AGAINST HEMIPTERAN AND/OR LEPIDOPTERAN INSECTS

(71) Applicant: MONSANTO TECHNOLOGY LLC, St. Louis, MO (US)

(72) Inventors: David J. Bowen, Glencoe, MO (US); Catherine Chay, Ballwin, MO (US); Artem Evdokimov, Orchard Park, NY (US); Stanislaw Flasinski, Chesterfield, MO (US); Uma R. Kesanapalli, Chesterfield, MO (US); Megan N. Schroder, Ames, IA (US); Rachael N. Slightom, Yucca Valley, CA (US); Nengbing Tao, O'Fallon, MO (US); Andrew M. Wollacott, Boston, MA (US)

(73) Assignee: MONSANTO TECHNOLOGY LLC, St. Louis, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/931,303

(22) Filed: May 13, 2020

(65) Prior Publication Data

US 2020/0277620 A1 Sep. 3, 2020

Related U.S. Application Data

(60) Continuation of application No. 16/572,998, filed on Sep. 17, 2019, now Pat. No. 10,689,666, which is a continuation of application No. 16/391,748, filed on Apr. 23, 2019, now Pat. No. 10,669,556, which is a division of application No. 15/486,804, filed on Apr. 13, 2017, now Pat. No. 10,316,331, which is a continuation of application No. 14/945,069, filed on Nov. 18, 2015, now Pat. No. 9,777,289, which is a continuation of application No. 13/441,436, filed on Apr. 6, 2012, now Pat. No. 9,238,678.

(60) Provisional application No. 61/472,865, filed on Apr. 7, 2011.

(51) Int. Cl.
| | |
|---|---|
| C12N 15/82 | (2006.01) |
| A01N 65/04 | (2009.01) |
| C07K 14/32 | (2006.01) |

(52) U.S. Cl.
CPC ......... *C12N 15/8286* (2013.01); *A01N 65/04* (2013.01); *C07K 14/32* (2013.01); *Y02A 40/146* (2018.01)

(58) Field of Classification Search
CPC ... C07K 14/32; C07K 14/325; C12N 15/8286
See application file for complete search history.

(56) References Cited

U.S. PATENT DOCUMENTS

| | | | |
|---|---|---|---|
| 7,541,517 B2 | 6/2009 | Flannagan et al. | |
| 7,601,811 B2 | 10/2009 | Abad et al. | |
| 7,741,118 B1 * | 6/2010 | Fischhoff | C07K 14/005 435/440 |
| 9,238,678 B2 * | 1/2016 | Bowen | C07K 14/32 |
| 9,777,289 B2 * | 10/2017 | Bowen | A01N 65/04 |
| 10,689,666 B2 * | 6/2020 | Bowen | C12N 15/8286 |
| 2006/0024273 A1 | 10/2006 | Flannagan et al. | |
| 2008/0020967 A1 | 1/2008 | Abad et al. | |
| 2008/0070829 A1 | 3/2008 | Carozzi et al. | |
| 2010/0298207 A1 | 11/2010 | Sampson et al. | |
| 2015/0047076 A1 | 2/2015 | Anderson et al. | |

FOREIGN PATENT DOCUMENTS

| | | | |
|---|---|---|---|
| CN | 1527663 A | 9/2004 | |
| CN | 101133079 A | 2/2008 | |
| CN | 101686705 A | 3/2010 | |
| WO | WO 2001/042462 A2 | 6/2001 | |
| WO | WO 2002/022662 A2 | 3/2002 | |
| WO | WO 2002/078437 A2 | 10/2002 | |
| WO | WO 2005/107383 A2 | 11/2005 | |
| WO | WO 2007/027776 A2 | 3/2007 | |
| WO | WO 2007/147096 A2 | 12/2007 | |
| WO | WO-2007147096 A2 * | 12/2007 | ............. C12P 21/02 |
| WO | WO 2008/134072 A2 | 11/2008 | |
| WO | WO 2010/025320 A1 | 3/2010 | |
| WO | WO 2013/152264 A2 | 10/2013 | |

OTHER PUBLICATIONS

Tounsi, S., N. Zouari, and S. Jaoua. "Cloning and study of the expression of a novel cry11a-type gene from *Bacillus thuringiensis* subsp. *kurstaki*." Journal of applied microbiology 95.1 (2003): 23-28 (Year: 2003).*
De Maagd, Ruud A., et al. "Identification of Bacillus thuringiensis delta-endotoxin Cry1C domain III amino acid residues involved in insect specificity." Appl. Environ. Microbiol. 65.10 (1999): 4369-4374. (Year: 1999).*
Aronson, Arthur I., and Yechiel Shai. "Why Bacillus thuringiensis insecticidal toxins are so effective: unique features of their mode of action." FEMS Microbiology Letters 195.1 (2001): 1-8. (Year: 2001).*
Bravo, Alejandra, et al. "Evolution of Bacillus thuringiensis Cry toxins insecticidal activity." Microbial biotechnology 6.1 (2013): 17-26 . (Year: 2013).*
Argolo-Filho et al., "Bacillus thuringiensis is an environmental pathogen and host-specificity has developed as an adaptation to human-generated ecological niches," *Insects*, 5:62-91 (2014).
Aronson et al., "Why *Bacillus thuringiensis* insecticidal toxins are so effective: unique features of their mode of action," *FEMS Microbiol. Lett.*, 195:1-8 (2001).

(Continued)

*Primary Examiner* — Lee A Visone
(74) *Attorney, Agent, or Firm* — Timothy Ball

(57) ABSTRACT

The present invention discloses a genus of insect inhibitory proteins that exhibit properties directed to controlling Lepidopteran and/or Hemipteran crop pests, methods of using such proteins, nucleotide sequences encoding such proteins, methods of detecting and isolating such proteins, and their use in agricultural systems.

20 Claims, 2 Drawing Sheets

Specification includes a Sequence Listing.

(56) References Cited

OTHER PUBLICATIONS

Bravo et al. "Evolution of *Bacillus thuringiensis* Cry toxins insecticidal activity," *Microbiol Biotechnology*, 6:17-26 (2012).
Broun et al., "Catalytic plasticity of fatty acid modification enzymes underlying chemical diversity of plant lipids," *Science*, 282:1315-1317 (1998).
Brown et al., "Molecular Characterization of Two Novel Crystal Protein Genes from *Bacillus thuringiensis* subsp. *thomposoni*," *Journal of Bacteriology*, 174(2):549-557 (1992).
Chougule et al., "Toxins for Transgenic Resistance to Hemipteran Pests," *Toxins*, 4:405-429 (2012).
de Maagd et al. "Identification of *Bacillus thuringiensis* Delta-Endotoxin Cry1C Domain III Amino Acid Residues Involved in Insect Specificity," *Appl. Environ. Microbiol* 65:4369-4374 (1999).
Devos et al., "Practical limits of function prediction," *Proteins: Structure, Function, and Genetics*, 41:98-107 (2000).
Guo et al., "Protein tolerance to random amino acid change," Proceedings of the National Academy of Sciences 101.25:9205-9210. (Year: 2004).

Kisselev, "Polypeptide release factors in prokaryotes and eukaryotes: same function, different structure," *Structure*, 10:8-9 (2002).
McClean, "Nucleic Acid Hybridizations," *DNA—Basics of Structure and Analysis*, www.ndsu.edu/pubweb/~mcclean/plsc731/dna/dna6.htm (1998).
Office Action dated May 10, 2021, in Chinese Patent Application No. 2018110017223, with English translation.
Seffernick et al., "Melamine deaminase and Atrazine chlorohydrolase: 98 percent identical but functionally different," *J. Bacteriol.*, 183(8):2405-2410 (2001).
Tounsi et al. "Cloning and study of the expression of a novel crylla-type gene from *Bacillus thuringiensis* subsp. *kurstaki*," *J. Appl. Microbiol*, 95:23-28 (2003).
Whisstock et al., "Prediction of protein function from protein sequence," *Q. Rev. Biophysics*, 36(3):307-340 (2003).
Wishart et al., "A single mutation converts a novel phosphotyrosine binding domain into a dual-specificity phosphatase," *J. Biol. Chem.*, 270(45):26782-26785 (1995).
Witkowski et al., "Conversion of b-ketoacyl synthase to a Malonyl Decarboxylase by replacement of the active cysteine with glutamine," *Biochemistry*, 38:11643-11650 (1999).

\* cited by examiner

FIGURE 1

| Protein (SEQ ID NO:) | Primary Structure | #aa |
|---|---|---|
| Group 1: TIC1498 (SEQ ID NO:2) | M0 \| M1 \| M2 \| M3 \| M4 [1][2] [3][4] MS$^{2,4}$ | 369 |
| TIC1415 (SEQ ID NO:4) | M0 \| M1 \| M2 \| M3 \| M4 [1][2] [3][4] MS$^{3,4}$ | 386 |
| TIC1497 (SEQ ID NO:6) | M0 \| M1 \| M2 \| M3 \| M4 [1][2] [3][4] MS$^{3,4}$ | 386 |
| TIC1886 (SEQ ID NO:8) | M0 \| M1 \| M2 \| M3 \| M4 [1][2] [3][4] MS$^{1,4}$ | 352 |
| TIC1925 (SEQ ID NO:10) | M0 \| M1 \| M2 \| M3 \| M4 [1][2] [3][4] MS$^{3,4}$ | 386 |
| Group 2: TIC1414 (SEQ ID NO:12) | M0 \| M1 \| M2 \| M3 \| M4 [3] MS$^{1,4}$ | 351 |
| TIC1885 (SEQ ID NO:14) | M0 \| M1 \| M2 \| M3 \| M4 [3] MS$^{2,4}$ | 368 |
| TIC1922 (SEQ ID NO:16) | M0 \| M1 \| M2 \| M3 \| M4 [3] MS$^{3,4}$ | 385 |
| Group 3: TIC1422 (SEQ ID NO:18) | M0 \| M1 \| M2 \| M3 \| M4 [3][4] MS$^{1,4}$ | 352 |
| TIC1974 (SEQ ID NO:20) | M0 \| M1 \| M2 \| M3 \| M4 [3][4] MS$^{1,4}$ | 352 |
| Group 4: TIC2032 (SEQ ID NO:22) | M0 \| M1 \| M2 \| M3 \| M4 [3] MS$^{3,4}$ | 385 |
| Group 5: TIC2120 (SEQ ID NO:24) | M0 \| M1 \| M2 \| M3 MS$^{2,4}$ | 351 |
| Group 6: TIC1362 (SEQ ID NO:26) | M1t \| M2t \| M4t [3][4] | 368 |
| Signature motifs & cleavage sites | M0 \| M1 \| M2 \| M3 \| M4 [1][2] [3][4] MS$^{1,4-3,4}$ / M1t \| M2t \| M4t | |

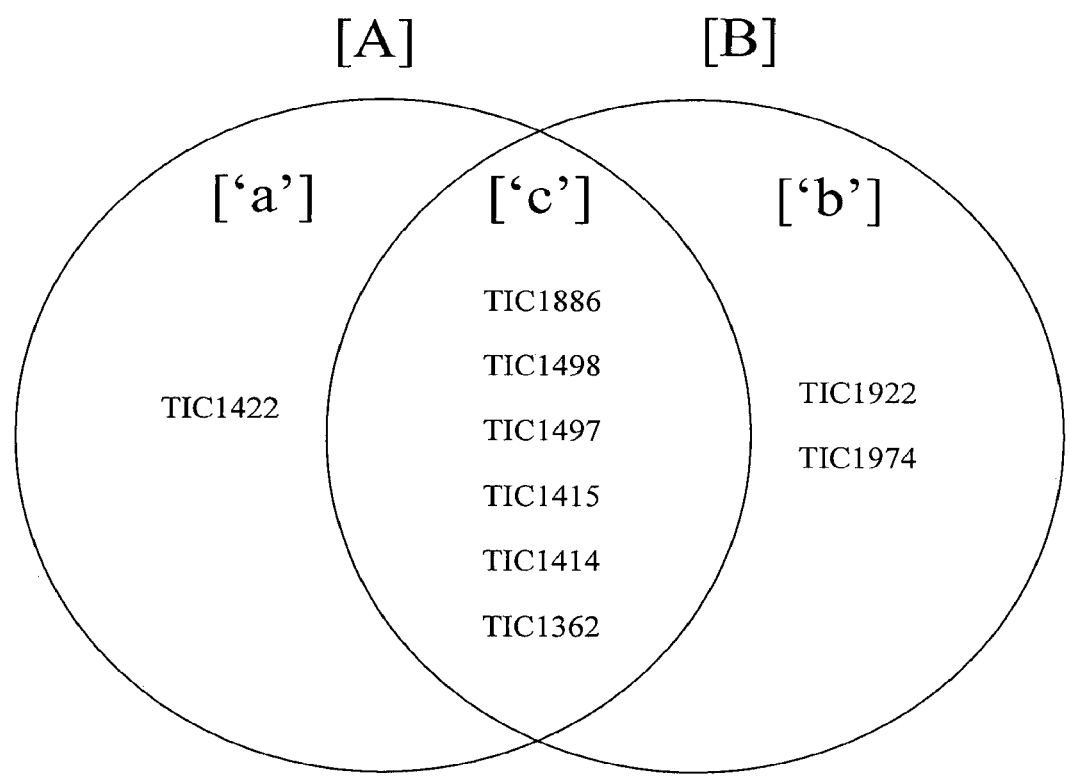

INSECT INHIBITORY TOXIN FAMILY ACTIVE AGAINST HEMIPTERAN AND/OR LEPIDOPTERAN INSECTS

CROSS REFERENCE TO RELATED APPLICATIONS

This application is a continuation of U.S. patent application Ser. No. 16/572,998, filed Sep. 17, 2019, which is a continuation of U.S. patent application Ser. No. 16/391,748, filed Apr. 23, 2019, which is a divisional of U.S. patent application Ser. No. 15/486,804, filed Apr. 13, 2017 (now U.S. Pat. No. 10,316,331), which is a continuation of U.S. patent application Ser. No. 14/945,069, filed Nov. 18, 2015 (now U.S. Pat. No. 9,777,289), which is a continuation of U.S. patent application Ser. No. 13/441,436, filed Apr. 6, 2012 (now U.S. Pat. No. 9,238,678), which claims the benefit of U.S. Provisional Application No. 61/472,865 filed Apr. 7, 2011, all of which are incorporated herein by reference in their entireties.

INCORPORATION OF SEQUENCE LISTING

A sequence listing contained in the file named "P34309US07_SEQ.txt" which is 128,380 bytes (measured in MS-Windows®) and created on May 13, 2020, is filed electronically herewith and incorporated by reference in its entirety.

FIELD OF THE INVENTION

The present invention generally relates to the field of insect inhibitory proteins. In particular, the present invention relates to proteins exhibiting insect inhibitory activity against agriculturally relevant pests of crop plants and seeds, particularly Lepidopteran and/or Hemipteran species of insect pests.

BACKGROUND OF THE INVENTION

Insect inhibitory proteins derived from *Bacillus thuringiensis* (Bt) are known in the art. These proteins are used to control agriculturally relevant pests of crop plants by spraying formulations containing these proteins onto plants/seeds or by expressing these proteins in plants and in seeds.

Only a few Bt proteins have been developed for use in formulations or as transgenic traits for commercial use by farmers to control Coleopteran and Lepidopteran pest species, and no Bt proteins have been used for commercial control of Hemipteran pest species. Certain Hemipteran species, particularly *Lygus* bugs, are pests of cotton and alfalfa, and typically are only controlled using broad spectrum chemistries, e.g., endosulfan, acephate, and oxamyl, which can persist and harm the environment. However, dependence on a limited number of these Bt proteins can result in occurrence of new pests resistant to these proteins, and reliance on broad-spectrum chemistries can harm the environment.

Hence, there is a continuous need for the discovery and commercial development of new proteins active against pests of crop plants.

SUMMARY OF THE INVENTION

The present invention provides a novel group, i.e. a new genus, of insect inhibitory polypeptides (toxin proteins) which are shown to exhibit inhibitory activity against one or more pests of crop plants. Each of the proteins can be used alone or in combination with each other and with other Bt proteins and toxic agents in formulations and in planta, thus providing alternatives to Bt proteins and insecticide chemistries currently in use in agricultural systems.

Recombinant polypeptides are provided which exhibit insect inhibitory activity against Hemipteran and/or Lepidopteran pest species, which optionally:

(a) exhibits at least from about 47% to about 100% amino acid sequence identity, or any percentage point between 47% and 100%, to one or more of the proteins having the amino acid sequence as set forth in any of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, or SEQ ID NO:24;

(b) exhibits at least from about 56% to about 100% amino acid sequence identity, or any percentage point between 56% and 100%, to one or more of the proteins having the amino acid sequence as set forth in any of SEQ ID NO:26, SEQ ID NO:136, or SEQ ID NO:138;

(c) contain in operable position within the polypeptide, at least one of each of six different motif peptide segments in consecutive order M0, M1, M2, M3, M4 and M5, each motif peptide segment exhibiting at least about 80% identity to a consensus sequence specified for the respective motif peptide segment, in which the consensus sequence for motif peptide segment M0 is set forth in SEQ ID NO:31, the consensus sequence for motif peptide segment M1 is set forth in SEQ ID NO:48, the consensus sequence for motif peptide segment M2 is set forth in SEQ ID NO:53, the consensus sequence for motif peptide segment M3 is set forth in SEQ ID NO:62, the consensus sequence for motif peptide segment M4 is set forth in SEQ ID NO:65, and the consensus sequence for motif peptide segment M5 is set forth in SEQ ID NO:139;

(d) contain in operable linkage within the polypeptide, at least one of each of three different motif peptide segments M1t, M2t, and M4t, in consecutive order, wherein each motif peptide segment exhibits at least about 80% identity to a consensus sequence specified for the respective motif peptide segment, and wherein the consensus sequence for motif peptide segment M1t is set forth at SEQ ID NO:70, the consensus sequence for motif peptide segment M2t is set forth at SEQ ID NO:87, and the consensus sequence for motif peptide segment M4t is set forth at SEQ ID NO:120;

(e) contain an amino acid sequence exhibiting from about 195 to about 386 amino acid identities to the amino acid sequence set forth in any of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:136, or SEQ ID NO:138;

(f) contain an amino acid sequence exhibiting at least from about 56 to about 100% identity to the amino acid sequence set forth in any of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, or SEQ ID NO:24;

(g) contain an amino acid sequence exhibiting at least from about 56% to about 100% identity, or any percentage point in between 56% to 100% to the amino acid sequence set forth in any of SEQ ID NO:26, SEQ ID NO:136, and SEQ ID NO:138; or (h) are encoded by a polynucleotide segment that hybridizes under stringent hybridization conditions to one or more of the nucleotide sequences set forth in any of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:20, SEQ ID NO:23, SEQ ID NO:25, SEQ ID NO:135, or SEQ ID NO:137, or the complement thereof.

Insect inhibitory compositions are provided comprising the aforementioned recombinant polypeptides along with methods for controlling Lepidopteran and/or Hemipteran species using such recombinant polypeptides.

Recombinant polynucleotides are provided comprising a nucleotide sequence encoding the aforementioned recombinant polypeptides. Transgenic plant cells, plants, or plant parts comprising such recombinant polynucleotides and methods of controlling a Lepidopteran and/or Hemipteran species pest using such transgenic plant cells, plants or plant parts are also provided.

Processed plant products are provided that comprise a detectable amount of the recombinant polynucleotide. Such processed products include, but are not limited to, plant biomass, oil, meal, animal feed, flour, flakes, bran, lint, hulls, and processed seed.

Methods of making transgenic plants are also provided. Such methods include introducing the recombinant polynucleotide into a plant cell and selecting a transgenic plant that expresses an insect inhibitory amount of the recombinant polypeptide encoded by the recombinant polynucleotide.

Other embodiments, features, and advantages of the invention will be apparent from the following detailed description, examples, and claims.

BRIEF DESCRIPTION OF THE DRAWINGS

FIG. 1 illustrates the primary structure of proteins exemplified in this application, showing the features and motifs characteristic for each of the proteins in this genus. Each protein is depicted by name, SEQ ID NO, structural schematic, and amino acid length (i.e., number of amino acids), and organized into groups or clusters based on amino acid identity between the various proteins. The proteins within a group generally exhibit at least about 90% amino acid identity. Generally, most proteins in the genus of novel proteins disclosed herein contain, in operable linkage within the polypeptide, at least one of each of six different signature motifs (M) or motif peptide segments, each motif being unique to this genus of proteins. The motifs are referenced herein and consecutively numbered as M0, M1, M2, M3, M4 and M5. The M0 motif is proximal to the amino terminus of each protein toxin, and the M5 motif is positioned most proximal to the carboxy terminus of each protein toxin. The M5 motif can also be present in more than one copy in each protein. Each motif contains a core amino acid segment unique to that particular motif. The presence of any of the referenced motif peptide segments in a protein derived from Bacillus thuringiensis or related species of bacilli, and the observation for such protein of toxic activity directed to one or more species of Hemiptera and/or Lepidoptera, is sufficient to provide for classification of such protein as being within the scope of the present invention, particularly if the full length of the protein amino acid sequence exhibits at least about 47% or greater identity to any of the proteins embodied herein including proteins as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, or SEQ ID NO:24. Secondary motifs observed within each of the major motifs M0-M5 in certain of the proteins of the present invention are referenced herein as M1t, M2t, and M4t. Certain of the proteins also contain proteolytic cleavage sites KK, EH, TF, and FG, the relative positions of each being marked in applicable proteins represented in FIG. 1 as [1], [2], [3], and [4], respectively (the two letters represent the two amino acid residues bracketing the cleavage site), are features of proteins within the scope of this invention.

FIG. 2 is a Venn diagram depicting the activity profile of the proteins of the present invention. Circle [A] represents Lepidopteran-active proteins, while Circle [B] represents Hemipteran-active proteins. Area ['c'] is an intersection of Circles [A] and [B], which represents proteins that tested positive for activity against both Lepidopteran and Hemipteran insects. Area ['a'] is [A] minus ['c'], which represents proteins that tested positive for activity against Lepidopteran insects but not positive for any activity against Hemipteran species indicated at the dose at which Lepidopteran activity was observed. Area ['b'] is [B] minus ['c'], which represents proteins that tested positive for activity against Hemipteran insects but not positive for activity against the Lepidopteran species indicated at the dose at which Hemipteran species activity was observed.

BRIEF DESCRIPTION OF THE SEQUENCES

SEQ ID NO:1 is a nucleotide sequence representing a recombinant polynucleotide derived from a *Bacillus thuringiensis* (Bt) species having an open reading frame at nucleotide positions 1-1107 encoding a TIC1498 protein.

SEQ ID NO:2 is an amino acid sequence of a TIC1498 protein toxin.

SEQ ID NO:3 is a nucleotide sequence representing a recombinant polynucleotide derived from a Bt species having an open reading frame at nucleotide positions 1-1158 encoding a TIC1415 protein.

SEQ ID NO:4 is an amino acid sequence of a TIC1415 protein toxin.

SEQ ID NO:5 is a nucleotide sequence representing a recombinant polynucleotide derived from a Bt species having an open reading frame at nucleotide positions 1-1158 encoding a TIC1497 protein.

SEQ ID NO:6 is an amino acid sequence of a TIC1497 protein toxin.

SEQ ID NO:7 is a nucleotide sequence representing a recombinant polynucleotide derived from a Bt species having an open reading frame at nucleotide positions 1-1056 encoding a TIC1886 protein.

SEQ ID NO:8 is an amino acid sequence of a TIC1886 protein toxin.

SEQ ID NO:9 is a nucleotide sequence representing a recombinant polynucleotide derived from a Bt species having an open reading frame at nucleotide positions 1-1158 encoding a TIC1925 protein.

SEQ ID NO:10 is an amino acid sequence of a TIC1925 protein toxin.

SEQ ID NO:11 is a nucleotide sequence representing a recombinant polynucleotide derived from a Bt species having an open reading frame at nucleotide positions 1-1053 encoding a TIC1414 protein.

SEQ ID NO:12 is an amino acid sequence of a TIC1414 protein toxin.

SEQ ID NO:13 is a nucleotide sequence representing a recombinant polynucleotide derived from a Bt species having an open reading frame at nucleotide positions 1-1104 encoding a TIC1885 protein.

SEQ ID NO:14 is an amino acid sequence of a TIC1885 protein toxin.

SEQ ID NO:15 is a nucleotide sequence representing a recombinant polynucleotide derived from a Bt species having an open reading frame at nucleotide positions 1-1155 encoding a TIC1922 protein.

SEQ ID NO:16 is an amino acid sequence of a TIC1922 protein toxin.

SEQ ID NO:17 is a nucleotide sequence representing a recombinant polynucleotide derived from a Bt species having an open reading frame at nucleotide positions 1-1056 encoding a TIC1422 protein.

SEQ ID NO:18 is an amino acid sequence of a TIC1422 protein toxin.

SEQ ID NO:19 is a nucleotide sequence representing a recombinant polynucleotide derived from a Bt species having an open reading frame at nucleotide positions 1-1056 encoding a TIC1974 protein.

SEQ ID NO:20 is an amino acid sequence of a TIC1974 protein toxin.

SEQ ID NO:21 is a nucleotide sequence representing a recombinant polynucleotide derived from a Bt species having an open reading frame at nucleotide positions 1-1155 encoding a TIC2032 protein.

SEQ ID NO:22 is an amino acid sequence of a TIC2032 protein toxin.

SEQ ID NO:23 is a nucleotide sequence representing a recombinant polynucleotide derived from a Bt species having an open reading frame at nucleotide positions 1-1104 encoding a TIC2120 protein.

SEQ ID NO:24 is an amino acid sequence of a TIC2120 protein toxin.

SEQ ID NO:25 is a nucleotide sequence representing a recombinant polynucleotide derived from a Bt species having an open reading frame at nucleotide positions 1-1053 encoding a TIC1362 protein.

SEQ ID NO:26 is an amino acid sequence of a TIC1362 protein toxin.

SEQ ID NO:27 is an artificial nucleotide sequence encoding a TIC1415 protein.

SEQ ID NO:28 is an artificial nucleotide sequence encoding a TC1414 protein.

SEQ ID NO:29 is an artificial nucleotide sequence encoding a TIC1422 protein.

SEQ ID NO:30 is an artificial nucleotide sequence encoding a TIC1362 protein.

SEQ ID NO:31 is a consensus amino acid sequence for the M0 motif segment.

SEQ ID NOs:32-47 are each individual amino acid sequences from each of the various toxin proteins disclosed herein which were used in formulating the consensus sequence as set forth in SEQ ID NO:31.

SEQ ID NO:48 is a consensus amino acid sequence for the M1 motif segment.

SEQ ID NOs:49-52 are each individual amino acid sequences from each of the various toxin proteins disclosed herein which were used in formulating the consensus sequence as set forth in SEQ ID NO:48.

SEQ ID NO:53 is a consensus amino acid sequence for the M2 motif segment.

SEQ ID NOs:54-61 are each individual amino acid sequences from each of the various toxin proteins disclosed herein which were used in formulating the consensus sequence as set forth in SEQ ID NO:53.

SEQ ID NO:62 is a consensus amino acid sequence for the M3 motif segment.

SEQ ID NOs:63-64 are each individual amino acid sequences from each of the various toxin proteins disclosed herein which were used in formulating the consensus sequence as set forth in SEQ ID NO:62.

SEQ ID NO:65 is a consensus amino acid sequence for the M4 motif segment.

SEQ ID NOs:66-69 are each individual amino acid sequences from each of the various toxin proteins disclosed herein which were used in formulating the consensus sequence as set forth in SEQ ID NO:65.

SEQ ID NO:70 is a consensus amino acid sequence for the M1t motif segment.

SEQ ID NOs:71-86 are each individual amino acid sequences from each of the various toxin proteins disclosed herein which were used in formulating the consensus sequence as set forth in SEQ ID NO:70.

SEQ ID NO:87 is a consensus amino acid sequence for the M2t motif segment.

SEQ ID NOs:88-119 are each individual amino acid sequences from each of the various toxin proteins disclosed herein which were used in formulating the consensus sequence as set forth in SEQ ID NO:87.

SEQ ID NO:120 is a consensus amino acid sequence for the M4t motif segment.

SEQ ID NOs:121-122 are each individual amino acid sequences from each of the various toxin proteins disclosed herein which were used in formulating the consensus sequence as set forth in SEQ ID NO:120.

SEQ ID NO:123 is an amino acid sequence representing an insect inhibitory fragment of TIC1497 and corresponds to an amino acid translation of nucleotide positions 1 through 933 of SEQ ID NO:5.

SEQ ID NO:124 is an amino acid sequence representing an insect inhibitory fragment of TIC1497 and corresponds to an amino acid translation of nucleotide positions 1 through 885 of SEQ ID NO:5.

SEQ ID NO:125 is an amino acid sequence representing an insect inhibitory fragment of TIC1497 and corresponds to an amino acid translation of nucleotide positions 1 through 939 of SEQ ID NO:5.

SEQ ID NO:126 is an amino acid sequence representing an insect inhibitory fragment of TIC1497 and corresponds to an amino acid translation of nucleotide positions 1 through 882 of SEQ ID NO:5.

SEQ ID NO:127 is an oligonucleotide sequence in a primer for hybridizing to the (+) strand of the 5' end of DNA encoding a protein of the present invention and corresponds to positions 1 . . . 29 of SEQ ID NO:3 (tic1415 forward primer).

SEQ ID NO:128 is an oligonucleotide sequence in a primer for hybridizing to the (−) strand of the 3' end of DNA encoding a protein of the present invention and corresponds to positions 1131 . . . 1161 of SEQ ID NO:3 (tic1415 reverse primer).

SEQ ID NO:129 is an oligonucleotide sequence in a primer for hybridizing to the (+) strand of the 5' end of DNA encoding a protein of the present invention and corresponds to positions 1 . . . 40 of SEQ ID NO:11 (tic1414 forward primer).

SEQ ID NO:130 is an oligonucleotide sequence in a primer for hybridizing to the (−) strand of the 3' end of DNA encoding a protein of the present invention and corresponds to positions 1015 . . . 1056 of SEQ ID NO:11 (tic1414 reverse primer).

SEQ ID NO:131 is an oligonucleotide sequence in a primer for hybridizing to the (+) strand of the 5' end of DNA encoding a protein of the present invention and corresponds to positions 1 . . . 35 of SEQ ID NO:17 (tic1422 forward primer).

SEQ ID NO:132 is an oligonucleotide sequence in a primer for hybridizing to the (−) strand of the 3' end of DNA encoding a protein of the present invention and corresponds to positions 1021-1059 of SEQ ID NO:17 (tic1422 reverse primer).

SEQ ID NO:133 is an oligonucleotide sequence in a primer for hybridizing to the (+) strand of the 5' end of DNA encoding a protein of the present invention and corresponds to positions 1 . . . 28 of SEQ ID NO:25 (tic1362 forward primer).

SEQ ID NO:134 is an oligonucleotide sequence in a primer for hybridizing to the (−) strand of the 3' end of DNA encoding a protein of the present invention and corresponds to positions 1025-1056 of SEQ ID NO:25 (tic1362 reverse primer).

SEQ ID NO:135 is a nucleotide sequence representing a recombinant polynucleotide derived from a *Bacillus thuringiensis* (Bt) species having an open reading frame at nucleotide positions 1-1008 encoding a TIC2335 protein.

SEQ ID NO:136 is an amino acid sequence of a TIC2335 protein toxin.

SEQ ID NO:137 is a nucleotide sequence representing a polynucleotide derived from a *Bacillus thuringiensis* (Bt) species having an open reading frame at nucleotide positions 1-1014 encoding a TIC2334 protein.

SEQ ID NO:138 is an amino acid sequence of a TIC2334 protein toxin.

SEQ ID NO:139 is a consensus amino acid sequence for the M5 motif segment.

SEQ ID NOs:140-141 are each individual amino acid sequences from each of the various toxin proteins disclosed herein which were used in formulating the consensus sequence as set forth in SEQ ID NO:139.

SEQ ID NO:142 is an N-terminal consensus sequence shared by proteins of the present invention.

SEQ ID NO:143 is a C-terminal consensus sequence shared by proteins of the present invention.

DETAILED DESCRIPTION OF THE INVENTION

*Bacillus thuringiensis* (Bt) proteins are a rich source of diverse toxin proteins; however, many problems exist in the process of identifying new Bt toxins. Screening methods that involve morphological typing of Bt strains, (e.g. structural analysis of parasporal inclusion bodies, cell coat morphology, visible color, and morphology under different growing conditions), do not provide a good correlation with the presence of novel toxic proteins. Additionally, screening methods that involve highly matrixed bioassay processes for identifying proteins with toxic properties yield inconsistent results. Such processes include but may not be limited to testing proteins expressed at various stages of Bt growth and development, testing different Bt protein preparations, testing Bt proteins activated by various proteolytic treatments, testing Bt proteins with other ancillary proteins, and testing Bt proteins under various induction conditions. Some screening methods rely on structural and functional design, which require very labor and skill intensive procedures to elucidate structure/function relationships, and often these protocols can only be effective when carried out on fully elucidated toxins. In view of the inherent problems in finding new Bt toxin proteins, screening for genes encoding Bt toxin proteins has changed due to recent improvements in bioinformatics and genome sequence capabilities.

The inventors herein have taken advantage of high throughput sequencing and improvements in bioinformatics capabilities to screen Bt genomes for novel protein-encoding Bt toxin genes, which are then cloned and expressed in acrystalliferous Bt strains to produce protein samples for insect inhibitory activity screening. As described herein and using this method, a novel protein genus has been discovered and exemplary proteins exhibiting insecticidal activity against Hemipteran and/or Lepidopteran species. Those skilled in the art will appreciate that the teaching of the present invention enables related gene/protein members to be identified or engineered that exhibit the properties and features of the proteins of the present invention.

The polypeptides/proteins of the present invention are related by source or origin (from B.t. strains of bacteria), by biological toxin activity against insect pests within the orders Hemiptera and/or Lepidoptera, by primary structure (conserved amino acid sequences), and by length (from about 300 to about 400 amino acids).

Proteins of the present invention, and proteins that resemble the proteins of the present invention, can be identified by comparison to each other using various computer based algorithms known in the art. Amino acid identities reported herein are a result of a Clustal W alignment using these default parameters: Weight matrix: blosum, Gap opening penalty: 10.0, Gap extension penalty: 0.05, Hydrophilic gaps: On, Hydrophilic residues: GPSNDQERK, Residue-specific gap penalties: On (Thompson et al (1994) Nucleic Acids Research, 22:4673-4680).

It is intended that a recombinant polypeptide exhibiting insect inhibitory activity against a Lepidopteran and/or Hemipteran insect species is within the scope of the present invention if an alignment of the polypeptide with any of SEQ ID NO:2 (TIC1498), SEQ ID NO:4 (TIC1415), SEQ ID NO:6 (TIC1497), SEQ ID NO:8 (TIC1886), SEQ ID NO:10 (TIC1925), SEQ ID NO:12 (TIC1414), SEQ ID NO:14 (TIC1885), SEQ ID NO:16 (TIC1922), SEQ ID NO:18 (TIC1422), SEQ ID NO:20 (TIC1974), SEQ ID NO:22 (TIC2032), SEQ ID NO:24 (TIC2120), SEQ ID NO:26 (TIC1362), SEQ ID NO:136 (TIC2335), and SEQ ID NO:138 (TIC2334) results in at least 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, or 386 amino acid identities. See Table 1. That is, in certain embodiments, the recombinant polypeptide of the present invention comprises an amino acid sequence exhibiting 195-386 amino acid identities when compared to SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:136, and SEQ ID NO:138.

Polypeptides/proteins of the present invention are observed to be related by the presence of six signature amino acid sequence motif segments known to exist only in members of this particular insect inhibitory protein family. The

TABLE 1

Pair-wise matrix display of toxin proteins of the present invention.

| (M) | (N) 2 | 4 | 6 | 8 | 10 | 12 | 14 | 16 | 18 | 20 | 22 | 24 | 26 | 136 | 138 |
|---|---|---|---|---|---|---|---|---|---|---|---|---|---|---|---|
| SEQ ID NO: 2 (TIC1498) | — 366 | 99.2 365 | 98.9 349 | 94.6 366 | 99.2 280 | 75.9 295 | 79.9 308 | 83.5 314 | 85.1 312 | 84.6 337 | 91.3 296 | 80.2 170 | 46.1 137 | 37.1 138 | 37.4 |
| SEQ ID NO: 4 (TIC1415) | 94.8 366 | — 384 | 99.5 349 | 90.4 385 | 99.7 293 | 75.9 308 | 79.8 324 | 83.9 314 | 81.3 312 | 80.8 357 | 92.5 308 | 79.8 175 | 45.3 137 | 35.5 138 | 35.8 |
| SEQ ID NO: 6 (TIC1497) | 94.6 365 | 99.5 384 | — 348 | 90.2 385 | 99.7 293 | 75.9 308 | 79.8 324 | 83.9 313 | 81.1 311 | 80.6 355 | 92 308 | 79.8 174 | 45.1 137 | 35.5 138 | 35.8 |
| SEQ ID NO: 8 (TIC1886) | 99.1 349 | 99.1 349 | 98.9 348 | — 349 | 99.1 281 | 79.8 292 | 83 293 | 83.2 313 | 88.9 311 | 88.4 320 | 90.9 293 | 83.2 169 | 48 137 | 38.9 139 | 39.5 |
| SEQ ID NO: 10 (TIC1925) | 94.8 366 | 99.7 385 | 99.7 385 | 90.4 349 | — 294 | 76.2 309 | 80.1 325 | 84.2 314 | 81.3 312 | 80.8 356 | 92.2 309 | 80.1 175 | 45.3 137 | 35.5 138 | 35.8 |
| SEQ ID NO: 12 (TIC1414) | 79.8 280 | 83.5 293 | 83.5 293 | 80.1 281 | 83.8 294 | — 350 | 99.7 351 | 100 272 | 77.5 270 | 76.9 319 | 90.9 287 | 81.8 158 | 45 137 | 39 136 | 38.7 |
| SEQ ID NO: 14 (TIC1885) | 80.2 295 | 83.7 308 | 83.7 308 | 79.3 292 | 84 309 | 95.1 350 | — 367 | 99.7 284 | 77.2 282 | 76.6 334 | 90.8 302 | 82.1 168 | 45.7 137 | 37.2 135 | 36.7 |
| SEQ ID NO: 16 (TIC1922) | 80 308 | 84.2 324 | 84.2 324 | 76.1 293 | 84.4 325 | 91.2 351 | 95.3 367 | — 285 | 74 283 | 73.5 350 | 90.9 303 | 78.7 168 | 43.6 137 | 35.6 136 | 35.3 |
| SEQ ID NO: 18 (TIC1422) | 89.2 314 | 89.2 314 | 88.9 313 | 88.9 313 | 89.2 314 | 77.3 272 | 80.7 284 | 81 285 | — 350 | 99.4 300 | 85.2 279 | 79.3 166 | 47.2 134 | 38.1 139 | 39.5 |
| SEQ ID NO: 20 (TIC1974) | 88.6 312 | 88.6 312 | 88.4 311 | 88.4 312 | 88.6 270 | 76.7 282 | 80.1 283 | 80.4 350 | 99.4 — | 84.7 298 | 78.7 277 | 47.2 166 | 38.1 134 | 39.5 139 | |
| SEQ ID NO: 22 (TIC2032) | 87.5 337 | 92.7 357 | 92.2 355 | 83.1 320 | 92.5 356 | 82.9 319 | 86.8 334 | 90.9 350 | 77.9 300 | 77.4 298 | — 309 | 80.3 175 | 45.5 136 | 35.3 136 | 35.3 |
| SEQ ID NO: 24 (TIC2120) | 80.4 296 | 83.7 308 | 83.7 308 | 79.6 293 | 84 309 | 78 287 | 82.1 302 | 82.3 303 | 75.8 279 | 75.3 277 | 84 309 | — 169 | 45.9 131 | 35.6 139 | 37.8 |
| SEQ ID NO: 26 (TIC1362) | 48.4 170 | 49.9 175 | 49.6 174 | 48.1 169 | 49.9 175 | 45 158 | 47.9 168 | 47.9 168 | 47.3 166 | 47.3 166 | 49.9 175 | 48.1 169 | — 146 | 41.6 133 | 37.9 |
| SEQ ID NO: 136 (TIC2335) | 40.8 137 | 40.8 137 | 40.8 137 | 40.8 137 | 40.8 137 | 40.8 137 | 40.8 137 | 40.8 137 | 39.9 134 | 39.9 134 | 40.5 136 | 39 131 | 43.5 146 | — | 39 131 |
| SEQ ID NO: 138 (TIC2334) | 40.8 138 | 40.8 138 | 40.8 138 | 41.1 139 | 40.8 138 | 40.2 136 | 39.9 135 | 40.2 136 | 41.1 139 | 41.1 139 | 40.2 136 | 41.1 139 | 39.3 133 | 38.8 131 | — |

(M) is SEQ ID NO and protein name (TIC#)
(N) is SEQ ID NO.
The percent amino acid identity between all pairs is calculated relative to (M) and is represented by the upper numbers.
The lower number in each box in the matrix represents the numbers of identical amino acids between the pair.
The last three rows represent closely related toxin proteins which are more distantly related to the other proteins in the table.

It is also intended that a first protein exhibiting insect inhibitory activity is within the scope of the present invention if a Clustal W alignment of such protein with any of the following second proteins set forth in any of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, results in at least about 47% amino acid sequence identity between the first and the second proteins; or specifically, at least 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.2, 99.5, 99.8, or 100% amino acid sequence identity between the first and the second proteins; or optionally a first protein exhibiting insect inhibitory activity is within the scope of the present invention if a Clustal W alignment of such protein with any of the following second proteins set forth in any of SEQ ID NO:26, SEQ ID NO:136, or SEQ ID NO:138, results in at least about 56% amino acid sequence identity between the first and the second proteins; or specifically, at least 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 99.2, 99.5, 99.8, or 100% amino acid sequence identity between the first and the second proteins.

relative position of each of the signature motif segments is illustrated in FIG. 1 as "M0", "M1", "M2", "M3", "M4", and "M5". SEQ ID NO:31 represents the M0 motif consensus sequence, in which $X_1$ is N or T, $X_2$ is D or A, $X_3$ is I or T, and $X_4$ is R or S. Each M0 motif segment is represented by the corresponding amino acid sequences set forth in SEQ ID NOs:32-47. The M0 motif segment corresponds to amino acid sequence positions 48 through 70 of SEQ ID NO:2, SEQ ID NO:4, SEQ ID NO:6, SEQ ID NO:8, SEQ ID NO:10, SEQ ID NO:18, and SEQ ID NO:20, positions 47 through 69 of SEQ ID NO:12, SEQ ID NO:14, SEQ ID NO:16, SEQ ID NO:22, and SEQ ID NO:24. A core amino acid sequence $QX_2FQTX_3PX_4L$ is embedded within the M0 motif segment. The presence of this core sequence (or the M0 motif segment), or of a peptide segment exhibiting at least about 80% amino acid sequence identity to this core sequence (or the M0 motif segment) in a particular toxin protein derived from Bt, alone or in combination with other motif segments described herein and operably positioned within the primary sequence of any such toxin protein, is determinative that the toxin protein is a member of the genus of proteins described herein, particularly when the protein is also shown to exhibit insect inhibitory properties.

SEQ ID NO:48 represents the M1 motif consensus sequence, in which $X_1$ is V or I, and $X_2$ is R or K. Each M1 motif is represented by the corresponding amino acid sequences set forth in SEQ ID NOs:49-52. The M1 motif corresponds to amino acid sequence positions 76 through 118 of SEQ ID NO:2, SEQ ID NO:4, SEQ ID NO:6, SEQ ID NO:8, SEQ ID NO:10, SEQ ID NO:18, and SEQ ID NO:20, and positions 75 through 117 of SEQ ID NO:12, SEQ ID NO:14, SEQ ID NO:16, SEQ ID NO:22, and SEQ ID NO:24, or any shorter segment comprising the core amino acid sequence QTX$_1$SFNEX$_2$TT of this M1 motif. The presence of this core sequence (or the M1 motif), or of a peptide segment exhibiting at least 80% amino acid sequence identity to this core sequence (or the M1 motif), in a particular protein derived from Bt, alone or in combination with other motifs described herein, is determinative that the protein is a member of the genus of proteins described herein, particularly when the protein is also shown to exhibit insect inhibitory properties. Certain proteins within the genus of proteins exemplified herein include the M1 motif as well as a secondary core motif segment Mt1 represented by the consensus amino acid sequence as set forth in SEQ ID NO:70, in which X$_1$ is V or F, X$_2$ is S or T, X$_3$ is H or T, and X$_4$ is V or T. Each M1t secondary core motif segment is represented by the amino acid sequences set forth in SEQ ID NOs:71-86. M1t corresponds to amino acid positions 94 through 112 of SEQ ID NO:2, SEQ ID NO:4, SEQ ID NO:6, SEQ ID NO:8, SEQ ID NO:10, SEQ ID NO:18, and SEQ ID NO:20, positions 93 through 111 of SEQ ID NO:12, SEQ ID NO:14, SEQ ID NO:16, SEQ ID NO:22, and SEQ ID NO:24, and positions 83 through 101 of SEQ ID NO:26. The presence of this secondary core motif M1t, or of a peptide segment exhibiting at least 80% amino acid sequence identity to this secondary core motif, in a particular protein derived from Bt, alone or in combination with other motifs described herein, is determinative that the protein is a member of the genus of proteins described herein, particularly when the protein is also shown to exhibit insect inhibitory properties.

SEQ ID NO:53 represents the M2 motif consensus sequence, in which X$_1$ is S or A, X$_2$ is V or T, and X$_3$ is T or S. Each M2 motif is represented by the corresponding amino acid sequences set forth in SEQ ID NOs:54-61. The M2 motif corresponds to amino acid positions 134 through 170 of SEQ ID NO:2, SEQ ID NO:4, SEQ ID NO:6, SEQ ID NO:8, SEQ ID NO:10, SEQ ID NO:18, and SEQ ID NO:20, and positions 133 through 169 of SEQ ID NO:12, SEQ ID NO:14, SEQ ID NO:16, SEQ ID NO:22, and SEQ ID NO:24. The presence of this M2 motif, or of a peptide segment exhibiting at least 80% amino acid sequence identity to this M2 motif, in a particular protein derived from Bt, alone or in combination with other motifs described herein, is determinative that the protein is a member of the genus of proteins described herein, particularly when the protein is also shown to exhibit insect inhibitory properties. Certain proteins within the genus of proteins exemplified herein include as a part of the M2 motif a secondary motif M2t as set forth in SEQ ID NO:87, in which X$_1$ is E or A, X$_2$ is G or S, X$_3$ is V or T, X$_4$ is T or S, X$_5$ is L or I. Each M2t motif is represented by amino acid sequences set forth in SEQ ID NOs:88-119. M2t corresponds to amino acid positions 153 through 168 of SEQ ID NO:2, SEQ ID NO:4, SEQ ID NO:6, SEQ ID NO:8, SEQ ID NO:10, SEQ ID NO:18, and SEQ ID NO:20, positions 152 through 167 of SEQ ID NO:12, SEQ ID NO:14, SEQ ID NO:16, SEQ ID NO:22, and SEQ ID NO:24, and positions 139 through 154 of SEQ ID NO:26. The presence of this motif M2t or of a peptide segment exhibiting at least 80% amino acid sequence identity to this motif M2t in a particular protein derived from Bt, alone or in combination with other motifs described herein, is determinative that the protein is a member of the genus of proteins described herein, particularly when the protein is also shown to exhibit insect inhibitory properties.

SEQ ID NO:62 represents the M3 motif consensus sequence, in which X$_1$ is D or N. Each M3 motif is represented by amino acid sequences set forth in SEQ ID NOs:63-64. M3 corresponds to amino acid positions 172 through 200 of SEQ ID NO:2, SEQ ID NO:4, SEQ ID NO:6, SEQ ID NO:8, SEQ ID NO:10, SEQ ID NO:18, and SEQ ID NO:20, and positions 171 through 199 of SEQ ID NO:12, SEQ ID NO:14, SEQ ID NO:16, SEQ ID NO:22, and SEQ ID NO:24, or any shorter segment comprising the core amino acid sequence AGSVX$_1$VPID of this M3 motif. The presence of this M3 motif or its core, or of a peptide segment exhibiting at least 80% amino acid sequence identity to this M3 motif or to its core sequence, alone or in combination with other motifs described herein, in a particular protein derived from Bt is determinative that the protein is a member of the genus of proteins described herein, particularly when the protein is also shown to exhibit insect inhibitory properties.

SEQ ID NO:65 represents the M4 motif consensus sequence, in which X$_1$ is P or T, and X$_2$ is D or N. Each M4 motif is represented by amino acid sequences set forth in SEQ ID NOs:66-69. M4 corresponds to amino acid positions 267 through 294 of SEQ ID NO:2, SEQ ID NO:4, SEQ ID NO:6, SEQ ID NO:8, SEQ ID NO:10, SEQ ID NO:18, and SEQ ID NO:20, and positions 266 through 293 of SEQ ID NO:12, SEQ ID NO:14, SEQ ID NO:16, and SEQ ID NO:22, or any shorter segment comprising the core amino acid sequence SLATX$_1$X$_2$QILS of this M4 motif. The presence of this M4 motif or its core, or of a peptide segment exhibiting at least 80% amino acid sequence identity to this M4 motif or to its core sequence, alone or in combination with other motifs described herein, in a particular protein derived from Bt, is determinative that the protein is a member of the genus of proteins described herein, particularly when the protein is also shown to exhibit insect inhibitory properties. Certain proteins within the genus of proteins exemplified herein include as a part of the M4 motif a secondary motif M4t as set forth in SEQ ID NO:120, in which X$_1$ is A or T. Each M4t motif is represented by amino acid sequences SEQ ID NO:121 and SEQ ID NO:122. The M4t motif corresponds to amino acid positions 267 through 281 of SEQ ID NO:2, SEQ ID NO:4, SEQ ID NO:6, SEQ ID NO:8, SEQ ID NO:10, SEQ ID NO:18, and SEQ ID NO:20, positions 266 through 280 of SEQ ID NO:12, SEQ ID NO:14, SEQ ID NO:16, and SEQ ID NO:22, and positions 254 through 268 of SEQ ID NO:26, or any shorter segment comprising the core amino acid sequence PGFTGETR. The presence of this M4t motif, or of a peptide segment exhibiting at least 80% amino acid sequence identity to this M4t motif, alone or in combination with other motifs described herein, in a particular protein derived from Bt, is determinative that the protein is a member of the genus of proteins described herein, particularly when the protein is also shown to exhibit insect inhibitory properties.

SEQ ID NO:139 represents the M5 motif consensus sequence segment, in which X$_1$ is C, Y or R, X2 is H or R, X3 is N, D or H, X4 is Y or H, X5 is R or G, and X6 is D or N. SEQ ID NOs:142-143 are two exemplary M5 motifs. M5 corresponds to amino acid positions 327 through 343 of SEQ ID NOs: 12, 14, 16, 22, and 24, positions 328 through 344 of SEQ ID NOs: 2, 4, 6, 8, 10, 18, and 20, positions 344 through 360 of SEQ ID NOs: 14, 16, 22, and 24, positions 345 through 361 of SEQ ID NOs: 2, 4, 6, and 10, positions 361 through 377 of SEQ ID NOs: 12, 16, and 22, positions 362 through 378 of SEQ ID NOs: 4, 6, and 10, or any shorter segment comprising the core amino acid sequence (C/Y) EHNYDE of this M5 motif. The core amino acid sequence (C/Y)EHNYDE of this M5 motif corresponds to seven of the last 8 N-terminal amino acid residues in SEQ ID NOs: 2, 4, 6, 8, 10, 12, 14, 16, 18, 20, 22, and 24. The presence of this M5 motif or its core, or of a peptide segment exhibiting at least 80% amino acid sequence identity to this M5 motif, alone or in combination with other motifs described herein, in a particular protein derived from Bt is determinative that the protein is a member of the genus of proteins described herein, particularly when the protein is also shown to exhibit insect inhibitory properties. The polypeptides/proteins of the present invention are related by this M5 motif which can occur once as exemplified by SEQ ID NOs: 8, 12, 18, and 20; as a double repeat as exemplified by SEQ ID NOs: 2, 14, and 24; and as a triple repeat as exemplified by SEQ ID NOs: 4, 6, 10, 12, 16, and 22. Interestingly, TIC1414 and TIC1922 can be aligned with 100% identity with reference to TIC1414 (Table 1), which is possible because the difference between TIC1414 and TIC1922 are two repeats of the M5 motif (gaps allowed in the pair-wise alignment).

The present invention provides a recombinant polypeptide comprising a peptide segment exhibiting at least 80, 81, 82, 83, 84, 85, 86, 87, 88, 89, 90, 91, 92, 93, 94, 95, 96, 97, 98, 99, or 100% amino acid sequence identity to an amino acid sequence selected from the group consisting of SEQ ID NO:31 (motif M0), SEQ ID NO:48 (motif M1), SEQ ID NO:53 (motif M2), SEQ ID NO:62 (motif M3), SEQ ID NO:65 (motif M4), SEQ ID NO:141 (motif M5), SEQ ID NO:70 (motif M10, SEQ ID NO:87 (motif M2t), SEQ ID NO:120 (motif M40, and any combination thereof. Such polypeptide exhibits insect inhibitory activity against Lepidopteran and/or Hemipteran species. As used herein, the term "insect inhibitory activity" refers to activity of a protein, or a fragment thereof, effective in inhibiting a pest, preferably a pest of one or more crop plants, when provided in the diet of the pest and ingested by the target (intended) pest. Pests of crop plants include nematodes and arthropods, including insects. Proteins of the present invention are effective in inhibiting the growth, development, viability or fecundity of a particular target pest, particularly an insect pest, including but not limited to insects of the orders Lepidoptera and Hemiptera.

In certain embodiments, the insect inhibitory polypeptides/proteins contain amino acid segments exhibiting at least 80, 81, 82, 83, 84, 85, 86, 87, 88, 89, 90, 91, 92, 93, 94, 95, 96, 97, 98, 99, or 100% identity to any one or more of the signature motifs (SEQ ID NOs:31-122, 142 and 143) of the proteins of the present invention.

In certain embodiments, the recombinant polypeptide comprises the amino acid sequence as set forth in SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:136, or SEQ ID NO:138, or an insect inhibitory fragment thereof. Exemplary insect inhibitory fragments include, but not limited to, those comprising the amino acid sequence as set forth in SEQ ID NO:123, SEQ ID NO:124, SEQ ID NO:125, and SEQ ID NO:126.

Additional signature motifs include proteolytic cleavage sites "KK", "EH", "TF", and "FG", the relative positions of each shown as [1], [2], [3], and [4], respectively in FIG. 1.

An additional signature motif includes an N-terminal consensus sequence as set forth in SEQ ID NO:142, where $X_1$ is A or E, $X_2$ is N or D, $X_3$ is Q or E, and $X_4$ is S or L, shared by proteins that are members of the genus of proteins exemplified herein, with the exception of the protein having the amino acid sequence as set forth in SEQ ID NO:26. Forward oligonucleotide primers, e.g., SEQ ID NO:127, SEQ ID NO:129, SEQ ID NO:131, and SEQ ID NO:133 can be designed to hybridize to the plus strand of the DNA sequence encoding for the N-terminal consensus sequence of proteins of the present invention. The C-terminal consensus sequence as set forth in SEQ ID NO:143, where $X_1$ is H or E, and $X_2$ is N or Y, is a signature motif shared by proteins of the present invention. Reverse oligonucleotide primers, e.g., SEQ ID NO:128, SEQ ID NO:130, SEQ ID NO:132, and SEQ ID NO:134, can be designed to hybridize to the minus strand of the DNA sequence encoding for the C-terminus consensus sequence of proteins of the present invention. Oligonucleotide primers can be designed to hybridize to plus or minus strands of any one or more of the signature motifs (SEQ ID NOs:31-122, 140 and 141) of the proteins of the present invention.

When combined, forward and reserve primers can be used to amplify nucleotide sequences encoding proteins (or fragments thereof) of the present invention.

Using a Venn diagram (FIG. 2) together with bioassay evidence demonstrating toxin activity, the relationships of the proteins of the present invention are illustrated by common function and insecticidal activity towards Hemipteran and/or Lepidopteran insect species. Table 2 correlates the proteins illustrated in the Venn diagram of FIG. 2 to insect inhibitory activity by insect species. The results from which Table 2 was assembled are described in more detail in the examples.

TABLE 2

Activity profiles of exemplary proteins of the present invention

| Insect | Insect | ['a'] | ['c'] | | | | | | ['b'] | |
|---|---|---|---|---|---|---|---|---|---|---|
| Order | Species | TIC1422 | TIC1886 | TIC1498 | TIC1497 | TIC1415 | TIC1414 | TIC1362 | TIC1922 | TIC1974 |
| Lepidoptera | *H. zea* | | M | | | | | | | |
| | *O. nubilalis* | M/S | | M/S | M/S | S | | | | |
| | *D. saccharalis* | M | | M/S | M/S | | | M/S | | |
| | *D. grandiosella* | M | | M/S | M/S | | | M | | |
| | *A. gemmatalis* | M/S | | M/S | M/S | M/S | M/S | | | |
| Hemiptera | *L. lineolaris* | | M | M/S | M/S* | M/S | M | M | M/S | S |
| | *L. Hesperus* | | M | M/S | M/S* | M | | M/S | | |

M = observed Mortality (compared to buffer control)

S = observed Stunting of survivors (compared to buffer control)

*= N-terminal segment that has been truncated at its C-terminus also demonstrated insect inhibitory activity ['a'], ['b'], and ['c'] are Venn diagram regions depicted in FIG. 2.

In certain embodiments, the pest is specifically an insect pest. Insect pests include insects selected from the orders Coleoptera, Diptera, Hymenoptera, Lepidoptera, Mallophaga, Homoptera, Hemiptera, Blattodea, Orthoptera, Thysanoptera, Dermaptera, Isoptera, Anoplura, Siphonaptera, and Trichoptera. (Note: nematode has been removed per TK's comments)

The insects can include larvae of the order Lepidoptera, such as but not limited to, armyworms, cutworms, loopers, and heliothines in the Family Noctuidae (e.g. fall armyworm (*Spodoptera frugiperda*), beet armyworm (*Spodoptera exigua*), bertha armyworm (*Mamestra configurata*), black cutworm (*Agrotis ipsilon*), cabbage looper (*Trichoplusia ni*), soybean looper (*Pseudoplusia includens*), velvetbean caterpillar (*Anticarsia gemmatalis*), green cloverworm (*Hypena scabra*), tobacco budworm (*Heliothis virescens*), granulate cutworm (*Agrotis subterranea*), armyworm (*Pseudaletia unipuncta*), western cutworm (*Agrotis orthogonia*); borers, casebearers, webworms, coneworms, cabbageworms and skeletonizers from the Family Pyralidae (e.g., European corn borer (*Ostrinia nubilalis*), navel orangeworm (*Amyelois transitella*), corn root webworm (*Crambus caliginosellus*), sod webworm (*Herpetogramma licarsisalis*), sunflower moth (*Homoeosoma electellum*), lesser cornstalk borer (*Elasmopalpus lignosellus*); leafrollers, budworms, seed worms, and fruit worms in the Family Tortricidae (e.g. codling moth (*Cydia pomonella*), grape berry moth (*Endopiza viteana*), oriental fruit moth (*Grapholita molesta*), sunflower bud moth (*Suleima helianthana*); and many other economically important Lepidopteran insects (e.g., diamondback moth (*Plutella xylostella*), pink bollworm (*Pectinophora gossypiella*), gypsy moth (*Lymantria dispar*). Other insect pests of order Lepidoptera include, e.g., *Alabama argillacea* (cotton leaf worm), *Archips argyrospila* (fruit tree leaf roller), *A. rosana* (European leaf roller) and other *Archips* species, *Chilo suppressalis* (Asiatic rice borer, or rice stem borer), *Cnaphalocrocis medinalis* (rice leaf roller), *Crambus caliginosellus* (corn root webworm), *C. teterrellus* (bluegrass webworm), *Diatraea grandiosella* (southwestern corn borer), *D. saccharalis* (surgarcane borer), *Earias insulana* (spiny bollworm), *E. vittella* (spotted bollworm), *Helicoverpa armigera* (American bollworm), *H. zea* (corn earworm or cotton bollworm), *Heliothis virescens* (tobacco budworm), *Herpetogramma licarsisalis* (sod webworm), *Lobesia botrana* (European grape vine moth), *Pectinophora gossypiella* (pink bollworm), *Phyllocnistis citrella* (citrus leafminer), *Pieris brassicae* (large white butterfly), *P. rapae* (imported cabbageworm, or small white butterfly), *Plutella xylostella* (diamondback moth), *Spodoptera exigua* (beet armyworm), *S. litura* (tobacco cutworm, cluster caterpillar), *S. frugiperda* (fall armyworm), and *Tuta absoluta* (tomato leafminer).

The insects can include adults and nymphs of the orders Hemiptera and Homoptera, such as but not limited to, plant bugs from the Family Miridae, cicadas from the Family Cicadidae, leafhoppers (e.g., *Empoasca* spp.) from the Family Cicadellidae, planthoppers from the families Fulgoroidea and Delphacidae, treehoppers from the Family Membracidae, psyllids from the Family Psyllidae, whiteflies from the Family Aleyrodidae, aphids from the Family Aphididae, phylloxera from the Family Phylloxeridae, mealybugs from the Family Pseudococcidae, scales from the families Coccidae, Diaspididae and Margarodidae, lace bugs from the Family Tingidae, stink bugs from the Family Pentatomidae, cinch bugs (e.g., *Blissus* spp.) and other seed bugs from the Family Lygaeidae, spittlebugs from the Family Cercopidae squash bugs from the Family Coreidae, and red bugs and cotton stainers from the Family Pyrrhocoridae. Other pests from the order Hemiptera include *Acrosternum hilare* (green stink bug), *Anasa tristis* (squash bug), *Blissus leucopterus leucopterus* (chinch bug), *Corythuca gossypii* (cotton lace bug), *Cyrtopeltis modesta* (tomato bug), *Dysdercus suturellus* (cotton stainer), *Euschistus servus* (brown stink bug), *Euschistus variolarius* (one-spotted stink bug), *Graptostethus* spp. (complex of seed bugs), *Leptoglossus corculus* (leaf-footed pine seed bug), *Lygus lineolaris* (tarnished plant bug), *Lygus hesperus* (Western tarnish plant bug), *Nezara viridula* (southern green stink bug), *Oebalus pugnax* (rice stink bug), *Oncopeltus fasciatus* (large milkweed bug), and *Pseudatomoscelis seriatus* (cotton fleahopper).

In certain embodiments, the recombinant polypeptide of the present invention exhibits insect inhibitory activity against Lepidopteran species selected from the group consisting of *H. zea, O. nubilalis, D. saccharalis, D. grandiosella, A. gemmatalis, S. frugiperda, S. exigua, A. ipsilon, T. ni, P. includens, H. virescens, P. xylostella, P. gossypiella, H. armigera, E. lignosellus*, and *P. citrella*, and/or against Hemipteran species selected from the group consisting of *L. hesperus, L. lineolaris, A. hilare, E. servus, N. viridula, M. persicae, A. glycines,* and *A. gossypii*.

The proteins of the present invention represent a new category and class of Cry protein, exhibiting no greater than 56% amino acid identity to any other Bt protein known in the art. The protein exhibiting the nearest identity to any of the proteins of the present invention is Cry15Aa1 (GI: 142726, ACCESSION: AAA22333) (Brown and Whiteley, Journal of Bacteriology, January 1992, p. 549-557, Vol. 174, No. 2). Cry15Aa1 was aligned using Clustal W to each protein exemplified in the present invention and the results are shown in Table 3.

TABLE 3

Alignment of proteins to Cry15Aa1.

| Protein | Amino acid identities* with Cry15Aa1 | Percent amino acid identity* with Cry15Aa1 |
|---|---|---|
| TIC1498 (SEQ ID NO: 2) | 159 | 43.1% |
| TIC1415 (SEQ ID NO: 4) | 162 | 42.0% |
| TIC1497 (SEQ ID NO: 6) | 164 | 42.5% |
| TIC1886 (SEQ ID NO: 8) | 163 | 46.3% |
| TIC1925 (SEQ ID NO: 10) | 164 | 42.5% |
| TIC1414 (SEQ ID NO: 12) | 159 | 45.3% |
| TIC1885 (SEQ ID NO: 14) | 159 | 43.2% |
| TIC1922 (SEQ ID NO: 16) | 160 | 41.6% |
| TIC1422 (SEQ ID NO: 18) | 156 | 44.3% |
| TIC1974 (SEQ ID NO: 20) | 156 | 44.3% |
| TIC2032 (SEQ ID NO: 22) | 155 | 40.8% |
| TIC2120 (SEQ ID NO: 24) | 158 | 42.9% |
| TIC1362 (SEQ ID NO: 26) | 194 | 55.3% |
| TIC2335 (SEQ ID NO: 136) | 130 | 38.7% |
| TIC2334 (SEQ ID NO: 138) | 129 | 38.2% |

*in a Clustal W alignment

Cry15Aa1 does not contain any of the signature motifs (SEQ ID NOs:31-122, 140 and 141) shared by the proteins of the present invention. Cry15Aa1 does not exhibit the proteolytic cleavage sites [2], [3], and [4] shared by the proteins of the present invention as shown in FIG. 1. Cry15Aa1 exhibits a calculated isoelectric point of about 7.3 pI, in contrast to the proteins of the present invention which each exhibits a calculated isoelectric point of about 5 to 6 pI. Cry15Aa1 exhibits only 3 positive charges at neutral pH, whereas the proteins of the present invention exhibit calculated from 3 to 10 negative charges at neutral pH.

The proteins of the present invention can be used to produce antibodies that bind specifically to this genus of proteins and can be used to screen for and to find other members of the genus.

Nucleotide sequences encoding these proteins can be used as probes and primers for screening to identify other members of the genus using thermal or isothermal amplification and/or hybridization methods, e.g., oligonucleotides as set forth in SEQ ID NOs:127-134, and oligonucleotides hybridizing to sequence encoding the signature motifs of the present invention. Nucleotide sequence homologs, i.e., insecticidal proteins encoded by nucleotide sequences that hybridize to each or any of the sequences disclosed herein under stringent hybridization conditions, are specifically intended to be included within the scope of the present invention. The present invention also provides a method for detecting a first nucleotide sequence that hybridizes to a second nucleotide sequence, wherein the first nucleotide sequence encodes an insecticidal protein or insecticidal fragment thereof and hybridizes under stringent hybridization conditions to the second nucleotide sequence. In such case the second nucleotide sequence can be any of the sequences disclosed herein under stringent hybridization conditions. Nucleotide coding sequences hybridize to one another under appropriate hybridization conditions and the proteins encoded by these nucleotide sequences cross react with antiserum raised against any one of the other proteins. Stringent hybridization conditions, as defined herein, comprise at least hybridization at 42° C. followed by two washes for five minutes each at room temperature with 2×SSC, 0.1% SDS, followed by two washes for thirty minutes each at 65° C. in 0.5×SSC, 0.1% SDS. Of course, one skilled in the art will recognize that, due to the redundancy of the genetic code, many other sequences are capable of encoding such related proteins, and those sequences, to the extent that they function to express insecticidal proteins either in *Bacillus* strains or in plant cells, are intended to be encompassed by the present invention, recognizing of course that many such redundant coding sequences will not hybridize under these conditions to the native Bt sequences encoding TIC1498, TIC1415, TIC1497, TIC1886, TIC1925, TIC1414, TIC1885, TIC1922, TIC1422, TIC1974, TIC2032, TIC2120, TIC1362, TIC2335, and TIC2334.

In certain embodiments, a recombinant polypeptide exhibiting insect inhibitory activity against a Lepidopteran and/or Hemipteran insect species is within the scope of the present invention, which polypeptide is encoded by a polynucleotide segment that hybridizes under stringent hybridization conditions to one or more of the nucleotide sequences set forth in any of SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:20, SEQ ID NO:23, SEQ ID NO:25, SEQ ID NO:135, or SEQ ID NO:137, or the complement thereof.

An aspect of this invention provides methods for discovering related proteins, and such methods include the sequencing of Bt genomes, assembly of sequence data, the identification and cloning of Bt genes encoding such insect inhibitory proteins, and the expression and testing of new Bt proteins to assay for insect inhibitory activity. Another aspect of this invention employs molecular methods to engineer and clone commercially useful proteins comprising chimeras of proteins and improved variants from the genus of insect inhibitory proteins, e.g., the chimeras can be assembled from segments in each of the various proteins that are within the spaces between the signature motifs to derive improved embodiments. The proteins of the present invention can be subjected to alignment to each other and to other Bt insect inhibitory proteins, and segments of each such protein can be identified that may be useful for substitution between the aligned proteins, resulting in the construction of chimeric proteins. Such chimeric proteins can be subjected to pest bioassay analysis and characterized for the presence of increased bioactivity or expanded target pest spectrum compared to the parent proteins from which each such segment in the chimera was derived. The insect inhibitory activity of the polypeptides can be further engineered for improved activity to a particular pest or to a broader spectrum of pests by swapping domains or segments with other proteins.

One skilled artisan understands the concept of amino acid substitution, and recognizes that this requires experimentation that is not routine, as there are amino acid positions that can accept substitution without apparent affect to the structure or function of the protein; however, in surprising circumstances, even a conservative substitution may be determined to significantly alter the structure or function of the protein, and it is often unknown with precision the positions in the amino acid segments that would accept such changes. Accordingly, amino acid substitutions at positions along the length of the protein sequence that affect function can be identified by alanine scanning mutagenesis, and such positions can often be useful for points of amino acid insertions and/or deletions, or N- or C-terminal deletions. Accordingly, the proteins of the present invention include functionally equivalent fragments (N- or C-terminal deletions) of the proteins represented by the amino acid sequences of the present invention. N-terminal protein fragments (SEQ ID NOs:123-126, 16) of TIC1497 and TIC1922 have demonstrated insect inhibitory activity (Table 2 and Examples 6, 10, and 11, respectively). Corresponding N-terminal protein fragments for any member of the genus is contemplated.

Proteins functionally equivalent (having substantially equivalent insect inhibitory activity) to the proteins of the present invention include proteins with conservative amino acid substitutions in the protein sequences of the present invention. In such amino acid sequences, one or more amino acids in the starting sequence is (are) substituted with another amino acid(s), the charge and polarity of which is similar to that of the native amino acid, i.e., as exemplified herein a conservative amino acid substitution, resulting in a conservative change from the perspective of charge and polarity, but which may result in a change in the bioactivity of the protein, preferably increasing the activity of the protein compared to the starting protein with the original amino acid at such positions, or resulting in a change in the variant protein with reference to the spectrum of biological activity and without any loss of insect inhibitory activity. An example of proteins that can entertain substituted amino acids or terminal deletions to obtain biological equivalents include, but are not limited to, the protein sequence as set forth in any of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, and SEQ ID NOs:123-126.

Enrichment of the proteins of the present invention either in plants or by a process that includes culturing recombinant Bt cells under conditions to express/produce recombinant polypeptide/proteins of the present invention is contemplated. Such a process can include preparation by desiccation, lyophilization, homogenization, extraction, filtration, centrifugation, sedimentation, or concentration of a culture of recombinant *Bacillus thuringiensis* cells expressing/producing said recombinant polypeptide. Such a process can result in a Bt cell extract, cell suspension, cell homogenate, cell lysate, cell supernatant, cell filtrate, or cell pellet. By obtaining the recombinant polypeptides/proteins so produced, a composition that includes the recombinant polypeptides/proteins can include bacterial cells, bacterial spores, and parasporal inclusion bodies and can be formulated for various uses, including agricultural insect inhibitory spray products or as insect inhibitory formulations in diet bioassays.

It is intended that an insect inhibitory composition/formulation comprising the aforementioned recombinant polypeptide/protein is within the scope of the present invention. In certain embodiments, such composition may further comprise at least one pesticidal agent that exhibits insect inhibitory activity against the same Lepidopteran and/or Hemipteran insect species but is different from the recombinant polypeptide. Such agent is selected from the group consisting of an insect inhibitory protein, an insect inhibitory dsRNA molecule, and an ancillary protein. Examples of such agents include, but are not limited to, a TIC807 protein, a TIC853 protein, a AXMI-171 protein, and a Cry51Aa1 protein. Other compositions are contemplated for combining with the proteins of the present invention, and with the combinations of proteins provided above. For example, topically applied pesticidal chemistries that are designed for controlling pests that are also controlled by the proteins of the present invention can be used with the proteins of the present invention in seed treatments, spray on/drip on/or wipe on formulations that can be applied directly to the soil (a soil drench), applied to growing plants expressing the proteins of the present invention, or formulated to be applied to seed containing one or more transgenes encoding one or more of the proteins of the present invention. Such formulations for use in seed treatments can be applied with various stickers and tackifiers known in the art. Such formulations may contain pesticides that are synergistic in mode of action with the proteins of the present invention, meaning that the formulation pesticides act through a different mode of action to control the same or similar pests that are controlled by the proteins of the present invention, or that such pesticides act to control pests within a broader host range, such as lepidopteran or Hemipteran species or other plant pest species such as coleopteran species that are not effectively controlled by the proteins of the present invention.

The aforementioned composition/formulation can further comprise an agriculturally-acceptable carrier, such as a bait, a powder, dust, pellet, granule, spray, emulsion, a colloidal suspension, an aqueous solution, a *Bacillus* spore/crystal preparation, a seed treatment, a recombinant plant cell/plant tissue/seed/plant transformed to express one or more of the proteins, or bacterium transformed to express one or more of the proteins. Depending on the level of insect inhibitory or insecticidal inhibition inherent in the recombinant polypeptide and the level of formulation to be applied to a plant or diet assay, the composition/formulation can include various by weight amounts of the recombinant polypeptide, e.g. from 0.0001% to 0.001% to 0.01% to 1% to 99% by weight of the recombinant polypeptide.

The proteins of the invention can be combined in formulations for topical application to plant surfaces, to the soil, in formulations for seed treatments, in formulations with other agents toxic to the target pests of Hemipteran and Lepidopteran species. Such agents include but are not limited to, a TIC807 protein, a TIC853 protein, a AXMI-171 protein, and a Cry51Aa1 protein which each are effective in controlling the same Hemipteran pests that are controlled by the insect inhibitory proteins of the present invention.

It is also intended that a method of controlling a Lepidopteran and/or Hemipteran species pest is within the scope of the present invention. Such method comprises the steps of contacting the pest with an insect inhibitory amount of the recombinant polypeptide/protein. In certain embodiments, Lepidopteran and Hemipteran species pest is in a crop field.

An embodiment of the invention includes recombinant polynucleotides that encode the insect inhibitory protein members of the genus. With reference to a "recombinant" polynucleotide, it is intended that a polynucleotide molecule is made by human means or intervention through molecular biology engineering techniques, which can include the amplification or replication of such molecules upon introduction into a host cell, and the subsequent extraction and/or purification of the polynucleotide from the representative host cell. Polynucleotide embodiments of the present invention include ribonucleic acids (RNA) and deoxyribonucleic acids (DNA). Proteins of the present invention can be expressed from DNA constructs in which the open reading frame encoding the protein is operably linked to elements such as a promoter and any other regulatory elements functional for expression in that particular system for which the construct is intended. For example, plant-expressible promoters can be operably linked to protein encoding sequences for expression of the protein in plants, and Bt-expressible promoters can be operably linked to the protein encoding sequences for expression of the protein in Bt. Other useful elements that can be operably linked to the protein encoding sequences include, but are not limited to, enhancers, introns, protein immobilization tags (HIS-tag), target sites for post-translational modifying enzymes, dsRNA coding segments, siRNAs, miRNAs, ribosomal binding sites, leader elements, and miRNA target sites.

Exemplary recombinant polynucleotide molecules provided herewith include, but are not limited to, SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, SEQ ID NO:28, SEQ ID NO:29, SEQ ID NO:30, and SEQ ID NO:135.

An aspect of the invention provides a recombinant DNA construct that includes one or more aforementioned polynucleotides, which can additionally be engineered with transcribable or non-transcribable regions or both. Such regions are operably assembled to promote expression of DNA to RNA through either in vivo or in vitro systems, thereby producing the novel RNA transcript embodiments of the present invention. The present invention features RNA transcripts that include, but are not limited to, the protein-encoding RNA and additional RNA regions that are translatable, non-translatable, or both. Such additional RNA regions include translatable regions engineered to translate to terminal or intra-peptide regions, and non-translatable regions engineered to either promote transcription, translation, or both.

In certain embodiments, the aforementioned recombinant DNA construct is in an expression cassette for use in an *E. coli* or Bt expression system. Expression cassettes are typically designed with a promoter at the 5' end of the cassette, upstream of a desired polynucleotide segment encoding a protein of the present invention. A promoter can consist of multiple different promoter elements operably linked to provide for the initiation of transcription of the sequences encoding a protein of the invention. The DNA sequence consisting of the promoter-protein-encoding DNA can be operably linked at its 3' end to a transcriptional termination signal sequence functional in an *E. coli* and/or Bt cell to produce the recombinant DNA construct.

In certain embodiments, the aforementioned recombinant DNA construct is in an expression cassette for expression in plants. Expression cassettes are designed with a promoter at the 5' end of the cassette, upstream of a desired polynucleotide segment encoding a protein of the present invention. 5' untranscribed DNA can comprise a promoter which can consist of multiple different promoter and enhancer elements operably linked to provide for the initiation of transcription of downstream sequences including sequences encoding the polypeptides of the invention. One or more transcribed but non-translated DNA sequence(s) can be operably linked 3' to the promoter in the expression cassette, including leader and/or intron sequence(s). An intron sequence is optionally provided 3' to the leader sequence or in some cases within the open reading frame encoding the desired protein. A polynucleotide segment encoding an optional translocation polypeptide (a signal peptide or a chloroplast transit peptide, for example) may be inserted 5' to the coding sequence of the protein of the present invention for localizing the protein of the invention to a particular subcellular position. The nucleotide sequence encoding the protein of the present invention is optionally operably positioned within the aforementioned expression cassette, along with any requisite operably linked polyadenylation (polyA) and/or transcriptional termination sequence functional in plant cells. The aforementioned elements are arranged contiguously and can be used in various combinations depending on the desired expression outcome.

The present invention features promoters functional in plants including, but not limited to, constitutive, non-constitutive, spatially-specific, temporally-specific, tissue-specific, developmentally-specific, inducible, and viral promoters. Examples of promoters functional in plants include corn sucrose synthetase 1, corn alcohol dehydrogenase 1, corn light harvesting complex, corn heat shock protein, pea small subunit RuBP carboxylase, Ti plasmid mannopine synthase, Ti plasmid nopaline synthase, *petunia* chalcone isomerase, bean glycine rich protein 1, Potato patatin, lectin, CaMV 35S, the S E9 small subunit RuBP carboxylase, carnation etched ring virus, and dahlia mosaic virus promoter.

A recombinant DNA construct comprising the protein encoding sequences can also further comprise a region of DNA that encodes for one or more insect inhibitory agents which can be configured to concomitantly express or co-express with DNA sequence encoding the protein of the present invention, a protein different from the aforementioned protein, an insect inhibitory dsRNA molecule, or an ancillary protein. Ancillary proteins include co-factors, enzymes, binding-partners, or other insect inhibitory agents that function synergistically to aid in the effectiveness of an insect inhibitory agent, for example, by aiding its expression, influencing its stability in plants, optimizing free energy for oligomerization, augmenting its toxicity, and increasing its spectrum of activity.

A recombinant polynucleotide or recombinant DNA construct comprising the protein-coding sequence can be delivered to host cells by vectors. Methods for transferring recombinant DNA constructs to and from host cells, including *E. coli, B. thuringiensis*, and *Agrobacterium* species, are known in the art. Such vectors are designed to promote the uptake of vector DNA and to further provide expression of DNA to RNA to protein in in vitro or in vivo systems, either transiently or stably. Examples of the vectors include, but are not limited to, a plasmid, baculovirus, artificial chromosome, virion, cosmid, phagemid, phage, or viral vector. Such vectors can be used to achieve stable or transient expression of the protein encoding sequence in a host cell; and, if the case may be, subsequent expression to polypeptide. An exogenous recombinant polynucleotide or recombinant DNA construct that comprises the protein encoding sequence and that is introduced into a host cell is also referred to herein as a "transgene".

Plasmids can be designed to replicate in *E. coli* or *B. thuringiensis*, or both. Such plasmids contain genetic elements that allow for the replication and maintenance of such plasmids and for the expression of transgenes, e.g. aforementioned recombinant DNA constructs, in either species.

Plant transformation vectors can be designed to allow for the *Agrobacterium*-mediated transfer of a T-DNA, i.e. transferred DNA comprising aforementioned recombinant DNA constructs. Such plant transformation vectors contain genetic elements that allow for the replication and maintenance of such plasmid vectors in *E. coli* and/or *Agrobacterium* and are essential for transfer of the T-DNA into a plant genome.

Transgenic host cells comprising recombinant DNA constructs encoding toxin proteins of the present invention are also contemplated. A transgenic host cell can be further defined as a prokaryotic host cell, i.e. a bacterial cell, e.g., *Bacillus thuringiensis, Bacillus subtilis, Bacillus megaterium, Bacillus cereus, Bacillus laterosperous, Escherichia, Salmonella, Agrobacterium, Pseudomonas*, or *Rhizobium* cell, or a eukaryotic host cell, e.g., a plant cell, and each of these types of cells is also referred to herein as a microbial cell, a microbe, or a microorganism.

As used herein a "host cell" means a cell that is transformed or transfected with exogenous recombinant DNA, e.g. by electroporation or by *Agrobacterium*-mediated transformation or by bombardment using microparticles coated with recombinant DNA, or by transduction or by plasmid transfer or by other means. A host cell of this invention can be a transformed bacterium, e.g. *E. coli* host cell or Bt host cell or *Agrobacterium* host cell, or a plant host cell.

Accordingly, a host cell of can be an originally-transformed plant cell that exists as a microorganism or as a progeny plant cell that is regenerated into differentiated tissue, e.g., into a transgenic plant with stably-integrated, non-natural recombinant DNA, or seed or pollen derived from a progeny transgenic plant. As used herein a "transgenic plant" includes a plant, plant part, plant cells or seed whose genome has been altered by the stable integration of recombinant DNA. A transgenic plant includes a plant regenerated from an originally-transformed plant cell and progeny transgenic plants from later generations or crosses of a transformed plant. Accordingly, examples of plant parts are leaf, a branch, a bark, a blade, a pollen grain, a stalk, a cell, a stem, a flower, a sepal, a fruit, a root, or a seed.

Transgenic plants expressing the protein(s) of the invention exhibit pest tolerance. Such plants and its cells include alfalfa, banana, barley, bean, berry, *brassica*, broccoli, cabbage, cactus, carrot, cassava, castor, cauliflower, celery, chickpea, Chinese cabbage, citrus, clover, coconut, coffee, corn, cotton, cucumber, cucurbit, Douglas fir, eggplant, *eucalyptus*, flax, fruit, garlic, grape, hops, kapok, leek, legume, lettuce, Loblolly pine, melons, millets, nut, oat, olive, onion, ornamental, palm, pasture grass, pea, peanut, pepper, pigeonpea, pine, poplar, potato, pumpkin, *Radiata* pine, radish, rapeseed, rice, rootstocks, rye, safflower, shrub, sorghum, Southern pine, soybean, spinach, squash, strawberry, succulent, sugar beet, sugarcane, sunflower, sweet corn, sweet gum, sweet potato, switchgrass, tea, tobacco, tomato, tree, triticale, turf grass, vegetable, watermelon, and wheat plants and cells.

Nucleotides sequences can be constructed that are useful for expression of these proteins in plant cells, and such plant cells can be regenerated into transgenic plants that can produce seeds containing such nucleotide sequences which can be commercialized, bred together with other transgenic plants expressing different Bt insect inhibitory proteins or other agents toxic to crop pests.

Plant cells can be transformed by multiple mechanisms that are within the skill of the art including but not limited to bacterial transformation systems such as *Agrobacterium* or *Rhizobacterium*, electroporation, ballistic mediated systems, and the like. Microprojectile bombardment methods are illustrated in U.S. Pat. No. 5,015,580 (soybean); U.S. Pat. No. 5,550,318 (corn); U.S. Pat. No. 5,538,880 (corn); U.S. Pat. No. 5,914,451 (soybean); U.S. Pat. No. 6,160,208 (corn); U.S. Pat. No. 6,399,861 (corn); U.S. Pat. No. 6,153,812 (wheat) and U.S. Pat. No. 6,365,807 (rice) and *Agrobacterium*-mediated transformation is described in U.S. Pat. No. 5,159,135 (cotton); U.S. Pat. No. 5,824,877 (soybean); U.S. Pat. No. 5,463,174 (canola); U.S. Pat. No. 5,591,616 (corn); U.S. Pat. No. 5,846,797 (cotton); U.S. Pat. No. 6,384,301 (soybean), U.S. Pat. No. 7,026,528 (wheat) and U.S. Pat. No. 6,329,571 (rice), US Patent Application Publication 2004/0087030 A1 (cotton), and US Patent Application Publication 2001/0042257 A1 (sugar beet) and in Arencibia et al. (1998) Transgenic Res. 7:213-222 (sugarcane) and other more recent methods described in US Patent Application Publications 2009/0138985A1 (soybean), 2008/0280361A1 (soybean), 2009/0142837A1 (corn), 2008/0282432 (cotton), 2008/0256667 (cotton), 2003/0110531 (wheat), U.S. Pat. No. 5,750,871 (canola), U.S. Pat. No. 7,026,528 (wheat), and U.S. Pat. No. 6,365,807 (rice). Transformation of plant material can be practiced in tissue culture on a nutrient media, e.g., a mixture of nutrients that will allow cells to grow in vitro. Recipient cell targets include, but are not limited to, meristem cells, hypocotyls, calli, immature embryos and gametic cells such as microspores, pollen, sperm and egg cells. Callus may be initiated from tissue sources including, but not limited to, immature embryos, hypocotyls, seedling apical meristems, microspores and the like. Cells containing a transgenic nucleus are grown into transgenic plants.

In addition to direct transformation of a plant material with a recombinant DNA, a transgenic plant cell nucleus can be prepared by crossing a first plant having cells with a transgenic nucleus with recombinant DNA with a second plant lacking the transgenic nucleus. For example, recombinant DNA can be introduced into a nucleus from a first plant line that is amenable to transformation to transgenic nucleus in cells that are grown into a transgenic plant which can be crossed with a second plant line to introgress the recombinant DNA into the second plant line. A transgenic plant with recombinant DNA providing an enhanced trait, e.g., enhanced yield, can be crossed with transgenic plant line having other recombinant DNA that confers another trait, for example herbicide resistance or pest resistance, to produce progeny plants having recombinant DNA that confers both traits. Typically, in such breeding for combining traits the transgenic plant donating the additional trait is a male line and the transgenic plant carrying the base traits is the female line. The progeny of this cross will segregate such that some of the plants will carry the DNA for both parental traits and some will carry DNA for one parental trait; such plants can be identified by markers associated with parental recombinant DNA, e.g., marker identification by analysis for recombinant DNA or, in the case where a selectable marker is linked to the recombinant DNA, by application of the selecting agent such as a herbicide for use with a herbicide tolerance marker, or by selection for the insect inhibitory trait. Progeny plants carrying DNA for both parental traits can be crossed back into the female parent line multiple times, for example usually 6 to 8 generations, to produce a progeny plant with substantially the same genotype as one original transgenic parental line but for the recombinant DNA of the other transgenic parental line.

In the practice of plant transformation, exogenous DNA is typically introduced into only a small percentage of target plant cells in any one transformation experiment. Cells of this invention can be directly tested to confirm stable integration of the exogenous DNA by a variety of well-known DNA detection methods or by a variety of well-known bioactivity assays that test for insect inhibitory activity (further described in the examples section). Marker genes can be used to provide an efficient system for identification of those cells that are stably transformed by receiving and integrating a recombinant DNA molecule into their genomes. Preferred marker genes provide selective markers which confer resistance to a selective agent, such as an antibiotic or an herbicide. Any of the herbicides to which plants of this invention can be made resistant can be used as agents for selective markers. Potentially transformed cells are exposed to the selective agent. In the population of surviving cells will be those cells where, generally, the resistance-conferring gene is integrated and expressed at sufficient levels to permit cell survival. Cells may be tested further to confirm stable integration of the exogenous DNA. Commonly used selective marker genes include those conferring resistance to antibiotics such as kanamycin and paromomycin (nptII), hygromycin B (aph IV), spectinomycin (aadA) and gentamycin (aac3 and aacC4) or resistance to herbicides such as glufosinate (bar or pat), dicamba (DMO) and glyphosate (aroA or EPSPS). Examples of such selectable markers are illustrated in U.S. Pat. Nos. 5,550,318, 5,633,435, 5,780,708, and 6,118,047. Markers which provide an ability to visually screen transformants can also be employed, for example, a gene expressing a colored or fluorescent protein such as a luciferase or green fluorescent protein (GFP).

Plant cells that survive exposure to the selective agent, or plant cells that have been scored positive in a screening assay, may be cultured in regeneration media and allowed to mature into plants. Developing plants regenerated from transformed plant cells can be transferred to plant growth mix, and hardened off, for example, in an environmentally controlled chamber at about 85% relative humidity, 600 ppm $CO_2$, and 25 to 250 microeinsteins m 2 s−1 of light, prior to transfer to a greenhouse or growth chamber for maturation. These growth conditions vary among plant species and are known to those skilled in the art. Plants are regenerated from about 6 weeks to 10 months after a transformant is identified, depending on the initial tissue, and plant species. Plants may be pollinated using conventional plant breeding methods known to those of skill in the art and seed produced, for example self-pollination is commonly used with transgenic corn. The regenerated transformed plant or its progeny seed or plants can be tested for expression of the recombinant DNA and selected for the presence of insect inhibitory activity.

Transgenic plants encoding and expressing one or more of the proteins of the present invention are grown to (i) generate transgenic plants having an enhanced trait as compared to a control plant and (ii) produce transgenic seed and haploid pollen of this invention. Such plants with enhanced traits are identified by selection of transformed plants or progeny seed for the enhanced trait. For efficiency a selection method is designed to evaluate multiple transgenic plants (events) comprising the recombinant DNA, for example multiple plants from 2 to 20 or more transgenic events. Transgenic plants grown from transgenic seed provided herein demonstrate improved agronomic traits that contribute to increased insect inhibitory tolerance or increased harvest yield or other traits that provide increased plant value, including, for example, improved seed or boll quality. Of particular interest are cotton, alfalfa, corn, soy, or sugarcane plants having enhanced insect inhibitory resistance against one or more insects of the orders Lepidoptera and/or Hemiptera. Of particular interest are cotton plants having enhanced insect inhibitory resistance against an insect of the order Hemiptera.

The invention provides methods to produce a plant and harvest a crop from seed comprising a recombinant polynucleotide molecule encoding the insect inhibitory polypeptides of the present invention. Of particular interest are cotton, alfalfa, corn, soy, or sugarcane plants having enhanced insect inhibitory resistance against an insect(s) of the order Lepidoptera and/or Hemiptera. The method includes the steps of crossing an insect resistant plant expressing the recombinant polypeptides of the present invention with another plant, obtaining at least one progeny plant derived from this cross, and selecting progeny that expresses the recombinant polypeptides of the present invention wherein said progeny is resistant against an insect. This includes the steps of planting the seed, producing a crop from plants grown from the seed, and harvesting the crop, wherein at least 50% of the crop comprises seed comprising the recombinant polynucleotide molecule.

In an aspect of the invention, a transgenic plant cell, a transgenic plant, and transgenic plant parts comprising a recombinant polynucleotide (i.e. transgene) that expresses any one or more of the protein encoding sequences are provided herein. It is intended that "bacterial cell" or "bacterium" can include, but are not limited to, an *Agrobacterium*, a *Bacillus*, an *Escherichia*, a *Salmonella*, a *Pseudomonas*, or a *Rhizobium* cell. It is intended that "plant cell" or "plant" include an alfalfa, banana, barley, bean, broccoli, cabbage, *brassica*, carrot, cassava, castor, cauliflower, celery, chickpea, Chinese cabbage, citrus, coconut, coffee, corn, clover, cotton, a cucurbit, cucumber, Douglas fir, eggplant, *eucalyptus*, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, *Radiata* pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat plant cell or plant. In certain embodiments, transgenic plants and transgenic plant parts regenerated from a transgenic plant cell are provided. In certain embodiments, the transgenic plants can be obtained from a transgenic seed. In certain embodiments, transgenic plant parts can be obtained by cutting, snapping, grinding or otherwise disassociating the part from the plant. In certain embodiments, the plant part can be a seed, a boll, a leaf, a flower, a stem, a root, or any portion thereof. In certain embodiments, a transgenic plant part provided herein is a non-regenerable portion of a transgenic plant part. As used in this context, a "non-regenerable" portion of a transgenic plant part is a portion that cannot be induced to form a whole plant or that cannot be induced to form a whole plant that is capable of sexual and/or asexual reproduction. In certain embodiments, a non-regenerable portion of a plant part is a portion of a transgenic seed, boll, leaf, flower, stem, or root.

Also provided herein are methods of making transgenic plants that comprise insect inhibitory amounts of the protein(s) of the present invention. Such plants can be made by introducing a recombinant polynucleotide that encodes any of the proteins provided herein into a plant cell, and selecting a plant derived from said plant cell that expresses an insect inhibitory amount of the proteins. Plants can be derived from the plant cells by regeneration, seed, pollen, or meristem transformation techniques.

Also provided herein is the use of a transgenic plant that expresses an insect inhibitory amount of one or more of the proteins of the present invention to control a Lepidopteran and/or a Hemipteran species pest. Any of the aforementioned transgenic plants can be used in methods for protecting a plant from insect infestation provided herein.

Also provided herein is the use of any of the aforementioned transgenic host cells to produce the proteins of the present invention.

Additional aspects of the invention include methods and/or kits for detecting DNA, RNA, or protein of the present invention, methods for identifying members of the genus of proteins described herein, methods for identifying novel proteins related to genus family members, methods for testing for control of insect growth and/or infestation, and methods for providing such control to plants and other recipient hosts. These proteins can be used to produce antibodies that bind specifically to this class/genus of protein and these antibodies can be used to screen and find other members of the genus. An antibody by itself, or in a mixture of antibodies, that binds specifically to a target of the recombinant polypeptides of the present invention is contemplated; and, the method of using this antibody by itself, or in a mixture of antibodies, to detect or quantify proteins sharing epitopes of the proteins of the present invention is also contemplated. Such a method to detect or quantify can include the steps of contacting a sample with the antibody and using detection means well known in the art to detect the binding of antibody to polypeptide target in the sample. Where one or more epitopes are contemplated and their combination used in such a method, the binding of an antibody or mixture of antibodies recognizing different epitopes can identify a polypeptide exhibiting homology to the recombinant polypeptides of the present invention.

Kits for detecting the presence of a polypeptide target in a sample suspected of containing the polypeptide target are provided. Such kits would include a reagent(s) used for epitope detection and a control reagent(s) to show that the detection was operating within statistical variances. Reagent storage, instructions for detection means and use of reagents, and additional parts and tools that can be included in such kits are contemplated.

The polynucleotide segments encoding the proteins of the present invention, i.e. the proteins of the described genus, particularly the segments derived from wild type Bt strains, can be used as probes and primers for screening for and identifying other members within the genus using thermal amplification and/or hybridization methods. Nucleotide probes or primers can vary in length, sequence, concentration, backbone, and formulation depending on the sample detection method used. The present invention features primers and probes that can be used to detect and isolate homologous genes that encode for insect inhibitory protein members of the genus. A DNA detection kit is contemplated providing a skilled artisan to more easily perform the detection and/or isolation of homologous genes of the present invention. The invention provides for use of such kits and methods and for novel genes and the insect inhibitory polypeptides encoded by such genes that are detected and isolated by the aforementioned detection means.

The invention further provides for methods of testing the polypeptides of the present invention for insect inhibitory activity, herein termed "bioassay". Described herein are qualitative insect bioassays that measure growth inhibition, mortality, or a combination of both. The insect orders tested in the following examples include Coleoptera, Diptera, Lepidoptera, and Hemiptera. The diet recipe and preparation, the preparation of test and control samples, the insect preparation, and the procedures for conducting assays are typically dependent upon the type and size of the insect and/or pest being subjected to any particular evaluation. Such methods are illustrated and described in detail in the following examples.

In certain embodiments, plant product can comprise commodity or other products of commerce derived from a transgenic plant or transgenic plant part, where the commodity or other products can be tracked through commerce by detecting nucleotide segments or expressed RNA or proteins that encode or comprise distinguishing portions of the proteins of the present invention. Such commodity or other products of commerce include, but are not limited to, plant parts, biomass, oil, meal, sugar, animal feed, flour, flakes, bran, lint, processed seed, and seed.

Also provided herewith are processed plant products that comprise a detectable amount of a recombinant nucleotide encoding any one of the proteins of the present invention, an insect inhibitory fragment thereof, or any distinguishing portion thereof. In certain embodiments, the processed product is selected from the group consisting of plant biomass, oil, meal, animal feed, flour, flakes, bran, lint, hulls, and processed seed. In certain embodiments, the processed product is non-regenerable. In certain embodiments, a distinguishing portion thereof can comprise any polynucleotide encoding at least 20, 30, 50 or 100 amino acids of the amino acid sequence of SEQ ID NO:2, 4, 6, 8, 10, 12, 14, 16, 18, 20, 22, 24, 26, 136 or 138.

Also provided herein are methods of controlling insects. Such methods can comprise growing a plant comprising an insect inhibitory amount of the protein of the present invention. In certain embodiments, such methods can further comprise any one or more of: (i) applying any composition comprising or encoding the proteins of the present invention to the plant or a seed that gives rise to the plant; and/or (ii) transforming the plant or a plant cell that gives rise to the plant with a polynucleotide encoding the proteins of the present invention. In certain embodiments, the plant is a transiently or stably transformed transgenic plant comprising a transgene that expresses an insect inhibitory amount of the protein of the present invention. In certain embodiments, the plant is a non-transgenic plant to which a composition comprising the protein of the present invention has been applied.

Other features and advantages of the invention will be apparent from the following detailed description, examples, and claims.

EXAMPLES

In view of the foregoing, those of skill in the art should appreciate that changes can be made in the specific aspects which are disclosed and still obtain a like or similar result without departing from the spirit and scope of the invention. Thus, specific details disclosed herein are not to be interpreted as limiting.

Example 1: Discovery of Insect Inhibitory Proteins

Various Bt strains exhibiting distinctive attributes, e.g. inferred toxicity, proteomic diversity, and morphological variations when compared to each other, were identified, and DNA was obtained from each such strain and prepared for DNA sequencing. DNA sequence information was generated for each such strain, raw sequence reads were processed, contigs were assembled from processed reads, open reading frames were identified, and deduced amino acid sequences were analyzed.

Example 2: Cloning and Expressing Insect Inhibitory Proteins

This example illustrates the cloning of polynucleotide segments encoding insect inhibitory proteins, and insertion into and expression in recombinant host cells.

Nucleotide segments were obtained by amplification from corresponding genomic samples from which each open reading frame was identified in Example 1. Amplified nucleotide segments were inserted into a recombinant plasmid and transformed into an acrystalliferous Bt host cell or into an *E. coli* expression strain, and the resulting recombinant strain(s) were observed to express a recombinant protein.

Recombinant proteins exemplified herein were observed to exhibit insect inhibitory properties to a variety of pest species as described in Examples 3-13 below. Nucleotide sequences as set forth in SEQ ID NO:1, SEQ ID NO:3, SEQ ID NO:5, SEQ ID NO:7, SEQ ID NO:11, SEQ ID NO:15, SEQ ID NO:17, SEQ ID NO:19, SEQ ID NO:25, SEQ ID NO:135, and SEQ ID NO:137 were confirmed to encode proteins having amino acid sequences as set forth in SEQ ID NO:2, SEQ ID NO:4, SEQ ID NO:6, SEQ ID NO:8, SEQ ID NO:12, SEQ ID NO:16, SEQ ID NO:18, SEQ ID NO:20, SEQ ID NO:26, SEQ ID NO:136, and SEQ ID NO:138 (respectively, TIC1498, TIC1415, TIC1497, TIC1886, TIC1414, TIC1922, TIC1422, TIC1974, TIC1362, TIC2335, and TIC2334).

Recombinant plasmids and strains were also constructed to contain polynucleotide segments having the sequences as set forth in SEQ ID NO:9, SEQ ID NO:13, SEQ ID NO:21, and SEQ ID NO:23, and were confirmed to encode proteins having amino acid sequences as set forth in SEQ ID NO:10, SEQ ID NO:14, SEQ ID NO:22, and SEQ ID NO:24 (respectively, TIC1925, TIC1885, TIC2032, and TIC2120).

Example 3: Lepidopteran Activity of TIC1886

This example illustrates the *Helicoverpa zea* (Hz) activity exhibited by a sample from a recombinant strain expressing recombinant protein TIC1886 having deduced amino acid sequence of SEQ ID NO:8.

A diet of 16.5% (w/v) of "Multiple Species" diet (Southland Products, 201 Stuart Island Road, Lake Village, Ark. 71653) was prepared in a 14% (w/v) agar base (Serva #11393). The agar base was melted and blended with diet and purified water to volume (1.4% (w/v) agar). Diet suspension was dispensed into individual bioassay compartments.

A test sample of recombinant protein TIC1886 was prepared as described in example 2, and overlaid over 24 compartmentalized diet surfaces approximating about 2890 ug/mL per compartment. A buffer control sample was overlaid onto 96 compartmentalized diet surfaces. Together, 120 compartmentalized diet surfaces comprise the test set of this example prepared for *Helicoverpa zea* bioassay.

A single neonate larva was transferred to the diet surface of each individual compartment of the test set of this example (120 total neonates) and each compartment sealed with a ventilated cover. The test-set was placed in a controlled environment at 27° C. and 60% RH with no light for 5-7 days and scored for mortality and stunting. Stunting was visually estimated in comparison to untreated insects and was scored as significantly stunted (>67% stunting), moderately stunted (33-67% stunted), or stunted (<33%).

No stunting or mortality was observed with buffer control samples. Mortality was observed against 24 Hz larvae at 2890 ug/mL TIC1886. It was concluded that the protein TIC1886 demonstrated *Helicoverpa zea* (corn earworm) activity (see FIG. 2 and Table 2).

The lepidopteran bioassay procedure described in this example was also applied to a combination of larvae from *Ostrinia nubilalis, Diatraea saccharalis, Diatraea grandiosella*, and *Anticarsia gemmatalis* species using the proteins of the present invention (from Example 2, TIC1498, TIC1415, TIC1497, TIC1414, TIC1422, and TIC1362), and the results are described in examples 4-7.

Example 4: Lepidopteran Activity of TIC1498, TIC1497, and TIC1422

Using the methods and bioassay techniques described in Example 3, recombinant proteins TIC1498 (SEQ ID NO:2), TIC1497 (SEQ ID NOs:6), and TIC1422 (SEQ ID NO:18) were tested against neonates of *Ostrinia nubilalis* (On), *Diatraea* saccharalis (Ds), *Diatraea grandiosella* (Dg), and *Anticarsia gemmatalis* (Ag) insect species.

TIC1498 exhibited mortality against *Ostrinia nubilalis*, and survivors were significantly stunted, over 24 larvae at 2500 ug/mL. TIC1497 exhibited mortality against *Ostrinia nubilalis*, and survivors were significantly stunted, over 24 larvae at 3700 ug/mL. TIC1422 exhibited mortality against *Ostrinia nubilalis*, and survivors were significantly stunted, over 24 larvae at 1300 ug/mL. It was concluded that TIC1498, TIC1497, and TIC1422 demonstrated activity (see FIG. 2 and Table 2) against *Ostrinia nubilalis* (European corn borer).

TIC1498 exhibited mortality against *Diatraea saccharalis*, and survivors were significantly stunted, over 24 larvae at 3000 ug/mL. TIC1497 exhibited mortality against *Diatraea saccharalis*, and survivors were significantly stunted, over 24 larvae at 2000 ug/mL. TIC1422 exhibited 100% mortality to *Diatraea saccharalis*, over 24 larvae at 300 ug/mL. It was concluded that recombinant proteins TIC1498, TIC1497, and TIC1422 demonstrated activity (see FIG. 2 and Table 2) against *Diatraea saccharalis* (surgarcane borer).

TIC1498 exhibited mortality against *Diatraea grandiosella*, and survivors were moderately stunted, over 24 larvae at 3000 ug/mL. TIC1497 exhibited mortality rate against *Diatraea grandiosella*, and survivors were significantly stunted, over 24 larvae at 2000 ug/mL. TIC1422 exhibited mortality against *Diatraea grandiosella*, over 24 larvae at 300 ug/mL. It was concluded that TIC1498, TIC1497, and TIC1422 demonstrated activity (see FIG. 2 and Table 2) against *Diatraea grandiosella* (southwestern corn borer).

TIC1498 exhibited mortality against *Anticarsia gemmatalis*, and survivors were significantly stunted, over 48 larvae at 2500-3000 ug/mL. TIC1497 exhibited mortality against *Anticarsia gemmatalis*, and survivors were moderately to significantly stunted, over 48 larvae at 2000-3700 ug/mL. TIC1422 exhibited mortality against *Anticarsia gemmatalis*, and survivors were significantly stunted, over 48 larvae at 300-1300 ug/mL. It was concluded that TIC1498, TIC1497, and TIC1422 demonstrated activity (see FIG. 2 and Table 2) against *Anticarsia gemmatalis* (velvetbean caterpillar).

Example 5: Lepidopteran Activity of TIC1415

TIC1415 (SEQ ID NO:4) was tested against *Ostrinia nubilalis* (On) and *Anticarsia gemmatalis* (Ag) insect species neonates. TIC1415 exhibited mortality against *Ostrinia nubilalis*, and survivors were moderately stunted, over 24 larvae at 1500 ug/mL. It was concluded that TIC1415 demonstrated activity (see FIG. 2 and Table 2) against *Ostrinia nubilalis* (European corn borer).

TIC1415 exhibited mortality against *Anticarsia gemmatalis*, and survivors were moderately stunted, over 24 larvae at 1500 ug/mL. It was concluded that TIC1415 demonstrated activity (see FIG. 2 and Table 2) against *Anticarsia gemmatalis* (velvetbean caterpillar).

Example 6: Lepidopteran Activity of TIC1414

TIC1414 (SEQ ID NO:12) was tested against *Anticarsia gemmatalis* (Ag) insect species neonates. TIC1414 exhibited mortality against *Anticarsia gemmatalis*, and survivors were stunted, over 24 larvae at 870 ug/mL. It was concluded that TIC1414 demonstrated activity (see FIG. 2 and Table 2) against *Anticarsia gemmatalis* (velvetbean caterpillar).

Example 7: Lepidopteran Activity of TIC1362

TIC1362 (SEQ ID NO:26) was tested against *Diatraea saccharalis* (Ds) and *Diatraea grandiosella* (Dg) insect species neonates. TIC1362 exhibited mortality against *Diatraea* saccharalis, and survivors were significantly stunted, over 24 larvae at 400 ug/mL. TIC1362 demonstrated *Diatraea saccharalis* (velvetbean caterpillar) activity (see FIG. 2 and Table 2).

TIC1362 exhibited 100% mortality against *Diatraea grandiosella* over 24 larvae at 400 ug/mL. TIC1362 demonstrated *Diatraea grandiosella* (southwestern corn borer) activity (see FIG. 2 and Table 2).

Example 8: Hemipteran Activity of TIC1498

This example illustrates insect inhibitory activity of TIC1498 (SEQ ID NO:2) when provided in the diet of hemipteran insects, including but not limited to members of the Heteroptera miridae, including the genus *Lygus*, e.g., *Lygus hesperus* and *Lygus lineolaris*. This example more specifically illustrates the *Lygus hesperus* (Lh) and *Lygus lineolaris* (Ll) activity exhibited by a sample from a recombinant strain expressing the recombinant protein TIC1498.

A diet of 7.81% (w/v) of "*Lygus* Diet" diet (Bio-Serv #F9644B, One 8th Street, Suite One, Frenchtown, N.J. 08825) and liquid contents of two whole fresh eggs was prepared. The diet was cooled and stored under moisture controlled conditions and at 4° C. until ready for use. This diet preparation was used within 2 days of preparation.

Test samples containing TIC1498 protein were prepared encapsulated (~40 uL) between stretched Parafilm and Mylar sheets that were heat-sealed (sachets).

*Lygus hesperus* and *Lygus lineolaris* eggs were incubated at 24° C. until they reached between 0 to about 12 hours pre-hatch stage. Pre-hatch eggs were soaked and rinsed in sterile water, then placed in confined proximity to the prepared sachets in a controlled environment at 24° C. and 60% RH with no light for 4-7 days and scored for percent mortality and stunting of any survivors. Stunting was visually estimated in comparison to untreated insects and was scored as significantly stunted (>67% stunting), moderately stunted (33-67% stunted), or stunted (<33%).

At 10 ug/mL TIC1498, mortality was observed against *Lygus lineolaris*, and survivors stunted, over 24 neonate nymphs. At 50 ug/mL TIC1498, mortality was observed against *Lygus lineolaris*, and survivors stunted, over 24 neonate nymphs. TIC1498 exhibited mortality against *Lygus lineolaris* at 100 ug/mL, and survivors were moderately stunted, over 24 neonate nymphs.

At 10 ug/mL TIC1498, mortality was observed against *Lygus hesperus*, and survivors stunted, over 24 neonate nymphs. At 50 ug/mL TIC1498, mortality was observed against *Lygus hesperus*, and survivors stunted, over 24 neonate nymphs. TIC1498 exhibited mortality against *Lygus hesperus* at 100 ug/mL, and survivors were moderately stunted, over 24 neonate nymphs. At 2300 ug/mL TIC1498, 100% mortality was observed against *Lygus hesperus*, over 24 neonate nymphs.

TIC1498 demonstrated both *Lygus lineolaris* (tarnished plant bug) and *Lygus hesperus* (Western tarnish plant bug) activity (see FIG. 2 and Table 2). The hemipteran bioassay procedure described in this example was also performed using TIC1415, TIC1497, TIC1886, TIC1414, TIC1922, TIC1974, and TIC1362.

Example 9: Hemipteran Activity of TIC1922 and TIC1974

TIC1922 (SEQ ID NO:16) and TIC1974 (SEQ ID NO:20) were tested against *Lygus lineolaris* (Ll). TIC1922 was tested in 3 groups of 24 sachets, and exhibited mortality against *Lygus lineolaris*, and survivors exhibited stunting at 3000 ug/mL. TIC1974 did not exhibit mortality against *Lygus lineolaris*, but survivors were stunted, in an evaluation of 24 neonate nymphs at 3000 ug/mL. TIC1922 and TIC1974 demonstrated *Lygus lineolaris* (tarnished plant bug) activity (see FIG. 2 and Table 2).

Example 10: Hemipteran Activity of TIC1497

TIC1497 (SEQ ID NO:6) was tested against *Lygus hesperus* (Lh). TIC1497 exhibited mortality against *Lygus hesperus*, and survivors were moderately stunted, in an experiment evaluating 48 neonate nymphs at 2000 ug/mL.

Preparations of TIC1497 fragments were made by treating TIC1497 with thermolysin, chymotrypsin, trypsin, or Glu-C, resulting in TIC1497 fragments exhibiting masses of 32411 Da (SEQ ID NO:64), 32557 Da (SEQ ID NO:62), 34225 Da (SEQ ID NO:61), and 34485 Da (SEQ ID NO:63). The protein eluate from the thermolysin treated preparation was isolated (TIC1497.32411) on an ion exchange column and used in bioassays against Hemipteran species.

TIC1497.32411 exhibited mortality against *Lygus lineolaris*, and survivors were moderately stunted, in an experiment using 24 neonate nymphs at 100 ug/mL. TIC1497.32411 exhibited 100% mortality at a dose of 1000 ug/mL.

TIC1497.32411 exhibited mortality against *Lygus lineolaris*, and survivors were moderately stunted, in an experiment using 24 neonate nymphs at a dose of 2300 ug/mL.

TIC1497 demonstrated *Lygus hesperus* (Western tarnish plant bug) activity (see FIG. 2 and Table 2). The fragment TIC1497.32411 demonstrated both *Lygus lineolaris* (tarnished plant bug) and *Lygus hesperus* (Western tarnish plant bug) activity (see FIG. 2 and Table 2).

Example 11: Hemipteran Activity of TIC1886, TIC1415, TIC1414, and TIC1362

TIC1886 (SEQ ID NO:8), TIC1415 (SEQ ID NO:4), TIC1414 (SEQ ID NO:12), and TIC1362 (SEQ ID NO:24) were tested against *Lygus lineolaris* and *Lygus hesperus*. TIC1886 exhibited mortality against both *Lygus lineolaris* and *Lygus hesperus*, at a dose equivalent to 124 ug/mL. TIC1415 exhibited mortality against *Lygus lineolaris* and *Lygus hesperus* at a dose equivalent to 150 ug/mL and survivors were stunted. TIC1414 exhibited mortality against *Lygus lineolaris* at a dose equivalent to 95 ug/mL. TIC1362 exhibited mortality against *Lygus lineolaris* at a dose equivalent to 370 ug/mL.

TIC1886, TIC1415, and TIC1362 demonstrated both *Lygus lineolaris* (tarnished plant bug) and *Lygus hesperus* (Western tarnish plant bug) activity. TIC1414 demonstrated *Lygus lineolaris* (tarnished plant bug) activity (see FIG. 2 and Table 2)

Example 12: Insect Inhibitory Activities of Other Protein Members

Other protein members from the genus of the present invention, such as but not limited to TIC1925 (SEQ ID NO:10), TIC1885 (SEQ ID NO:14), TIC2032 (SEQ ID NO:22), and TIC2120 (SEQ ID NO:24), are prepared for bioassay against pests of plants, including a pest from the phylum Nematoda, a pest from Lepidoptera, and a pest from Hemiptera.

Example 13: Protein Expression in Plants

This example illustrates expression of proteins of the present invention in plants. Polynucleotide segments for use in expression of the proteins of the present invention in plants can be produced according to the methods set forth in U.S. Pat. No. 7,741,118. For example, toxin proteins having the amino acid sequence as set forth in SEQ ID NO:4, SEQ ID NO:12, SEQ ID NO:18, and SEQ ID NO:26 can be produced in plants from polynucleotide segments having the sequence as set forth respectively in SEQ ID NO:27, SEQ ID NO:28, SEQ ID NO:29, and SEQ ID NO:30. Polynucleotide segments designed for use in plants and encoding the proteins of the present invention, including the sequences as set forth in SEQ ID NO:27, SEQ ID NO:28, SEQ ID NO:29, and SEQ ID NO:30 are operably linked to the requisite expression elements for expression in plants, and transformed into the genome of plant cells, preferably cotton, alfalfa, corn, and soybean cells.

It is intended that polynucleotide segments (or polynucleotide molecules) encoding each of the following enumerated proteins, insect inhibitory fragments thereof, and proteins exhibiting the degree of identity specified herein above to one or more of these enumerated proteins, be used alone or in combinations with each other, or in combinations with other toxin proteins or toxic agents such as dsRNA mediated gene suppression molecules designed to work in synergistic or synonymous ways with the proteins of the present invention, to achieve plants and plant cells protected from pest infestation, particularly insect pest infestation. The specific enumerated proteins within the scope of the invention include TIC1498 (SEQ ID NO:2), TIC1415 (SEQ ID NO:4), TIC1497 (SEQ ID NO:6), TIC1886 (SEQ ID NO:8), TIC1925 (SEQ ID NO:10), TIC1414 (SEQ ID NO:12), TIC1885 (SEQ ID NO:14), TIC1922 (SEQ ID NO:16), TIC1422 (SEQ ID NO:18), TIC1974 (SEQ ID NO:20), TIC2032 (SEQ ID NO:22), TIC2120 (SEQ ID NO:24), TIC1362 (SEQ ID NO:26), TIC2335 (SEQ ID NO:136), TIC2334 (SEQ ID NO:138) and insect inhibitory fragments thereof, such as but not limited to, TIC1497.34225 (SEQ ID NO:61), TIC1497.32557 (SEQ ID NO:62), TIC1497.34485 (SEQ ID NO:63), and TIC1497.32411 (SEQ ID NO:64).

For instance, proteins of the TIC1415 genus of the present invention can be combined with other pesticidal agents, including pesticidal agents targeting pests which overlap with pests targeted by TIC1415 proteins. Additionally, other pesticidal agents may include agents that target pests that do not overlap with pests targeted by TIC1415 proteins. In either case, it is intended that TIC1415 proteins be used alone or combined with other pesticidal agents. In the examples described below, TIC1415 was co-expressed with a TIC807 toxin protein in cotton plants and in planta bioassays were conducted. In addition to TIC807 toxin proteins, other pesticidal agents that can be used in combination with TIC1415 proteins include (1) hemipteran-centric agents, e.g. dsRNA directed towards hemipteran orthologs of *Nilaparvata lugens* V-ATPase-E, 21E01 (Li, Re et al., 2011, Pest Manag Sci); dsRNA directed towards hemipteran orthologs of five different genes—actin ortholog, ADP/ATP translocase, α-tubulin, ribosomal protein L9 (RPL9) and V-ATPase A subunit (Upadhyay, S. K., et al., 2011, J. Biosci. 36(1), p. 153-161); AXMI-171 (US20100298207A1); Bt endotoxins such as Cry3A, Cry4Aa, Cry11Aa, and Cyt1Aa, which were found to exhibit low to moderate toxicity on the pea aphid, *Acyrthosiphon pisum*, in terms of both mortality and growth rate (Porcar, M. et al., Applied and Environmental Microbiology, July 2009, p. 4897-4900, Vol. 75, No. 14); (2) other Coleopteran pesticidal agents, e.g. DIG11 and DIG5; Cry7; eCry3.1Ab; mCry3A; Cry8; Cry34/Cry35; and Cry3 toxins generally; and (3) other Lepidopteran pesticidal agents, e.g. DIG2; Cry1 toxins; Cry1A.105; Cry2 toxins, particularly Cry2A toxins; Cry1F toxins; VIP3 toxins; and Cry9 toxins. Transgenic crop events expressing other pesticidal agents can also be used in combination with crop events expressing TIC1415 proteins, examples of which include MON88017, MON89034, MON863, MON15985, MON531, MON757, COT102, TC1507, DAS59122-7, 3006-210-23, 281-24-236, T304-40, GHB119, COT67B, MIR162; corn event 5307, and the like. Such combinations with events expressing one or more proteins of the TIC1415 genus proteins provide more durable pest protection, provide a resistance management strategy for target pest control, and reduce farmer inputs, saving considerable expense in time and monetary value.

Recombinant plants are generated from transformed plant cells of this example, and the recombinant plants or their progeny are evaluated for resistance to pest infestation, such as tolerance to Hemiptera and/or Lepidoptera. Transgenic plants and seed are selected that provide pest resistance, such as to Hemiptera and Lepidoptera, and such plants and seed are advanced for further development.

Example 14: In-Planta Bioassay of TIC1415

In this study, toxin protein TIC1415 having the amino acid sequence as set forth in SEQ ID NO:4 was produced in plants from polynucleotide segments having the sequence as set forth in SEQ ID NO:27. DNA having the sequence of SEQ ID NO:27 encoding TIC1415 was cloned into an *Agrobacterium*-mediated plant transformation vector along with requisite promoter and regulatory elements for transformation and expression in cotton cells. Transgenic cotton plants (recombinant cotton plants) were produced and tested for efficacy. Regenerated (R0) transgenic plants were transferred to soil and tissue samples selected from transformation events that were low in copy number and expressing TIC1415 protein. Lyophilized tissue samples of R0 plants from three events were weighed and combined 1:50 and 1:100 (weight:buffer) of 25 mM Sodium-carb/bicarb buffered at pH 10.5 to extract soluble protein from the tissue. Samples were confirmed by Western blot for presence of TIC1415 protein. Sample extracts were fed to *Lygus lineolaris* using the bioactivity assay described in Example 8. Extract from DP393 cotton tissue absent of TIC1415 protein was also prepared as negative control. Sample extracts from all three events exhibited mortality against *Lygus lineolaris* and survivors were stunted. Mortality and stunting scores were significant compared to bioactivity scores of insects fed with sample extracts from the DP393 negative control.

R0 plants were grown and self-pollinated to obtain seed homozygous for the introduced transgenic DNA. Homozygous plants from three different single copy events were selected and five seed per event planted and evaluated in a whole plant caging assay. Plants were grown to flowering stage and each whole cotton plant was enclosed in a mesh cage made from perforated plastic. Two pairs of male and female *Lygus hesperus* adults were placed into each cage and allowed to reproduce. Resulting insect progeny were allowed to infest the caged cotton plants for 3 weeks. At the end of the 21 day period, *Lygus* insects at various stages of development were counted and average means calculated on a per plant basis. Plants from all three events had significantly less insects compared to the DP393 negative control. See Table 4.

TABLE 4

In-planta bioassay of TIC1415.

| Event | Mean 3rd Instar or < | Mean 4th Instar Nymphs | Mean 5th Instar Nymphs | Mean Live 2nd Gen. Adults | Mean Total 2nd Gen. Lygus | Students t Grouping (p < 0.05) |
|---|---|---|---|---|---|---|
| 84 | 0.20 | 0.00 | 0.60 | 0.00 | 0.80 | B |
| 52 | 0.00 | 0.40 | 1.60 | 1.20 | 3.20 | B |
| 39 | 0.40 | 0.40 | 2.00 | 1.60 | 4.40 | B |
| DP393 (negative) | 3.60 | 5.20 | 9.70 | 9.50 | 28.0 | A |

Mean $2^{nd}$ Generation *Lygus* Recovered from Five Cotton Plants per Event in a Caged Whole Plant Assay. Events with the same letter do not have statistically different $2^{nd}$ generation *Lygus* numbers (p < 0.05, Students t).

Example 15: Protein Bioassay of TIC1415 and a TIC807 Hemipteran Toxic Protein

Protein samples were prepared containing various mixtures of TIC1415 and a TIC807 hemipteran toxic protein and tested in bioassay. TIC1415 protein alone and the TIC807 protein alone were also prepared as positive controls. Buffer was used as negative control. Sample mixtures were fed to *Lygus lineolaris* using bioactivity assay. All three preparations containing toxin protein exhibited mortality against *Lygus lineolaris* and survivors were stunted. Mortality and stunting scores were significant compared to bioactivity scores of insects fed with buffer (see Table 5). The data suggests that there are no antagonistic effects. Additional bioassay tests are performed on mixtures to demonstrate synergistic and/or additive effects.

TABLE 5

| Bioassay data for protein mix: TIC1415 combined with a TIC807 toxin protein | | | | | | |
|---|---|---|---|---|---|---|
| SAMPLE | TIC1415 (ug/mL) | TIC807 (ug/mL) | Mean† Population mortality | T Grouping on mort | Mean† stunting‡ score | T Grouping on stunting |
| TIC1415 + TIC807 | 4.35 | 1 | 21.79 | AB* | 0.60 | AB* |
| TIC1415 + TIC807 | 2.175 | 1 | 20.36 | B* | 0.60 | AB* |
| TIC1415 + TIC807 | 1.0875 | 1 | 12.50 | BC | 0.60 | AB* |
| TIC1415 + TIC807 | 4.35 | 0.5 | 32.50 | A* | 0.80 | A* |
| TIC1415 + TIC807 | 1.75 | 0.265 | 7.86 | CD | 0.40 | ABC |
| TIC1415 + TIC807 | 0.875 | 0.265 | 0.00 | D | 0.00 | C |
| TIC1415 + TIC807 | 0.4375 | 0.265 | 5.36 | CD | 0.00 | C |
| TIC1415 + TIC807 | 4.35 | 0.25 | 13.21 | BC | 0.40 | ABC |
| TIC1415 + TIC807 | 1.75 | 0.1325 | 0.00 | D | 0.00 | C |
| TIC1415 + TIC807 | 1.75 | 0.06625 | 0.00 | D | 0.00 | C |
| TIC1415 | 4.35 | 0 | 12.50 | BC | 0.40 | ABC |
| TIC1415 | 1.75 | 0 | 7.86 | CD | 0.00 | C |
| TIC807 | 0 | 1 | 0.00 | D | 0.20 | BC |
| TIC807 | 0 | 0.265 | 2.50 | CD | 0.00 | C |
| Buffer (negative) control | 0 | 0 | 0.00 | D | 0.00 | C |

†Average (mean) of 5 populations of 8 nymphs per population.
‡Stunting scores correspond to visual mass ratings where 0 = no difference to negative control, 1 = about 25% less mass, 2 = about 50% less mass, and 3 = about 75% less mass. The average of the stunting scores for each population of eight nymphs is reported.
*At 95% confidence interval.

Example 16: In-Planta Bioassay of TIC1415 and TIC807

Transgenic cotton events were designed to co-express respective proteins TIC1415 (SEQ ID NO:4) and a TIC807 protein. Such plants were evaluated in a caged whole plant assay infested with *Lygus lineolaris*. Five plants each from ten events were caged and infested with 2 pairs of male and female *L. lineolaris* per plant. The assay was incubated in a growth chamber under normal environmental conditions for cotton plant development for 21 days. DP393 negative control plants were grown in similar manner. At the end of the 3 week period, *Lygus* of various stages of development were counted. The mean number per plant of *Lygus hesperus* insects at each stage in development were calculated and the results are shown in Table 6. Therein, different plant-expressible promoters were used to drive expression of the transcript encoding TIC1415 in the respective constructs 12 and 13.

TABLE 6

| In-planta data for protein mix: TIC1415 combined with a TIC807 protein toxin | | | | | | | | | | |
|---|---|---|---|---|---|---|---|---|---|---|
| Construct | Event | N | Mean 3rd Instar or < | Mean 4th Instar Nymphs | Mean 5th Instar Nymphs | Mean Live 2nd Gen. Adults | Mean Total 2nd Gen. *Lygus* | SEM | Tukey Grouping |
| 12 | 021 | 5 | 0.00 | 0.00 | 0.00 | 0.00 | 0.00 | 0.00 | B |
| | 625 | 5 | 0.20 | 0.20 | 0.20 | 0.00 | 0.60 | 0.24 | B |
| | 830 | 5 | 2.20 | 0.20 | 0.00 | 0.00 | 2.40 | 1.12 | AB |
| | 890 | 5 | 4.40 | 0.00 | 0.20 | 0.00 | 4.60 | 2.62 | AB |
| | 521 | 5 | 4.60 | 0.60 | 0.00 | 0.00 | 5.20 | 4.27 | AB |
| | 980 | 5 | 3.40 | 1.20 | 1.20 | 0.00 | 5.80 | 4.86 | AB |
| 13 | 426 | 5 | 0.00 | 0.00 | 0.00 | 0.00 | 0.00 | 0.00 | B |
| | 611 | 5 | 0.60 | 0.00 | 0.00 | 0.00 | 0.60 | 0.60 | B |
| | 999 | 5 | 0.40 | 0.00 | 0.40 | 0.00 | 0.80 | 0.37 | B |
| | 356 | 5 | 6.20 | 0.00 | 0.40 | 0.00 | 6.60 | 4.73 | AB |
| Inbred | DP393 (Negative) | 10 | 7.00 | 2.50 | 0.80 | 0.00 | 10.30 | 3.75 | A |

Mean 2nd Generation *Lygus* Recovered from Five Cotton Plants per Event in a Caged Whole Plant Assay. Events with the same letter do not have statistically different 2nd generation *Lygus* numbers ($p < 0.05$, Students t).

SEQUENCE LISTING

<160> NUMBER OF SEQ ID NOS: 134

<210> SEQ ID NO 1
<211> LENGTH: 1110
<212> TYPE: DNA
<213> ORGANISM: Artificial Sequence
<220> FEATURE:
<223> OTHER INFORMATION: tic1498
<220> FEATURE:
<223> OTHER INFORMATION: recombinant polynucleotide encoding a TIC1498
    protein.

<400> SEQUENCE: 1

```
atggcaatta taaatcaatc atcactaaat tcaagaatac acgatttact tgaagattca        60
agagaagctt ttgatatatt ctacagagat cgacctggag gtttcaatgg aagaatccct       120
ggacgtgaac aacttgataa ttatcaacta actaatgtaa atgttagtcc taggaatcaa       180
gatttccaaa cgattcctag gttacaacac actgctacac aagtaattga aaataacaca       240
agtgtaacac aatctcaaac cgtttctttc aatgaaagaa caacagacac ttttacaaca       300
tcggttacta cgggatttaa aactggaact agtgtgaaat ctacgacaaa attcaaaata       360
tctgttggat ttttagcagc aggcgaatta gaacaatcag tggaagttgc tgttaatttt       420
gagtataatt atagttcaac aactacagag acgcatagtg ttgaaagagg atgggtcatt       480
acacagccta taattgctcc tccacgaaca agggtagaag ctactcttct aatttatgct       540
ggttctgttg atgtaccaat tgatttaaat gctaccattg ttggtgatcc aattccctgg       600
caagattggg gtccatcagt atatacagcc tctttcctcg acgggaataa tttggggtgg       660
tcgggtttta tacgaccaga tgaactatca ttggcatctt cggcatatag acctgttgga       720
agaacagcaa tttttagcgg tttagcgact accaatgttg cctccggcct atattctatt       780
gttcgtattg atgaaaggcc tttaccagga tttacagggg aaacaaggcg ttattattta       840
ccgccttcat tagctactcc agatcaaata ctttcgacaa atacgttcgg aaataatgtg       900
ccaattatta atccagttcc taatgcacat tgcaaaaaag aacattctcc aattattatt       960
cataaaaata gagaagagaa gtgtgaacgc gattatgatg aagtgtatcc tcgtcataat      1020
caagtagaga agtgtgaaca caattatgat gaagtgtatc ctcgtcataa tcaagtagag      1080
aagtgcgaac acaattatga tgaagaataa                                       1110
```

<210> SEQ ID NO 2
<211> LENGTH: 369
<212> TYPE: PRT
<213> ORGANISM: Artificial Sequence
<220> FEATURE:
<223> OTHER INFORMATION: TIC1498
<220> FEATURE:
<223> OTHER INFORMATION: an amino acid sequence translation of NT
    positions 1 through 1107 of SEQ ID NO: 1.

<400> SEQUENCE: 2

```
Met Ala Ile Ile Asn Gln Ser Ser Leu Asn Ser Arg Ile His Asp Leu
1               5                   10                  15

Leu Glu Asp Ser Arg Glu Ala Phe Asp Ile Phe Tyr Arg Asp Arg Pro
            20                  25                  30

Gly Gly Phe Asn Gly Arg Ile Pro Gly Arg Glu Gln Leu Asp Asn Tyr
        35                  40                  45

Gln Leu Thr Asn Val Asn Val Ser Pro Arg Asn Gln Asp Phe Gln Thr
    50                  55                  60
```

```
Ile Pro Arg Leu Gln His Thr Ala Thr Gln Val Ile Glu Asn Asn Thr
65                  70                  75                  80

Ser Val Thr Gln Ser Gln Thr Val Ser Phe Asn Glu Arg Thr Thr Asp
                85                  90                  95

Thr Phe Thr Thr Ser Val Thr Thr Gly Phe Lys Thr Gly Thr Ser Val
            100                 105                 110

Lys Ser Thr Thr Lys Phe Lys Ile Ser Val Gly Phe Leu Ala Ala Gly
        115                 120                 125

Glu Leu Glu Gln Ser Val Glu Val Ala Val Asn Phe Glu Tyr Asn Tyr
    130                 135                 140

Ser Ser Thr Thr Thr Glu Thr His Ser Val Glu Arg Gly Trp Val Ile
145                 150                 155                 160

Thr Gln Pro Ile Ile Ala Pro Pro Arg Thr Arg Val Glu Ala Thr Leu
                165                 170                 175

Leu Ile Tyr Ala Gly Ser Val Asp Val Pro Ile Asp Leu Asn Ala Thr
            180                 185                 190

Ile Val Gly Asp Pro Ile Pro Trp Gln Asp Trp Gly Pro Ser Val Tyr
        195                 200                 205

Thr Ala Ser Phe Leu Asp Gly Asn Asn Leu Gly Trp Ser Gly Phe Ile
    210                 215                 220

Arg Pro Asp Glu Leu Ser Leu Ala Ser Ser Ala Tyr Arg Pro Val Gly
225                 230                 235                 240

Arg Thr Ala Ile Phe Ser Gly Leu Ala Thr Thr Asn Val Ala Ser Gly
                245                 250                 255

Leu Tyr Ser Ile Val Arg Ile Asp Glu Arg Pro Leu Pro Gly Phe Thr
            260                 265                 270

Gly Glu Thr Arg Arg Tyr Tyr Leu Pro Pro Ser Leu Ala Thr Pro Asp
        275                 280                 285

Gln Ile Leu Ser Thr Asn Thr Phe Gly Asn Asn Val Pro Ile Ile Asn
    290                 295                 300

Pro Val Pro Asn Ala His Cys Lys Lys Glu His Ser Pro Ile Ile Ile
305                 310                 315                 320

His Lys Asn Arg Glu Glu Lys Cys Glu Arg Asp Tyr Asp Glu Val Tyr
                325                 330                 335

Pro Arg His Asn Gln Val Glu Lys Cys Glu His Asn Tyr Asp Glu Val
            340                 345                 350

Tyr Pro Arg His Asn Gln Val Glu Lys Cys Glu His Asn Tyr Asp Glu
        355                 360                 365

Glu
```

<210> SEQ ID NO 3
<211> LENGTH: 1161
<212> TYPE: DNA
<213> ORGANISM: Artificial Sequence
<220> FEATURE:
<223> OTHER INFORMATION: tic1415
<220> FEATURE:
<223> OTHER INFORMATION: a recombinant polynucleotide encoding a TIC1415
    protein.

<400> SEQUENCE: 3
atggcaatta taaatcaatc atcactaaat tcaagaatac acgatttact tgaagattca        60
agagaagctt ttgatatatt ctacagagat cgacctggag gtttcaatgg aagaatccct       120
ggacgtgaac aacttgataa ttatcaacta actaatgtaa atgttagtcc taggaatcaa       180
gatttccaaa cgattcctag gttacaacac actgctacac aagtaattga aaataacaca       240

-continued

| | |
|---|---|
| agtgtaacac aatctcaaac cgtttctttc aatgaaagaa caacagacac ttttacaaca | 300 |
| tcggttacta cgggatttaa aactggaact agtgtgaaat ctacgacaaa attcaaaata | 360 |
| tctgttggat ttttagcagc aggcgaatta gaacaatcag tggaagttgc tgttaatttt | 420 |
| gagtataatt atagttcaac aactacagag acgcatagtg ttgaaagagg atgggtcatt | 480 |
| acacagccta taattgctcc tccacgaaca agggtagaag ctactcttct aatttatgct | 540 |
| ggttctgttg atgtaccaat tgatttaaat gctaccattg ttggtgatcc aattccctgg | 600 |
| caagattggg gtccatcagt atatacagcc tctttcctcg acgggaataa tttggggtgg | 660 |
| tcgggtttta tacgaccaga tgaactatca ttggcatctt cggcatatag acctgttgga | 720 |
| agaacagcaa ttttttagcgg tttagcgact accaatgttg cctccggcct atattctatt | 780 |
| gttcgtattg atgaaaggcc tttaccagga tttacagggg aaacaaggcg ttattattta | 840 |
| ccgccttcat tagctactcc agatcaaata ctttcgacaa atacgttcgg aaataatgtg | 900 |
| ccaattatta atccagttcc taatgcacat tgcaaaaaag aacattctcc aattattatt | 960 |
| cataaaaata gagaagagaa gtgtgaacgc gattatgatg aagtgtatcc tcgtcataat | 1020 |
| caagtagaga agtgtgaaca caattatgat gaagtgtatc ctcgtcataa tcaagtagag | 1080 |
| aagtgtgaac gcgattatga tgaagtgtat cctcgtcata atcaagtaga gaagtgcgaa | 1140 |
| cacaattatg atgaagaata a | 1161 |

<210> SEQ ID NO 4
<211> LENGTH: 386
<212> TYPE: PRT
<213> ORGANISM: Artificial Sequence
<220> FEATURE:
<223> OTHER INFORMATION: TIC1415
<220> FEATURE:
<223> OTHER INFORMATION: an amino acid sequence translation of NT
      positions 1 through 1158 of SEQ ID NO: 3.

<400> SEQUENCE: 4

Met Ala Ile Ile Asn Gln Ser Ser Leu Asn Ser Arg Ile His Asp Leu
1               5                   10                  15

Leu Glu Asp Ser Arg Glu Ala Phe Asp Ile Phe Tyr Arg Asp Arg Pro
            20                  25                  30

Gly Gly Phe Asn Gly Arg Ile Pro Gly Arg Glu Gln Leu Asp Asn Tyr
        35                  40                  45

Gln Leu Thr Asn Val Asn Val Ser Pro Arg Asn Gln Asp Phe Gln Thr
    50                  55                  60

Ile Pro Arg Leu Gln His Thr Ala Thr Gln Val Ile Glu Asn Asn Thr
65                  70                  75                  80

Ser Val Thr Gln Ser Gln Thr Val Ser Phe Asn Glu Arg Thr Thr Asp
                85                  90                  95

Thr Phe Thr Thr Ser Val Thr Gly Phe Lys Thr Gly Thr Ser Val
            100                 105                 110

Lys Ser Thr Thr Lys Phe Lys Ile Ser Val Gly Phe Leu Ala Ala Gly
        115                 120                 125

Glu Leu Glu Gln Ser Val Glu Val Ala Val Asn Phe Glu Tyr Asn Tyr
    130                 135                 140

Ser Ser Thr Thr Thr Glu Thr His Ser Val Glu Arg Gly Trp Val Ile
145                 150                 155                 160

Thr Gln Pro Ile Ile Ala Pro Pro Arg Thr Arg Val Glu Ala Thr Leu
                165                 170                 175

Leu Ile Tyr Ala Gly Ser Val Asp Val Pro Ile Asp Leu Asn Ala Thr
            180                 185                 190

Ile Val Gly Asp Pro Ile Pro Trp Gln Asp Trp Gly Pro Ser Val Tyr
        195                 200                 205

Thr Ala Ser Phe Leu Asp Gly Asn Asn Leu Gly Trp Ser Gly Phe Ile
        210                 215                 220

Arg Pro Asp Glu Leu Ser Leu Ala Ser Ser Ala Tyr Arg Pro Val Gly
225                 230                 235                 240

Arg Thr Ala Ile Phe Ser Gly Leu Ala Thr Thr Asn Val Ala Ser Gly
                245                 250                 255

Leu Tyr Ser Ile Val Arg Ile Asp Glu Arg Pro Leu Pro Gly Phe Thr
            260                 265                 270

Gly Glu Thr Arg Arg Tyr Tyr Leu Pro Pro Ser Leu Ala Thr Pro Asp
        275                 280                 285

Gln Ile Leu Ser Thr Asn Thr Phe Gly Asn Asn Val Pro Ile Ile Asn
        290                 295                 300

Pro Val Pro Asn Ala His Cys Lys Lys Glu His Ser Pro Ile Ile Ile
305                 310                 315                 320

His Lys Asn Arg Glu Glu Lys Cys Glu Arg Asp Tyr Asp Glu Val Tyr
                325                 330                 335

Pro Arg His Asn Gln Val Glu Lys Cys Glu His Asn Tyr Asp Glu Val
            340                 345                 350

Tyr Pro Arg His Asn Gln Val Glu Lys Cys Glu Arg Asp Tyr Asp Glu
        355                 360                 365

Val Tyr Pro Arg His Asn Gln Val Glu Lys Cys Glu His Asn Tyr Asp
    370                 375                 380

Glu Glu
385

<210> SEQ ID NO 5
<211> LENGTH: 1161
<212> TYPE: DNA
<213> ORGANISM: Artificial Sequence
<220> FEATURE:
<223> OTHER INFORMATION: tic1497
<220> FEATURE:
<223> OTHER INFORMATION: a recombinant polynucleotide encoding a TIC1497
    protein.

<400> SEQUENCE: 5
atggcaatta taaatcaatc atcactaaat tcaagaatac acgatttact tgaagattca      60
agagaagctt ttgatatatt ctacagagat cgacctggag gtttcaatgg aagaatccct     120
ggacgtgaac aacttgataa ttatcaacta actaatgtaa atgttagtcc taggaatcaa     180
gatttccaaa cgattcctag gttacaacac actgctacac aagtaattga aaataacaca     240
agtgtaacac aatctcaaac cgtttctttc aatgaaagaa caacagacac ttttacaaca     300
tcggttacta cgggatttaa aactggaact agtgtgaaat ctacgacaaa attcaaaata     360
tctgttggat ttttagcagc aggcgaatta gaacaatcag tggaagttgc tgttaatttt     420
gagtataatt atagttcaac aactacgagg acgcatagtg ttgaaagagg atgggtcatt     480
acacagccta taattgctcc tccacgaaca agggtagaag ctactcttct aatttatgct     540
ggttctgttg atgtaccaat tgatttaaat gctaccattg ttggtgatcc aattccctgg     600
caagattggg gtccatcagt atatacagcc tctttcctcg acgggaataa tttggggtgg     660
tcgggtttta tacgaccaga tgaactatca ttggcatctt cggcatatag acctgttgga     720

```
agaacagcaa ttttagcgg tttagcgact accaatgttg cctccggcct atattctatt    780
gttcgtattg atgaaaggcc tttaccagga tttacagggg aaacaaggcg ttattattta    840
ccgccttcat tagctactcc agatcaaata ctttcgacaa atacgttcgg aaataatgtg    900
ccaattatta atccagttcc taatgcacat tgcaaaaaag aacattctcc aattattatt    960
cataaaaata gagaagagaa gtacgaacgc gattatgatg aagtgtatcc tcgtcataat   1020
caagtagaga agtgtgaaca caattatgat gaagtgtatc ctcgtcataa tcaagtagag   1080
aagtgtgaac gcgattatga tgaagtgtat cctcgtcata atcaagtaga gaagtacgaa   1140
cacaattatg atgaagaata a                                             1161

<210> SEQ ID NO 6
<211> LENGTH: 386
<212> TYPE: PRT
<213> ORGANISM: Artificial Sequence
<220> FEATURE:
<223> OTHER INFORMATION: TIC1497
<220> FEATURE:
<223> OTHER INFORMATION: an amino acid sequence translation of NT
      positions 1 through 1158 of SEQ ID NO: 5.

<400> SEQUENCE: 6

Met Ala Ile Ile Asn Gln Ser Ser Leu Asn Ser Arg Ile His Asp Leu
1               5                   10                  15

Leu Glu Asp Ser Arg Glu Ala Phe Asp Ile Phe Tyr Arg Asp Arg Pro
                20                  25                  30

Gly Gly Phe Asn Gly Arg Ile Pro Gly Arg Glu Gln Leu Asp Asn Tyr
            35                  40                  45

Gln Leu Thr Asn Val Asn Val Ser Pro Arg Asn Gln Asp Phe Gln Thr
        50                  55                  60

Ile Pro Arg Leu Gln His Thr Ala Thr Gln Val Ile Glu Asn Asn Thr
65                  70                  75                  80

Ser Val Thr Gln Ser Gln Thr Val Ser Phe Asn Glu Arg Thr Thr Asp
                85                  90                  95

Thr Phe Thr Thr Ser Val Thr Thr Gly Phe Lys Thr Gly Thr Ser Val
            100                 105                 110

Lys Ser Thr Thr Lys Phe Lys Ile Ser Val Gly Phe Leu Ala Ala Gly
        115                 120                 125

Glu Leu Glu Gln Ser Val Glu Val Ala Val Asn Phe Glu Tyr Asn Tyr
    130                 135                 140

Ser Ser Thr Thr Thr Glu Thr His Ser Val Glu Arg Gly Trp Val Ile
145                 150                 155                 160

Thr Gln Pro Ile Ile Ala Pro Pro Arg Thr Arg Val Glu Ala Thr Leu
                165                 170                 175

Leu Ile Tyr Ala Gly Ser Val Asp Val Pro Ile Asp Leu Asn Ala Thr
            180                 185                 190

Ile Val Gly Asp Pro Ile Pro Trp Gln Asp Trp Gly Pro Ser Val Tyr
        195                 200                 205

Thr Ala Ser Phe Leu Asp Gly Asn Asn Leu Gly Trp Ser Gly Phe Ile
    210                 215                 220

Arg Pro Asp Glu Leu Ser Leu Ala Ser Ser Ala Tyr Arg Pro Val Gly
225                 230                 235                 240

Arg Thr Ala Ile Phe Ser Gly Leu Ala Thr Thr Asn Val Ala Ser Gly
                245                 250                 255

Leu Tyr Ser Ile Val Arg Ile Asp Glu Arg Pro Leu Pro Gly Phe Thr
            260                 265                 270
```

| | | | | | | | | | | | | |
|---|---|---|---|---|---|---|---|---|---|---|---|---|
|Gly|Glu|Thr|Arg|Arg|Tyr|Tyr|Leu|Pro|Pro|Ser|Leu|Ala|Thr|Pro|Asp|
| | |275| | | |280| | | |285| | | | | |

Gly Glu Thr Arg Arg Tyr Tyr Leu Pro Pro Ser Leu Ala Thr Pro Asp
              275                 280              285

Gln Ile Leu Ser Thr Asn Thr Phe Gly Asn Asn Val Pro Ile Ile Asn
    290                 295                 300

Pro Val Pro Asn Ala His Cys Lys Lys Glu His Ser Pro Ile Ile Ile
305                 310                 315                 320

His Lys Asn Arg Glu Glu Lys Tyr Glu Arg Asp Tyr Asp Glu Val Tyr
                325                 330                 335

Pro Arg His Asn Gln Val Glu Lys Cys Glu His Asn Tyr Asp Glu Val
            340                 345                 350

Tyr Pro Arg His Asn Gln Val Glu Lys Cys Glu Arg Asp Tyr Asp Glu
        355                 360                 365

Val Tyr Pro Arg His Asn Gln Val Glu Lys Tyr Glu His Asn Tyr Asp
    370                 375                 380

Glu Glu
385

<210> SEQ ID NO 7
<211> LENGTH: 1059
<212> TYPE: DNA
<213> ORGANISM: Artificial Sequence
<220> FEATURE:
<223> OTHER INFORMATION: tic1886
<220> FEATURE:
<223> OTHER INFORMATION: a recombinant polynucleotide encoding a TIC1886
      protein.

<400> SEQUENCE: 7

```
atggcaatta taaatcaatc atcactaaat tcaagaatac acgatttact tgaagattca      60
agagaagctt ttgatatatt ctacagagat cgacctggag gtttcaatgg aagaatccct     120
ggacgtgaac aacttgataa ttatcaacta actaatgtaa atgttagtcc taggaatcaa     180
gatttccaaa cgattcctag gttacaacac actgctacac aagtaattga aaataacaca     240
agtgtaacac aatctcaaac cgtttctttc aatgaaagaa caacagacac ttttacaaca     300
tcggttacta cgggatttaa aactggaact agtgtgaaat ctacgacaaa attcaaaata     360
tctgttggat ttttagcagc aggcgaatta gaacaatcag tggaagttgc tgttaatttt     420
gagtataatt atagttcaac aactacagag acgcatagtg ttgaaagagg atgggtcatt     480
acacagccta taattgctcc tccacgaaca agggtagaag ctactcttct aatttatgct     540
ggttctgttg atgtaccaat tgatttaaat gctaccattg ttggtgatcc aattccctgg     600
caagattggg gtccatcagt atatacagcc tctttcctcg acgggaataa tttggggtgg     660
tcgggtttta tacgaccaga tgaactatca ttggcatctt cggcatatag acctgttgga     720
agaacagcaa ttttttagcgg tttagcgact accaatgttg cctccggcct atattctatt     780
gttcgtattg atgaaaggcc tttaccagga tttacagggg aaacaaggcg ttattattta     840
ccgccttcat tagctactcc agatcaaata ctttcgacaa atacgttcgg aaataatgtg     900
ccaattatta atccagttcc taatgcacat tgcaaaaaag aacattctcc aattattatt     960
cataaaaata gagaagagaa gtgtgaacgc aattatgatg aagtgtatcc tcgtcataat    1020
caagtagaga agtacgaaca caattatgat gaagaataa                           1059
```

<210> SEQ ID NO 8
<211> LENGTH: 352
<212> TYPE: PRT
<213> ORGANISM: Artificial Sequence
<220> FEATURE:
<223> OTHER INFORMATION: TIC1886
<220> FEATURE:
<223> OTHER INFORMATION: an amino acid sequence translation of NT
    positions 1 through 1056 of SEQ ID NO: 7.

<400> SEQUENCE: 8

Met Ala Ile Ile Asn Gln Ser Ser Leu Asn Ser Arg Ile His Asp Leu
1               5                   10                  15

Leu Glu Asp Ser Arg Glu Ala Phe Asp Ile Phe Tyr Arg Asp Arg Pro
            20                  25                  30

Gly Gly Phe Asn Gly Arg Ile Pro Gly Arg Glu Gln Leu Asp Asn Tyr
        35                  40                  45

Gln Leu Thr Asn Val Asn Val Ser Pro Arg Asn Gln Asp Phe Gln Thr
    50                  55                  60

Ile Pro Arg Leu Gln His Thr Ala Thr Gln Val Ile Glu Asn Asn Thr
65                  70                  75                  80

Ser Val Thr Gln Ser Gln Thr Val Ser Phe Asn Glu Arg Thr Thr Asp
                85                  90                  95

Thr Phe Thr Thr Ser Val Thr Thr Gly Phe Lys Thr Gly Thr Ser Val
            100                 105                 110

Lys Ser Thr Thr Lys Phe Lys Ile Ser Val Gly Phe Leu Ala Ala Gly
        115                 120                 125

Glu Leu Glu Gln Ser Val Glu Val Ala Val Asn Phe Glu Tyr Asn Tyr
    130                 135                 140

Ser Ser Thr Thr Thr Glu Thr His Ser Val Glu Arg Gly Trp Val Ile
145                 150                 155                 160

Thr Gln Pro Ile Ile Ala Pro Pro Arg Thr Arg Val Glu Ala Thr Leu
                165                 170                 175

Leu Ile Tyr Ala Gly Ser Val Asp Val Pro Ile Asp Leu Asn Ala Thr
            180                 185                 190

Ile Val Gly Asp Pro Ile Pro Trp Gln Asp Trp Gly Pro Ser Val Tyr
        195                 200                 205

Thr Ala Ser Phe Leu Asp Gly Asn Asn Leu Gly Trp Ser Gly Phe Ile
    210                 215                 220

Arg Pro Asp Glu Leu Ser Leu Ala Ser Ser Ala Tyr Arg Pro Val Gly
225                 230                 235                 240

Arg Thr Ala Ile Phe Ser Gly Leu Ala Thr Thr Asn Val Ala Ser Gly
                245                 250                 255

Leu Tyr Ser Ile Val Arg Ile Asp Glu Arg Pro Leu Pro Gly Phe Thr
            260                 265                 270

Gly Glu Thr Arg Arg Tyr Tyr Leu Pro Pro Ser Leu Ala Thr Pro Asp
        275                 280                 285

Gln Ile Leu Ser Thr Asn Thr Phe Gly Asn Asn Val Pro Ile Ile Asn
    290                 295                 300

Pro Val Pro Asn Ala His Cys Lys Lys Glu His Ser Pro Ile Ile Ile
305                 310                 315                 320

His Lys Asn Arg Glu Glu Lys Cys Glu Arg Asn Tyr Asp Glu Val Tyr
                325                 330                 335

Pro Arg His Asn Gln Val Glu Lys Tyr Glu His Asn Tyr Asp Glu Glu
            340                 345                 350

<210> SEQ ID NO 9
<211> LENGTH: 1161
<212> TYPE: DNA
<213> ORGANISM: Artificial Sequence
<220> FEATURE:
<223> OTHER INFORMATION: tic1925
<220> FEATURE:
<223> OTHER INFORMATION: a recombinant polynucleotide encoding a TIC1925 protein.

<400> SEQUENCE: 9

| | | |
|---|---|---|
| atggcaatta taaatcaatc atcactaaat tcaagaatac acgatttact tgaagattca | 60 |
| agagaagctt tgatatatt ctacagagat cgacctggag gtttcaatgg aagaatccct | 120 |
| ggacgtgaac aacttgataa ttatcaacta actaatgtaa atgttagtcc taggaatcaa | 180 |
| gatttccaaa cgattcctag gttacaacac actgctacac aagtaattga aaataacaca | 240 |
| agtgtaacac aatctcaaac cgtttctttc aatgaaagaa caacagacac ttttacaaca | 300 |
| tcggttacta cgggatttaa aactggaact agtgtgaaat ctacgacaaa attcaaaata | 360 |
| tctgttggat ttttagcagc aggcgaatta gaacaatcag tggaagttgc tgttaatttt | 420 |
| gagtataatt atagttcaac aactacagag acgcatagtg ttgaaagagg atgggtcatt | 480 |
| acacagccta taattgctcc tccacgaaca agggtagaag ctactcttct aatttatgct | 540 |
| ggttctgttg atgtaccaat tgatttaaat gctaccattg ttggtgatcc aattccctgg | 600 |
| caagattggg gtccatcagt atatacagcc tctttcctcg acgggaataa tttggggtgg | 660 |
| tcgggtttta tacgaccaga tgaactatca ttggcatctt cggcatatag acctgttgga | 720 |
| agaacagcaa ttttagcgg tttagcgact accaatgttg cctccggcct atattctatt | 780 |
| gttcgtattg atgaaaggcc tttaccagga tttacagggg aaacaaggcg ttattattta | 840 |
| ccgccttcat tagctactcc agatcaaata ctttcgacaa atacgttcgg aaataatgtg | 900 |
| ccaattatta atccagttcc taatgcacat tgcaaaaaag aacattctcc aattattatt | 960 |
| cataaaaata gagaagagaa gtgtgaacgc gattatgatg aagtgtatcc tcgtcataat | 1020 |
| caagtagaga agtgtgaaca caattatgat gaagtgtatc ctcgtcataa tcaagtagag | 1080 |
| aagtgtgaac gcgattatga tgaagtgtat cctcgtcata tcaagtagaa gaagtacgaa | 1140 |
| cacaattatg atgaagaata a | 1161 |

<210> SEQ ID NO 10
<211> LENGTH: 386
<212> TYPE: PRT
<213> ORGANISM: Artificial Sequence
<220> FEATURE:
<223> OTHER INFORMATION: TIC1925
<220> FEATURE:
<223> OTHER INFORMATION: an amino acid sequence translation of NT positions 1 through 1158 of SEQ ID NO: 9.

<400> SEQUENCE: 10

```
Met Ala Ile Ile Asn Gln Ser Ser Leu Asn Ser Arg Ile His Asp Leu
1               5                   10                  15

Leu Glu Asp Ser Arg Glu Ala Phe Asp Ile Phe Tyr Arg Asp Arg Pro
            20                  25                  30

Gly Gly Phe Asn Gly Arg Ile Pro Gly Arg Glu Gln Leu Asp Asn Tyr
        35                  40                  45

Gln Leu Thr Asn Val Asn Val Ser Pro Arg Asn Gln Asp Phe Gln Thr
    50                  55                  60

Ile Pro Arg Leu Gln His Thr Ala Thr Gln Val Ile Glu Asn Asn Thr
65                  70                  75                  80

Ser Val Thr Gln Ser Gln Thr Val Ser Phe Asn Glu Arg Thr Thr Asp
                85                  90                  95
```

```
Thr Phe Thr Thr Ser Val Thr Thr Gly Phe Lys Thr Gly Thr Ser Val
                100                 105                 110
Lys Ser Thr Thr Lys Phe Lys Ile Ser Val Gly Phe Leu Ala Ala Gly
            115                 120                 125
Glu Leu Glu Gln Ser Val Glu Val Ala Val Asn Phe Glu Tyr Asn Tyr
        130                 135                 140
Ser Ser Thr Thr Thr Glu Thr His Ser Val Glu Arg Gly Trp Val Ile
145                 150                 155                 160
Thr Gln Pro Ile Ile Ala Pro Pro Arg Thr Arg Val Glu Ala Thr Leu
                165                 170                 175
Leu Ile Tyr Ala Gly Ser Val Asp Val Pro Ile Asp Leu Asn Ala Thr
            180                 185                 190
Ile Val Gly Asp Pro Ile Pro Trp Gln Asp Trp Gly Pro Ser Val Tyr
        195                 200                 205
Thr Ala Ser Phe Leu Asp Gly Asn Asn Leu Gly Trp Ser Gly Phe Ile
    210                 215                 220
Arg Pro Asp Glu Leu Ser Leu Ala Ser Ser Ala Tyr Arg Pro Val Gly
225                 230                 235                 240
Arg Thr Ala Ile Phe Ser Gly Leu Ala Thr Thr Asn Val Ala Ser Gly
                245                 250                 255
Leu Tyr Ser Ile Val Arg Ile Asp Glu Arg Pro Leu Pro Gly Phe Thr
            260                 265                 270
Gly Glu Thr Arg Arg Tyr Tyr Leu Pro Pro Ser Leu Ala Thr Pro Asp
        275                 280                 285
Gln Ile Leu Ser Thr Asn Thr Phe Gly Asn Asn Val Pro Ile Ile Asn
    290                 295                 300
Pro Val Pro Asn Ala His Cys Lys Lys Glu His Ser Pro Ile Ile Ile
305                 310                 315                 320
His Lys Asn Arg Glu Glu Lys Cys Glu Arg Asp Tyr Asp Glu Val Tyr
                325                 330                 335
Pro Arg His Asn Gln Val Glu Lys Cys Glu His Asn Tyr Asp Glu Val
            340                 345                 350
Tyr Pro Arg His Asn Gln Val Glu Lys Cys Glu Arg Asp Tyr Asp Glu
        355                 360                 365
Val Tyr Pro Arg His Asn Gln Val Glu Lys Tyr Glu His Asn Tyr Asp
    370                 375                 380
Glu Glu
385

<210> SEQ ID NO 11
<211> LENGTH: 1056
<212> TYPE: DNA
<213> ORGANISM: Artificial Sequence
<220> FEATURE:
<223> OTHER INFORMATION: tic1414
<220> FEATURE:
<223> OTHER INFORMATION: a recombinant polynucleotide encoding a TIC1414
      protein.

<400> SEQUENCE: 11
atggcaatta taaatcaatc atcactaaat tcaagaatac atgatttacg tgaagattca     60
agaacagctc ttgaaaaagt ttatactagt aataatcctt ggggtttcgt aagtatacac    120
tctgaccgac ttgaaaatta tcaactaact aatgtaaatg ttagtcctag gaatcaagat    180
tttcaaacga ttcctagatt gcaacactct gctacacaaa taattgaaaa taacacaagt    240
gtaacacaat ctcaaaccat ttcttttaat gaaagaacaa cagacacttt tacaacatcg    300
```

-continued

```
gttactacgg gatttaaaac tggaactagt gtgaaatcta cgacaaaatt caaatatct      360 gttggatttt tattagcagg cgaattagaa caatcagtgg aagtttctgt gaattttgag     420
tataattata gttcaacaac tacagagacg catagcgttg aaagaggatg acaatttca     480 cagcctataa ttgctccccc acgaacaagg gtagaagcta ctcttctaat ttatgctgga    540
tctgttgatg taccaattga tttaaatgct accattgttg gtgatccaat tccatggcca    600
tcgtgggggc cggcagtata ttctggatct tttcttgcta atgatggtcg gatatggtcg    660
gctcctatac taccagagca actatcactg gcatcttcag cgtatacaac tgttggaagg    720
acagcaaatt ttagcggttt agcgactacc aacgtttcct caggcctgta ttctattgtt    780
cgtattgatg aaagtccttt accaggattt acaggagaaa caaggcgtta ttatttaccg    840
ccttcattag cgactacaaa tcaaatactt tcgacaaatg cgttaggaaa taatgtgcca    900
attattaatc cagttcctaa tggacattgc aaaaaagatc attctccaat tattattcat    960
aaaaatagag aggtgaagtg cgaacacaat tatgatgaag tgtatcctcg tcatgatcaa   1020
gtagagaagt acgaacacaa ttatgatgaa gaataa                            1056
```

<210> SEQ ID NO 12
<211> LENGTH: 351
<212> TYPE: PRT
<213> ORGANISM: Artificial Sequence
<220> FEATURE:
<223> OTHER INFORMATION: TIC1414
<220> FEATURE:
<223> OTHER INFORMATION: an amino acid sequence translation of NT
      positions 1 through 1053 of SEQ ID NO: 11.

<400> SEQUENCE: 12

Met Ala Ile Ile Asn Gln Ser Ser Leu Asn Ser Arg Ile His Asp Leu
1               5                   10                  15

Arg Glu Asp Ser Arg Thr Ala Leu Glu Lys Val Tyr Thr Ser Asn Asn
            20                  25                  30

Pro Trp Gly Phe Val Ser Ile His Ser Asp Arg Leu Glu Asn Tyr Gln
        35                  40                  45

Leu Thr Asn Val Asn Val Ser Pro Arg Asn Gln Asp Phe Gln Thr Ile
    50                  55                  60

Pro Arg Leu Gln His Ser Ala Thr Gln Ile Ile Glu Asn Asn Thr Ser
65                  70                  75                  80

Val Thr Gln Ser Gln Thr Ile Ser Phe Asn Glu Arg Thr Thr Asp Thr
                85                  90                  95

Phe Thr Thr Ser Val Thr Thr Gly Phe Lys Thr Gly Thr Ser Val Lys
            100                 105                 110

Ser Thr Thr Lys Phe Lys Ile Ser Val Gly Phe Leu Leu Ala Gly Glu
        115                 120                 125

Leu Glu Gln Ser Val Glu Val Ser Val Asn Phe Glu Tyr Asn Tyr Ser
    130                 135                 140

Ser Thr Thr Thr Glu Thr His Ser Val Glu Arg Gly Trp Thr Ile Ser
145                 150                 155                 160

Gln Pro Ile Ile Ala Pro Pro Arg Thr Arg Val Glu Ala Thr Leu Leu
                165                 170                 175

Ile Tyr Ala Gly Ser Val Asp Val Pro Ile Asp Leu Asn Ala Thr Ile
            180                 185                 190

Val Gly Asp Pro Ile Pro Trp Pro Ser Trp Gly Pro Ala Val Tyr Ser
        195                 200                 205

```
Gly Ser Phe Leu Ala Asn Asp Gly Arg Ile Trp Ser Ala Pro Ile Leu
    210                 215                 220

Pro Glu Gln Leu Ser Leu Ala Ser Ser Ala Tyr Thr Thr Val Gly Arg
225                 230                 235                 240

Thr Ala Asn Phe Ser Gly Leu Ala Thr Thr Asn Val Ser Ser Gly Leu
                245                 250                 255

Tyr Ser Ile Val Arg Ile Asp Glu Ser Pro Leu Pro Gly Phe Thr Gly
            260                 265                 270

Glu Thr Arg Arg Tyr Tyr Leu Pro Pro Ser Leu Ala Thr Thr Asn Gln
        275                 280                 285

Ile Leu Ser Thr Asn Ala Leu Gly Asn Asn Val Pro Ile Ile Asn Pro
    290                 295                 300

Val Pro Asn Gly His Cys Lys Lys Asp His Ser Pro Ile Ile Ile His
305                 310                 315                 320

Lys Asn Arg Glu Val Lys Cys Glu His Asn Tyr Asp Glu Val Tyr Pro
                325                 330                 335

Arg His Asp Gln Val Glu Lys Tyr Glu His Asn Tyr Asp Glu Glu
            340                 345                 350

<210> SEQ ID NO 13
<211> LENGTH: 1107
<212> TYPE: DNA
<213> ORGANISM: Artificial Sequence
<220> FEATURE:
<223> OTHER INFORMATION: tic1885
<220> FEATURE:
<223> OTHER INFORMATION: a recombinant polynucleotide encoding a TIC1885
      protein.

<400> SEQUENCE: 13
atggcaatta taaatcaatc atcactaaat tcaagaatac atgatttacg tgaagattca      60
agaacagctc ttgaaaaagt ttatactagt aataatcctt ggggtttcgt aagtatacac     120
tctgaccgac ttgaaaatta tcaactaact aatgtaaatg ttagtcctag gaatcaagat     180
tttcaaacga ttcctagatt gcaacactct gctacacaaa taattgaaaa taacacaagt     240
gtaacacaat ctcaaaccat ttcttttaat gaaagaacaa cagacacttt tacaacatcg     300
gttactacgg gatttaaaac tggaactagt gtgaaatcta cgacaaaatt caaaatatct     360
gttggatttt tattagcagg cgaattagaa caatcagtgg aagtttctgt gaattttgag     420
tataattata gttcaacaac tacagagacg catagcgttg aaagaggatg gacaatttca     480
cagcctataa ttgctccccc acgaacaagg gtagaagcta ctcttctaat ttatgctgga     540
tctgttgatg taccaattga tttaaatgct accattgttg gtgatccaat tccatggcca     600 tcgtggggc tggcagtata ttctggatct tttcttgcta atgatggtcg gatatggtcg     660
gctcctatac taccagagca actatcactg gcatcttcag cgtatacaac tgttggaagg     720
acagcaaatt ttagcggttt agcgactacc aacgtttcct caggcctgta ttctattgtt     780
cgtattgatg aaagtccttt accaggattt acaggagaaa caaggcgtta ttatttaccg     840
ccttcattag cgactacaaa tcaaatactt tcgacaaatg cgttaggaaa taatgtgcca     900
attattaatc cagttcctaa tggacattgc aaaaagatc attctccaat tattattcat     960
aaaaatagag aggtgaagtg cgaacacaat tatgatgaag tgtatcctcg tcatgatcaa    1020
gtagagaagt gcgaacacaa ttatgatgaa gtgtatcctc gtcatgatca agtagagaag    1080
tacgaacaca attatgatga agaataa                                        1107
```

```
<210> SEQ ID NO 14
<211> LENGTH: 368
<212> TYPE: PRT
<213> ORGANISM: Artificial Sequence
<220> FEATURE:
<223> OTHER INFORMATION: TIC1885
<220> FEATURE:
<223> OTHER INFORMATION: an amino acid sequence translation of NT
      positions 1 through 1104 of SEQ ID NO: 13.

<400> SEQUENCE: 14

Met Ala Ile Ile Asn Gln Ser Ser Leu Asn Ser Arg Ile His Asp Leu
1               5                   10                  15

Arg Glu Asp Ser Arg Thr Ala Leu Glu Lys Val Tyr Thr Ser Asn Asn
            20                  25                  30

Pro Trp Gly Phe Val Ser Ile His Ser Asp Arg Leu Glu Asn Tyr Gln
        35                  40                  45

Leu Thr Asn Val Asn Val Ser Pro Arg Asn Gln Asp Phe Gln Thr Ile
    50                  55                  60

Pro Arg Leu Gln His Ser Ala Thr Gln Ile Ile Glu Asn Asn Thr Ser
65                  70                  75                  80

Val Thr Gln Ser Gln Thr Ile Ser Phe Asn Glu Arg Thr Thr Asp Thr
                85                  90                  95

Phe Thr Thr Ser Val Thr Thr Gly Phe Lys Thr Gly Thr Ser Val Lys
            100                 105                 110

Ser Thr Thr Lys Phe Lys Ile Ser Val Gly Phe Leu Leu Ala Gly Glu
        115                 120                 125

Leu Glu Gln Ser Val Glu Val Ser Val Asn Phe Glu Tyr Asn Tyr Ser
    130                 135                 140

Ser Thr Thr Thr Glu Thr His Ser Val Glu Arg Gly Trp Thr Ile Ser
145                 150                 155                 160

Gln Pro Ile Ile Ala Pro Pro Arg Thr Arg Val Glu Ala Thr Leu Leu
                165                 170                 175

Ile Tyr Ala Gly Ser Val Asp Val Pro Ile Asp Leu Asn Ala Thr Ile
            180                 185                 190

Val Gly Asp Pro Ile Pro Trp Pro Ser Trp Gly Leu Ala Val Tyr Ser
        195                 200                 205

Gly Ser Phe Leu Ala Asn Asp Gly Arg Ile Trp Ser Ala Pro Ile Leu
    210                 215                 220

Pro Glu Gln Leu Ser Leu Ala Ser Ser Ala Tyr Thr Thr Val Gly Arg
225                 230                 235                 240

Thr Ala Asn Phe Ser Gly Leu Ala Thr Thr Asn Val Ser Ser Gly Leu
                245                 250                 255

Tyr Ser Ile Val Arg Ile Asp Glu Ser Pro Leu Pro Gly Phe Thr Gly
            260                 265                 270

Glu Thr Arg Arg Tyr Tyr Leu Pro Pro Ser Leu Ala Thr Thr Asn Gln
        275                 280                 285

Ile Leu Ser Thr Asn Ala Leu Gly Asn Asn Val Pro Ile Ile Asn Pro
    290                 295                 300

Val Pro Asn Gly His Cys Lys Lys Asp His Ser Pro Ile Ile His Lys Asn
305                 310                 315                 320

Lys Asn Arg Glu Val Lys Cys Glu His Asn Tyr Asp Glu Val Tyr Pro
                325                 330                 335
```

```
Arg His Asp Gln Val Glu Lys Cys Glu His Asn Tyr Asp Glu Val Tyr
            340                 345                 350

Pro Arg His Asp Gln Val Glu Lys Tyr Glu His Asn Tyr Asp Glu Glu
        355                 360                 365
```

<210> SEQ ID NO 15
<211> LENGTH: 1158
<212> TYPE: DNA
<213> ORGANISM: Artificial Sequence
<220> FEATURE:
<223> OTHER INFORMATION: tic1922
<220> FEATURE:
<223> OTHER INFORMATION: a recombinant polynucleotide encoding a TIC1922 protein.

<400> SEQUENCE: 15

```
atggcaatta taaatcaatc atcactaaat tcaagaatac atgatttacg tgaagattca      60
agaacagctc ttgaaaaagt ttatactagt aataatcctt ggggtttcgt aagtatacac     120
tctgaccgac ttgaaaatta tcaactaact aatgtaaatg ttagtcctag gaatcaagat     180
tttcaaacga ttcctagatt gcaacactct gctacacaaa taattgaaaa taacacaagt     240
gtaacacaat ctcaaaccat ttctttaat gaaagaacaa cagacacttt tacaacatcg     300
gttactacgg gatttaaaac tggaactagt gtgaaatcta cgacaaaatt caaaatatct     360
gttggatttt tattagcagg cgaattagaa caatcagtgg aagtttctgt gaattttgag     420
tataattata gttcaacaac tacagagacg catagcgttg aaagaggatg gacaatttca     480
cagcctataa ttgctccccc acgaacaagg gtagaagcta ctcttctaat ttatgctgga     540
tctgttgatg taccaattga tttaaatgct accattgttg gtgatccaat tccatggcca     600
tcgtgggggc cggcagtata ttctggatct tttcttgcta atgatggtcg gatatggtcg     660
gctcctatac taccagagca actatcactg gcatcttcag cgtatacaac tgttggaagg     720
acagcaaatt ttagcggttt agcgactacc aacgtttcct caggcctgta ttctattgtt     780
cgtattgatg aaagtccttt accaggattt acaggagaaa caaggcgtta ttatttaccg     840
ccttcattag cgactacaaa tcaaatactt tcgacaaatg cgttaggaaa taatgtgcca     900
attattaatc cagttcctaa tggacattgc aaaaaagatc attctccaat tattattcat     960
aaaaatagag aggtgaagtg cgaacacaat tatgatgaag tgtatcctcg tcatgatcaa    1020
gtagagaagt gcgaacacaa ttatgatgaa gtgtatcctc gtcatgatca agtagagaag    1080
tgcgaacacg attatgatga agtgtatcct cgtcatgatc aagtagagaa gtacgaacac    1140
aattatgatg aagaataa                                                 1158
```

<210> SEQ ID NO 16
<211> LENGTH: 385
<212> TYPE: PRT
<213> ORGANISM: Artificial Sequence
<220> FEATURE:
<223> OTHER INFORMATION: TIC1922
<220> FEATURE:
<223> OTHER INFORMATION: an amino acid sequence translation of NT positions 1 through 1155 of SEQ ID NO: 15.

<400> SEQUENCE: 16

```
Met Ala Ile Ile Asn Gln Ser Ser Leu Asn Ser Arg Ile His Asp Leu
1               5                   10                  15

Arg Glu Asp Ser Arg Thr Ala Leu Glu Lys Val Tyr Thr Ser Asn Asn
            20                  25                  30
```

```
Pro Trp Gly Phe Val Ser Ile His Ser Asp Arg Leu Glu Asn Tyr Gln
            35                  40                  45

Leu Thr Asn Val Asn Val Ser Pro Arg Asn Gln Asp Phe Gln Thr Ile
 50                  55                  60

Pro Arg Leu Gln His Ser Ala Thr Gln Ile Ile Glu Asn Asn Thr Ser
 65                  70                  75                  80

Val Thr Gln Ser Gln Thr Ile Ser Phe Asn Glu Arg Thr Thr Asp Thr
                 85                  90                  95

Phe Thr Thr Ser Val Thr Thr Gly Phe Lys Thr Gly Thr Ser Val Lys
                100                 105                 110

Ser Thr Thr Lys Phe Lys Ile Ser Val Gly Phe Leu Leu Ala Gly Glu
            115                 120                 125

Leu Glu Gln Ser Val Glu Val Ser Val Asn Phe Glu Tyr Asn Tyr Ser
            130                 135                 140

Ser Thr Thr Thr Glu Thr His Ser Val Glu Arg Gly Trp Thr Ile Ser
145                 150                 155                 160

Gln Pro Ile Ile Ala Pro Pro Arg Thr Arg Val Glu Ala Thr Leu Leu
                165                 170                 175

Ile Tyr Ala Gly Ser Val Asp Val Pro Ile Asp Leu Asn Ala Thr Ile
            180                 185                 190

Val Gly Asp Pro Ile Pro Trp Pro Ser Trp Gly Pro Ala Val Tyr Ser
            195                 200                 205

Gly Ser Phe Leu Ala Asn Asp Gly Arg Ile Trp Ser Ala Pro Ile Leu
            210                 215                 220

Pro Glu Gln Leu Ser Leu Ala Ser Ser Ala Tyr Thr Thr Val Gly Arg
225                 230                 235                 240

Thr Ala Asn Phe Ser Gly Leu Ala Thr Asn Val Ser Ser Gly Leu
                245                 250                 255

Tyr Ser Ile Val Arg Ile Asp Glu Ser Pro Leu Pro Gly Phe Thr Gly
            260                 265                 270

Glu Thr Arg Arg Tyr Tyr Leu Pro Pro Ser Leu Ala Thr Thr Asn Gln
            275                 280                 285

Ile Leu Ser Thr Asn Ala Leu Gly Asn Asn Val Pro Ile Ile Asn Pro
290                 295                 300

Val Pro Asn Gly His Cys Lys Lys Asp His Ser Pro Ile Ile His
305                 310                 315                 320

Lys Asn Arg Glu Val Lys Cys Glu His Asn Tyr Asp Glu Val Tyr Pro
                325                 330                 335

Arg His Asp Gln Val Glu Lys Cys Glu His Asn Tyr Asp Glu Val Tyr
            340                 345                 350

Pro Arg His Asp Gln Val Glu Lys Cys Glu His Asp Tyr Asp Glu Val
            355                 360                 365

Tyr Pro Arg His Asp Gln Val Glu Lys Tyr Glu His Asn Tyr Asp Glu
            370                 375                 380

Glu
385

<210> SEQ ID NO 17
<211> LENGTH: 1059
<212> TYPE: DNA
<213> ORGANISM: Artificial Sequence
<220> FEATURE:
<223> OTHER INFORMATION: tic1422
<220> FEATURE:
<223> OTHER INFORMATION: a recombinant polynucleotide encoding a TIC1422
      protein.
```

<400> SEQUENCE: 17

```
atggcaatta taaatcaatc atcactaaat tcaagaatac atgatttata tgaagattca     60
agaacagctt tgatatatt tcgtagaaat gaacccttgg gttttaatgg aagagtccct    120
ggacgtgaag cctttcatga ttatcaacta actaatgtaa ctgttagtcc taggaatcaa    180
gctttccaaa cgaccctag tttacaacac actgctacac aaagaattga aataacaca    240
agtgtaacac aatctcagac catttctttt aatgaaagaa caacagacac ttttacaacc    300
tctgttacta caggatttaa aactggaact agtgtgaaat ctacgacaaa attcaaagta    360
tctgttggat ttttagcagc aggcgaatta gaacaatcag tggaagttgc tgttaatttt    420
gagtataatt atagttcaac gactacagag acgcatagcg ttgaaagagg atgggtaatt    480
acacagccta ttattgctcc cccacgaaca atagtagaag ctactcttct aatttatgct    540
ggttctgtta atgtaccaat tgatttaaat gctaccattg ttggtgatcc aattccatgg    600
ggagaatggg gaccggcatt gtatacgtct cacttcctcg acaggaataa tagcgagtgg    660
tcgagtttta taaggccaga tcaactttca ttggcatctt cagcgtatag acctgctgga    720
agaacagcaa ttttagtgg tttagcgaat actaacattg cctccggcct atattctgtt    780
gtgcgtattg atgaaaggcc tttaccagga tttacagggg aaacaaggcg ttattattta    840
ccgccttcat tagctactcc agatcaaata cttcgacaa atgcgttagg aaataatgtg    900
ccaattatta atccagttcc taatgcacat tgcaaaaaag aacattctcc aattattatt    960
cataaaaata gagaagagaa gtgtgaacgc gattatgatg aagtgtatcc tcgtcataat   1020
caagtagaga agtgcgaaca caattatgat gaagaataa                         1059
```

<210> SEQ ID NO 18
<211> LENGTH: 352
<212> TYPE: PRT
<213> ORGANISM: Artificial Sequence
<220> FEATURE:
<223> OTHER INFORMATION: TIC1422
<220> FEATURE:
<223> OTHER INFORMATION: an amino acid sequence translation of NT
      positions 1 through 1056 of SEQ ID NO: 17.

<400> SEQUENCE: 18

```
Met Ala Ile Ile Asn Gln Ser Ser Leu Asn Ser Arg Ile His Asp Leu
1               5                   10                  15

Tyr Glu Asp Ser Arg Thr Ala Phe Asp Ile Phe Arg Arg Asn Glu Pro
            20                  25                  30

Leu Gly Phe Asn Gly Arg Val Pro Gly Arg Glu Ala Phe His Asp Tyr
        35                  40                  45

Gln Leu Thr Asn Val Thr Val Ser Pro Arg Asn Gln Ala Phe Gln Thr
    50                  55                  60

Thr Pro Ser Leu Gln His Thr Ala Thr Gln Arg Ile Glu Asn Asn Thr
65                  70                  75                  80

Ser Val Thr Gln Ser Gln Thr Ile Ser Phe Asn Glu Arg Thr Thr Asp
                85                  90                  95

Thr Phe Thr Thr Ser Val Thr Thr Gly Phe Lys Thr Gly Thr Ser Val
            100                 105                 110

Lys Ser Thr Thr Lys Phe Lys Val Ser Val Gly Phe Leu Ala Ala Gly
        115                 120                 125

Glu Leu Glu Gln Ser Val Glu Val Ala Val Asn Phe Glu Tyr Asn Tyr
    130                 135                 140
```

| | | | | | | | | | | | | | | | |
|---|---|---|---|---|---|---|---|---|---|---|---|---|---|---|---|
|Ser|Ser|Thr|Thr|Thr|Glu|Thr|His|Ser|Val|Glu|Arg|Gly|Trp|Val|Ile|
|145| | | | |150| | | | |155| | | | |160|

Thr Gln Pro Ile Ile Ala Pro Pro Arg Thr Ile Val Glu Ala Thr Leu
                165                 170                 175

Leu Ile Tyr Ala Gly Ser Val Asn Val Pro Ile Asp Leu Asn Ala Thr
            180                 185                 190

Ile Val Gly Asp Pro Ile Pro Trp Gly Glu Trp Gly Pro Ala Leu Tyr
        195                 200                 205

Thr Ser His Phe Leu Asp Arg Asn Asn Ser Glu Trp Ser Ser Phe Ile
    210                 215                 220

Arg Pro Asp Gln Leu Ser Leu Ala Ser Ser Ala Tyr Arg Pro Ala Gly
225                 230                 235                 240

Arg Thr Ala Ile Phe Ser Gly Leu Ala Asn Thr Asn Ile Ala Ser Gly
                245                 250                 255

Leu Tyr Ser Val Val Arg Ile Asp Glu Arg Pro Leu Pro Gly Phe Thr
            260                 265                 270

Gly Glu Thr Arg Arg Tyr Tyr Leu Pro Pro Ser Leu Ala Thr Pro Asp
        275                 280                 285

Gln Ile Leu Ser Thr Asn Ala Leu Gly Asn Asn Val Pro Ile Ile Asn
    290                 295                 300

Pro Val Pro Asn Ala His Cys Lys Lys Glu His Ser Pro Ile Ile Ile
305                 310                 315                 320

His Lys Asn Arg Glu Glu Lys Cys Glu Arg Asp Tyr Asp Glu Val Tyr
                325                 330                 335

Pro Arg His Asn Gln Val Glu Lys Cys Glu His Asn Tyr Asp Glu Glu
            340                 345                 350

<210> SEQ ID NO 19
<211> LENGTH: 1059
<212> TYPE: DNA
<213> ORGANISM: Artificial Sequence
<220> FEATURE:
<223> OTHER INFORMATION: tic1974
<220> FEATURE:
<223> OTHER INFORMATION: a recombinant polynucleotide encoding a TIC1974
      protein.

<400> SEQUENCE: 19
atggcaatta taaatgaatc attactgaat tcaagaatac atgatttata tgaagattca      60
agaacagctt tgatatatt tcgtagaaat gaacccttgg gttttaatgg aagagtccct     120
ggacgtgaag cctttcatga ttatcaacta actaatgtaa ctgttagtcc taggaatcaa     180
gctttccaaa cgaccccctag tttacaacac actgctacac aaagaattga aaataacaca     240
agtgtaacac aatctcagac catttctttt aatgaaagaa caacagacac ttttacaacc     300
tctgttacta caggatttaa aactggaact agtgtgaaat ctacgacaaa attcaaagta     360
tctgttggat ttttagcagc aggcgaatta gaacaatcag tggaagttgc tgttaatttt     420
gagtataatt atagttcaac gactacagag acgcatagcg ttgaaagagg atgggtaatt     480
acacagccta ttattgctcc cccacgaaca atagtagaag ctactcttct aatttatgct     540
ggttctgtta atgtaccaat tgatttaaat gctaccattg ttggtgatcc aattccatgg     600
ggagaatggg gaccggcatt gtatacgtct cacttcctcg acaggaataa tagcgagtgg     660
tcgagtttta taaggccaga tcaactttca ttggcatctt cagcgtatag acctgctgga     720
agaacagcaa ttttagtgg tttagcgaat actaacattg cctccggcct atattctgtt     780
gtgcgtattg atgaaaggcc tttaccagga tttacagggg aaacaaggcg ttattattta     840

```
ccgccttcat tagctactcc agatcaaata ctttcgacaa atgcgttagg aaataatgtg    900
ccaattatta atccagttcc taatgcacat tgcaaaaaag aacattctcc aattattatt    960
cataaaaata gagaagagaa gtgtgaacgc gattatgatg aagtgtatcc tcgtcataat   1020
caagtagaga agtgcgaaca caattatgat gaagaataa                          1059
```

```
<210> SEQ ID NO 20
<211> LENGTH: 352
<212> TYPE: PRT
<213> ORGANISM: Artificial Sequence
<220> FEATURE:
<223> OTHER INFORMATION: TIC1974
<220> FEATURE:
<223> OTHER INFORMATION: an amino acid sequence translation of NT
      positions 1 through 1056 of SEQ ID NO: 19.

<400> SEQUENCE: 20

Met Ala Ile Ile Asn Glu Ser Leu Leu Asn Ser Arg Ile His Asp Leu
  1               5                  10                  15

Tyr Glu Asp Ser Arg Thr Ala Phe Asp Ile Phe Arg Arg Asn Glu Pro
                 20                  25                  30

Leu Gly Phe Asn Gly Arg Val Pro Gly Arg Glu Ala Phe His Asp Tyr
             35                  40                  45

Gln Leu Thr Asn Val Thr Val Ser Pro Arg Asn Gln Ala Phe Gln Thr
         50                  55                  60

Thr Pro Ser Leu Gln His Thr Ala Thr Gln Arg Ile Glu Asn Asn Thr
 65                  70                  75                  80

Ser Val Thr Gln Ser Gln Thr Ile Ser Phe Asn Glu Arg Thr Thr Asp
                 85                  90                  95

Thr Phe Thr Thr Ser Val Thr Gly Phe Lys Thr Gly Thr Ser Val
                100                 105                 110

Lys Ser Thr Thr Lys Phe Lys Val Ser Val Gly Phe Leu Ala Ala Gly
            115                 120                 125

Glu Leu Glu Gln Ser Val Glu Val Ala Val Asn Phe Glu Tyr Asn Tyr
        130                 135                 140

Ser Ser Thr Thr Thr Glu Thr His Ser Val Glu Arg Gly Trp Val Ile
145                 150                 155                 160

Thr Gln Pro Ile Ile Ala Pro Pro Arg Thr Ile Val Glu Ala Thr Leu
                165                 170                 175

Leu Ile Tyr Ala Gly Ser Val Asn Val Pro Ile Asp Leu Asn Ala Thr
            180                 185                 190

Ile Val Gly Asp Pro Ile Pro Trp Gly Glu Trp Gly Pro Ala Leu Tyr
        195                 200                 205

Thr Ser His Phe Leu Asp Arg Asn Asn Ser Glu Trp Ser Ser Phe Ile
    210                 215                 220

Arg Pro Asp Gln Leu Ser Leu Ala Ser Ser Ala Tyr Arg Pro Ala Gly
225                 230                 235                 240

Arg Thr Ala Ile Phe Ser Gly Leu Ala Asn Thr Asn Ile Ala Ser Gly
                245                 250                 255

Leu Tyr Ser Val Val Arg Ile Asp Glu Arg Pro Leu Pro Gly Phe Thr
            260                 265                 270

Gly Glu Thr Arg Arg Tyr Tyr Leu Pro Pro Ser Leu Ala Thr Pro Asp
        275                 280                 285

Gln Ile Leu Ser Thr Asn Ala Leu Gly Asn Asn Val Pro Ile Ile Asn
    290                 295                 300
```

```
Pro Val Pro Asn Ala His Cys Lys Lys Glu His Ser Pro Ile Ile Ile
305                 310                 315                 320

His Lys Asn Arg Glu Glu Lys Cys Glu Arg Asp Tyr Asp Glu Val Tyr
            325                 330                 335

Pro Arg His Asn Gln Val Glu Lys Cys Glu His Asn Tyr Asp Glu Glu
        340                 345                 350

<210> SEQ ID NO 21
<211> LENGTH: 1158
<212> TYPE: DNA
<213> ORGANISM: Artificial Sequence
<220> FEATURE:
<223> OTHER INFORMATION: tic2032
<220> FEATURE:
<223> OTHER INFORMATION: a recombinant polynucleotide encoding a TIC2032
      protein.

<400> SEQUENCE: 21
atggcaatta taaatcaatc atcactaaat tcaagaatac atgatttacg tgaagattca      60
agaacagctc ttgaaaaagt ttatactagt aataatcctt ggggtttcgt aagtatacac    120
tctgaccgac ttgaaaatta tcaactaact aatgtaaatg ttagtcctag gaatcaagat    180
ttccaaacga ttcctaggtt acaacacact gctacacaag taattgaaaa aacacaagt    240 gtaacacaat ctcaaaccgt ttctttcaat gaaagaacaa cagacacttt tacaacatcg    300
gttactacgg gatttaaaac tggaactagt gtgaaatcta cgacaaaatt caaaatatct    360
gttggatttt tagcagcagg cgaattagaa caatcagtgg aagttgctgt taattttgag    420
tataattata gttcaacaac tacagagacg catagcgttg aaagaggatg gacaatttca    480
cagcctataa ttgctccccc acgaacaagg gtagaagcta ctcttctaat ttatgctgga    540
tctgttgatg taccaattga tttaaatgct accattgttg gtgatccaat tccctggcaa    600
gattggggtc atcagtata tacagcctct ttcctcgacg ggaataattt ggggtggtcg    660
ggttttatac gaccagatga actatcattg gcatcttcgg catatagacc tgttggaaga    720
acagcaattt ttagcggttt agcgactacc aacgtttcct caggcctgta ttctattgtt    780
cgtattgatg aaagtccttt accaggattt acaggagaaa caaggcgtta ttatttaccg    840
ccttcattag cgactacaaa tcaaatactt tcgacaaatg cgttaagaaa taatgtgcca    900
attattaatc cagttcctaa tgcacattgc aaaaagaac attctccaat tattattcat    960
aaaaatagag aagagaagtg tgaacgcgat tatgatgaag tgtatcctcg tcataatcaa   1020
gtagagaagt gcgaacacaa ttatgatgaa gtgtatcctc gtcataatca agtagagaag   1080
tgtgaacgcg attatgatga agtgtatcct cgtcataatc aagtagagaa gtgcgaacac   1140
aattatgatg aagaataa                                                 1158

<210> SEQ ID NO 22
<211> LENGTH: 385
<212> TYPE: PRT
<213> ORGANISM: Artificial Sequence
<220> FEATURE:
<223> OTHER INFORMATION: TIC2032
<220> FEATURE:
<223> OTHER INFORMATION: an amino acid sequence translation of NT
      positions 1 through 1155 of SEQ ID NO: 21.
```

```
<400> SEQUENCE: 22

Met Ala Ile Ile Asn Gln Ser Ser Leu Asn Ser Arg Ile His Asp Leu
1               5                   10                  15

Arg Glu Asp Ser Arg Thr Ala Leu Glu Lys Val Tyr Thr Ser Asn Asn
            20                  25                  30

Pro Trp Gly Phe Val Ser Ile His Ser Asp Arg Leu Glu Asn Tyr Gln
        35                  40                  45

Leu Thr Asn Val Asn Val Ser Pro Arg Asn Gln Asp Phe Gln Thr Ile
    50                  55                  60

Pro Arg Leu Gln His Thr Ala Thr Gln Val Ile Glu Asn Asn Thr Ser
65                  70                  75                  80

Val Thr Gln Ser Gln Thr Val Ser Phe Asn Glu Arg Thr Thr Asp Thr
                85                  90                  95

Phe Thr Thr Ser Val Thr Thr Gly Phe Lys Thr Gly Thr Ser Val Lys
            100                 105                 110

Ser Thr Thr Lys Phe Lys Ile Ser Val Gly Phe Leu Ala Ala Gly Glu
        115                 120                 125

Leu Glu Gln Ser Val Glu Val Ala Val Asn Phe Glu Tyr Asn Tyr Ser
    130                 135                 140

Ser Thr Thr Thr Glu Thr His Ser Val Glu Arg Gly Trp Thr Ile Ser
145                 150                 155                 160

Gln Pro Ile Ile Ala Pro Pro Arg Thr Arg Val Glu Ala Thr Leu Leu
                165                 170                 175

Ile Tyr Ala Gly Ser Val Asp Val Pro Ile Asp Leu Asn Ala Thr Ile
            180                 185                 190

Val Gly Asp Pro Ile Pro Trp Gln Asp Trp Gly Pro Ser Val Tyr Thr
        195                 200                 205

Ala Ser Phe Leu Asp Gly Asn Asn Leu Gly Trp Ser Gly Phe Ile Arg
    210                 215                 220

Pro Asp Glu Leu Ser Leu Ala Ser Ser Ala Tyr Arg Pro Val Gly Arg
225                 230                 235                 240

Thr Ala Ile Phe Ser Gly Leu Ala Thr Thr Asn Val Ser Ser Gly Leu
                245                 250                 255

Tyr Ser Ile Val Arg Ile Asp Glu Ser Pro Leu Pro Gly Phe Thr Gly
            260                 265                 270

Glu Thr Arg Arg Tyr Tyr Leu Pro Pro Ser Leu Ala Thr Thr Asn Gln
        275                 280                 285

Ile Leu Ser Thr Asn Ala Leu Arg Asn Asn Val Pro Ile Ile Asn Pro
    290                 295                 300

Val Pro Asn Ala His Cys Lys Lys Glu His Ser Pro Ile Ile Ile His
305                 310                 315                 320

Lys Asn Arg Glu Glu Lys Cys Glu Arg Asp Tyr Asp Glu Val Tyr Pro
                325                 330                 335

Arg His Asn Gln Val Glu Lys Cys Glu His Asn Tyr Asp Glu Val Tyr
            340                 345                 350

Pro Arg His Asn Gln Val Glu Lys Cys Glu Arg Asp Tyr Asp Glu Val
        355                 360                 365

Tyr Pro Arg His Asn Gln Val Glu Lys Cys Glu His Asn Tyr Asp Glu
    370                 375                 380

Glu
385
```

<210> SEQ ID NO 23
<211> LENGTH: 1107
<212> TYPE: DNA
<213> ORGANISM: Artificial Sequence
<220> FEATURE:
<223> OTHER INFORMATION: tic2120
<220> FEATURE:
<223> OTHER INFORMATION: a recombinant polynucleotide encoding a TIC2120 protein.

<400> SEQUENCE: 23

```
atggaaatta taaatcaatc atcactaaat tctagaatac atgatttact tgaagattca      60
cgaacagctt tcatacaaaa gtatactaat aacacttcta cgggtctcgc aactatacgc     120
agtggacaac ttgataaata tcaactaact aatgtaaatg ttagtcctag gaatcaagat     180
ttccaaacga tacctaggtt acaacacact gctacacaaa taattgaaaa taacacaagt     240
gtaacacaat ctcaaaccgt ttcttttaat gaaaaaacaa cagacacttt tacaacctct     300
gttactacgg gatttaaaac tggaactagt gtgaaatcta cgacaaaatt cactgtattt     360
gttggatttt tattagcagg ctcagtagaa caaacagtgg aggttgcagt aaattttgag     420
tataattata gttcaacaac tacagagacg catagcgttg aaagaggatg ggtaattaca     480
cagcctataa ttgctccccc acgaacaagg gtagaagcta cacttctaat ttatgctggt     540
tctgttgatg taccaattga tttaaatgct accattgttg gtgatccaat tccatggtta     600
gaatggggc cgtcagtatt taccggatct tttggcta ataatggttt cggatataca     660
ggcttcttaa gaccagatga actatcatta gcatcttcag cgtatagacc tgttggaagg     720
acagcaattt ttagcggttt agcgactacc aatgttgcct caggtctgta ctctattgtt     780
cgtattgatg aaacaccttt gccaggtcat tcagggcagt caagaacgta ttatttaccg     840
ccttcattag cgactcaaaa tcaaatactt tcgaataatg cgttaggaaa taatgtgcca     900
attattaatc cagttcctaa tgcgcattgt aaaaagaac attctccaat tattattcat     960
aaaaatagag aggagaagtg cgaacacaat tatgatgaag tgcatcctgg tcatgatcaa    1020
gtagagaagt gcgaacacaa ttatgatgaa gtgtatcctg gtcatgatca agtagagaag    1080
tacgaacaca attatgatga agaataa                                        1107
```

<210> SEQ ID NO 24
<211> LENGTH: 368
<212> TYPE: PRT
<213> ORGANISM: Artificial Sequence
<220> FEATURE:
<223> OTHER INFORMATION: TIC2120
<220> FEATURE:
<223> OTHER INFORMATION: an amino acid sequence translation of NT positions 1 through 1104 of SEQ ID NO: 23.

<400> SEQUENCE: 24

```
Met Glu Ile Ile Asn Gln Ser Ser Leu Asn Ser Arg Ile His Asp Leu
1               5                   10                  15

Leu Glu Asp Ser Arg Thr Ala Phe Ile Gln Lys Tyr Thr Asn Asn Thr
            20                  25                  30

Ser Thr Gly Leu Ala Thr Ile Arg Ser Gly Gln Leu Asp Lys Tyr Gln
        35                  40                  45

Leu Thr Asn Val Asn Val Ser Pro Arg Asn Gln Asp Phe Gln Thr Ile
    50                  55                  60

Pro Arg Leu Gln His Thr Ala Thr Gln Ile Ile Glu Asn Asn Thr Ser
65                  70                  75                  80
```

```
Val Thr Gln Ser Gln Thr Val Ser Phe Asn Glu Lys Thr Thr Asp Thr
                85                  90                  95

Phe Thr Thr Ser Val Thr Gly Phe Lys Thr Gly Thr Ser Val Lys
            100                 105                 110

Ser Thr Thr Lys Phe Thr Val Phe Val Gly Phe Leu Leu Ala Gly Ser
            115                 120                 125

Val Glu Gln Thr Val Glu Val Ala Val Asn Phe Glu Tyr Asn Tyr Ser
            130                 135                 140

Ser Thr Thr Thr Glu Thr His Ser Val Glu Arg Gly Trp Val Ile Thr
145                 150                 155                 160

Gln Pro Ile Ile Ala Pro Pro Arg Thr Arg Val Glu Ala Thr Leu Leu
                165                 170                 175

Ile Tyr Ala Gly Ser Val Asp Val Pro Ile Asp Leu Asn Ala Thr Ile
            180                 185                 190

Val Gly Asp Pro Ile Pro Trp Leu Glu Trp Gly Pro Ser Val Phe Thr
            195                 200                 205

Gly Ser Phe Trp Ala Asn Asn Gly Phe Gly Tyr Thr Gly Phe Leu Arg
210                 215                 220

Pro Asp Glu Leu Ser Leu Ala Ser Ser Ala Tyr Arg Pro Val Gly Arg
225                 230                 235                 240

Thr Ala Ile Phe Ser Gly Leu Ala Thr Thr Asn Val Ala Ser Gly Leu
                245                 250                 255

Tyr Ser Ile Val Arg Ile Asp Glu Thr Pro Leu Pro Gly His Ser Gly
            260                 265                 270

Gln Ser Arg Thr Tyr Tyr Leu Pro Pro Ser Leu Ala Thr Gln Asn Gln
            275                 280                 285

Ile Leu Ser Asn Asn Ala Leu Gly Asn Asn Val Pro Ile Ile Asn Pro
290                 295                 300

Val Pro Asn Ala His Cys Lys Lys Glu His Ser Pro Ile Ile His
305                 310                 315                 320

Lys Asn Arg Glu Glu Lys Cys Glu His Asn Tyr Asp Glu Val His Pro
                325                 330                 335

Gly His Asp Gln Val Glu Lys Cys Glu His Asn Tyr Asp Glu Val Tyr
            340                 345                 350

Pro Gly His Asp Gln Val Glu Lys Tyr Glu His Asn Tyr Asp Glu Glu
            355                 360                 365
```

<210> SEQ ID NO 25
<211> LENGTH: 1056
<212> TYPE: DNA
<213> ORGANISM: Artificial Sequence
<220> FEATURE:
<223> OTHER INFORMATION: tic1362
<220> FEATURE:
<223> OTHER INFORMATION: a recombinant polynucleotide encoding a TIC1362
      protein.

<400> SEQUENCE: 25

```
atggcaatta ttgatgatat tgcacaagac gcatcaaaag cttgggatgt tacatttgga    60
ccatctatac ggcctggaac aacacctaca gaccgtactc tatttaatta tcaactaaca   120
gatatagtgg ctaaccctag aacagtcaat ttttcagttg tacctgaact aatccgtacg   180
gcctcacaga ctattgaaaa cgcatcaact acgcaacaaa gtcaaacatt aacattttct   240
gaaacaacaa cggacacagt gacatcttcc gtaactcacg gtttcaagac tggggttagt   300
gttacagctt cagcaaaatg gaacgctaat atactaataa gttctatcga acaaagcttt   360
```

```
tcaacaacgg tttccacaga atataatttt agtagtactt caactcaatc aacttctgta    420
gcaagaagtt ggacgattac tcagccacta atagctcctc cccattccaa aattacagca    480
accctgttta tttatggagg gagttttagt gtgcctatgg acctacaagt gagaattgtt    540
ggagaaagaa ttaatccaac atatcctaat gttggatata tttacagtgc cagatttaga    600
catacaaatg gtagcaacta tagagggttg ctttcagcag actttcttgc agctgcttcc    660
tctgcgtatc gttctgttgg atacgatgca atttggagag aacagctac ttcgacagtt     720 tcacaagggt tgtattctgt cgtacgaata gatgagactc ctttaccagg ttttgcagga    780
gaaacgcgaa gatattattt gccagtagta ccagctgaaa atgcaagtaa aattcttaca    840
cctggatcgc taggaagtga gattataatt atcaacccaa tcccaaatgc atcctgtaaa    900
agagagagac cgcctattat tcttcctcat gatagaaag agacgtgtga gcgtcattat     960
gatgaagggc acgttcgtca taatggtgta gaaaaatgtg agcgtcattg tgatgaagaa    1020
tactatgatg atgaagaata ctatgatgaa gaataa                              1056
```

<210> SEQ ID NO 26
<211> LENGTH: 351
<212> TYPE: PRT
<213> ORGANISM: Artificial Sequence
<220> FEATURE:
<223> OTHER INFORMATION: TIC1362
<220> FEATURE:
<223> OTHER INFORMATION: an amino acid sequence translation of NT
      positions 1 through 1053 of SEQ ID NO: 25.

<400> SEQUENCE: 26

```
Met Ala Ile Ile Asp Asp Ile Ala Gln Asp Ala Ser Lys Ala Trp Asp
1               5                   10                  15

Val Thr Phe Gly Pro Ser Ile Arg Pro Gly Thr Thr Pro Thr Asp Arg
            20                  25                  30

Thr Leu Phe Asn Tyr Gln Leu Thr Asp Ile Val Ala Asn Pro Arg Thr
        35                  40                  45

Val Asn Phe Ser Val Val Pro Glu Leu Ile Arg Thr Ala Ser Gln Thr
    50                  55                  60

Ile Glu Asn Ala Ser Thr Thr Gln Gln Ser Gln Thr Leu Thr Phe Ser
65                  70                  75                  80

Glu Thr Thr Thr Asp Thr Val Thr Ser Ser Val Thr His Gly Phe Lys
                85                  90                  95

Thr Gly Val Ser Val Thr Ala Ser Ala Lys Trp Asn Ala Asn Ile Leu
            100                 105                 110

Ile Ser Ser Ile Glu Gln Ser Phe Ser Thr Thr Val Ser Thr Glu Tyr
        115                 120                 125

Asn Phe Ser Ser Thr Ser Thr Gln Ser Thr Ser Val Ala Arg Ser Trp
    130                 135                 140

Thr Ile Thr Gln Pro Leu Ile Ala Pro Pro His Ser Lys Ile Thr Ala
145                 150                 155                 160

Thr Leu Phe Ile Tyr Gly Gly Ser Phe Ser Val Pro Met Asp Leu Gln
                165                 170                 175

Val Arg Ile Val Gly Glu Arg Ile Asn Pro Thr Tyr Pro Asn Val Gly
            180                 185                 190

Tyr Ile Tyr Ser Ala Arg Phe Arg His Thr Asn Gly Ser Asn Tyr Arg
        195                 200                 205

Gly Leu Leu Ser Ala Asp Phe Leu Ala Ala Ala Ser Ser Ala Tyr Arg
    210                 215                 220
```

```
Ser Val Gly Tyr Asp Ala Ile Trp Arg Gly Thr Ala Thr Ser Thr Val
225                 230                 235                 240

Ser Gln Gly Leu Tyr Ser Val Val Arg Ile Asp Glu Thr Pro Leu Pro
            245                 250                 255

Gly Phe Ala Gly Glu Thr Arg Arg Tyr Tyr Leu Pro Val Val Pro Ala
        260                 265                 270

Glu Asn Ala Ser Lys Ile Leu Thr Pro Gly Ser Leu Gly Ser Glu Ile
    275                 280                 285

Ile Ile Ile Asn Pro Ile Pro Asn Ala Ser Cys Lys Arg Glu Arg Pro
        290                 295                 300

Pro Ile Ile Leu Pro His Asp Arg Glu Glu Thr Cys Glu Arg His Tyr
305                 310                 315                 320

Asp Glu Gly His Val Arg His Asn Gly Val Glu Lys Cys Glu Arg His
                325                 330                 335

Cys Asp Glu Glu Tyr Tyr Asp Asp Glu Glu Tyr Tyr Asp Glu Glu
            340                 345                 350
```

<210> SEQ ID NO 27
<211> LENGTH: 1161
<212> TYPE: DNA
<213> ORGANISM: Artificial Sequence
<220> FEATURE:
<223> OTHER INFORMATION: tic1415
<220> FEATURE:
<223> OTHER INFORMATION: a recombinant polynucleotide encoding a
      TIC1415.

<400> SEQUENCE: 27

```
atggccatca ttaaccagtc tagcctgaac tctcgtatcc acgacctcct tgaggactct      60
agggaggctt tcgacatctt ctaccgtgac cgccctggcg gtttcaacgg acgtattcct     120
ggtagggagc agctcgacaa ctaccaactg accaacgtga acgtgagccc tcgcaaccag     180
gacttccaga ccatccctcg cctccagcac accgccaccc aagtgatcga gaacaatacc     240
tccgtgaccc agtcccagac cgtgtccttc aacgagcgca ccactgacac cttcaccact     300
agcgtgacca ctggcttcaa gaccggcacc tccgtgaagt ccaccactaa gttcaagatt     360
tccgtgggct tcctcgccgc tggcgagctt gagcagtccg tggaggtggc cgtgaacttc     420
gagtacaact actccagcac cactactgag actcactccg tcgagcgcgg ctgggtcatc     480
actcagccca tcattgctcc tcctaggact agagtcgagg ctacgctcct gatctacgct     540
ggcagcgtgg acgtccctat cgacctcaac gctaccatcg tcggcgaccc tatcccttgg     600
caagactggg gccctagcgt gtacacggct agtttcctcg acggcaacaa tctgggttgg     660
tctgggttta tccgccctga tgagctgtct ctggcgtcgt cagcgtacag gcccgtcggg     720
cggacggcga tcttcagtgg gcttgcgacg acaaacgtcg catccgggct ttactcgatt     780
gtccggattg atgagcgtcc acttccggga ttcacgggag agacacggcg ttactatctt     840
ccgccatcat tggcaacacc ggatcagatc ctttcaacaa acacattcgg aaacaatgtt     900
ccgattatca acccggttcc aaacgcacac tgcaagaagg agcacagtcc aatcatcatc     960
cacaagaacc gtgaggaaaa gtgcgagcgt gattacgatg aggtttaccc caggcacaac    1020
caggttgaga atgtgagcca taactacgac gaggtgtacc aagacacaac ccaggtcgag    1080
aagtgcgaac gtgattatga cgaagtgtac ccgcgacata ccaggtggaa gaaatgtgaa    1140
cataactacg acgaggagtg a                                              1161
```

<210> SEQ ID NO 28
<211> LENGTH: 1056
<212> TYPE: DNA
<213> ORGANISM: Artificial Sequence
<220> FEATURE:
<223> OTHER INFORMATION: tic1414
<220> FEATURE:
<223> OTHER INFORMATION: a recombinant polynucleotide encoding a TIC1414

<400> SEQUENCE: 28

```
atggctatta tcaaccagtc tagtttgaac tccagaatcc atgatttgag ggaagatagt      60
agaactgctc ttgagaaggt ttacacttcc aacaacccct gggggtttcgt gagtattcat    120
agtgacagat ggagaactga ccaattgact aacgtcaacg tctctcctcg taaccaggac    180
ttccaaacta ttcctaggct tcaacacagt gctactcaaa ttatcgagaa caacactagc    240
gttactcaat ctcagactat ttctttcaac gagcgtacta ctgatacttt cactacctct    300
gttactaccg gtttcaagac cggcacctct gttaagagca ccacaaagtt caagatcagc    360
gttggtttcc tccttgctgg tgagcttgag cagtctgttg aagtctcagt gaacttcgag    420
tacaactact catccaccac caccgagacc catagcgtgg agcgtggatg gaccatctca    480
cagcctatca tcgctcctcc aaggaccagg gtggaggcta ccctcctcat ctacgctggc    540
tcagtggatg tgcctattga tcttaacgct accattgtgg gagatcctat cccttggcca    600
tcatggggac cagcagtgta ctcaggatca ttccttgcaa cgacggacg tatctggtcc    660
gcaccaatcc ttccagaaca gctctcccctc gcatccagcg cctacacaac ggtgggccgt    720
acagccaact tcagcggcct cgccacaacg aatgtctcca gcggcctcta cagcatcgtc    780
cgtatcgacg aaagcccact gccaggcttt acaggcgaaa cacgccgtta ctatctgcca    840
ccctccctgg ccacaacgaa ccagatcctc tcgacaaatg cgctcgggaa caatgtcccg    900
atcatcaacc ctgtcccgaa tgggcattgc aagaaggacc actcgccgat aatcatacac    960
aagaaccgcg aagtcaaatg tgaacacaat tatgacgaag tgtacccgcg ccacgaccaa   1020
gtggagaagt acgaacacaa ctatgacgaa gaatga                             1056
```

<210> SEQ ID NO 29
<211> LENGTH: 1059
<212> TYPE: DNA
<213> ORGANISM: Artificial Sequence
<220> FEATURE:
<223> OTHER INFORMATION: tic1422
<220> FEATURE:
<223> OTHER INFORMATION: a recombinant polynucleotide encoding a TIC1422

<400> SEQUENCE: 29

```
atggccatca ttaaccagag cagcctgaac tcccgcatcc acgacctcta cgaggactct      60
aggaccgcct tcgacatctt ccgtaggaac gagccgctag gcttcaacgg tcgcgtgccc    120
ggtagggagg cgttccacga ctaccagctc accaacgtga ccgtgagccc gcgcaaccag    180
gcgttccaga ccactcccctc cctccagcac accgccaccc agcgcatcga gaacaacacc    240
tccgtgactc agtctcagac catctccttc aacgagcgca ctactgacac cttcaccact    300
agcgtgacta ctggcttcaa gaccggcacc tccgtgaagt ccaccactaa gttcaaggtg    360
agcgtgggct tcctcgccgc tggcgagctt gagcagtccg tcgaggtcgc tgtcaacttc    420
gagtacaact actccagcac tactacggag actcacagcg tcgagcgtgg ctgggtcatc    480
actcagccca tcattgcgcc gccgaggacc atcgtcgagg ctacgctcct gatctacgct    540
ggcagcgtca acgtccctat cgacctcaac gctaccatcg ttggcgaccc tatcccttgg    600
```

```
ggtgagtggg gtccagctct ctacacctct cactttctcg accgcaacaa cagtgagtgg      660
tcttcgttca tccgccctga ccaactgtct ctggctagtt cggcttaccg cccggctggc      720
cgtacggcga tcttcagtgg acttgcgaac acaaacatcg cgtcgggcct ttactcggtt      780
gtaagaattg acgagcgccc tcttcctggc ttcacaggag agacacgacg ttactacctt      840
ccgccatccc ttgccacacc ggatcagatc ctgtcaacaa acgcactggg aaacaacgtc      900
ccgattatca acccagttcc caatgcacac tgcaagaagg agcactcacc tattatcatc      960
cataagaacc gtgaggagaa gtgtgagaga gactatgacg aagtgtaccc acgacacaac     1020
caggttgaga agtgcgaaca caactacgac gaggagtga                            1059
```

<210> SEQ ID NO 30
<211> LENGTH: 1056
<212> TYPE: DNA
<213> ORGANISM: Artificial Sequence
<220> FEATURE:
<223> OTHER INFORMATION: tic1362
<220> FEATURE:
<223> OTHER INFORMATION: a recombinant polynucleotide encoding a TIC1362

<400> SEQUENCE: 30

```
atggccatca ttgacgacat cgcccaggac gccagcaagg cttgggacgt gaccttcggc       60
cctagcatca ggccgggcac cactcccact gaccgcaccc tcttcaacta ccagctcacc      120
gacatcgtgg ctaaccctag gaccgtgaac ttctccgtgg tcccggagct gatccgcacc      180
gcctcccaga ccatcgagaa cgcctccacc actcagcaat cccagaccct caccttctcc      240
gagaccacta ccgacaccgt gacctccagc gtgacccacg gcttcaagac cggcgtgagc      300
gtgaccgcct ccgccaagtg gaacgccaac atcctcatct ccagcatcga gcagtccttc      360
tccactactg tctccactga gtacaacttc agctctacta gcactcagag caccagtgtc      420
gcccgctctt ggacgatcac gcagccgctc atcgctccgc tcactctaa gatcacggct       480 acgctcttca tctacggcgg tagtttctct gtcccgatgg acctccaagt ccgcatcgtc      540
ggcgagcgca tcaaccctac ctaccctaac gtcggctaca tctactctgc tcgcttccgc      600
cacacgaacg gctctaatta cagggtctg ctttctgctg actttctggc tgcggcgtcg       660
tcagcgtacc gctcggtcgg ttacgacgcg atttggaggg gtacggcgac atcgacagtt      720
tcgcaagggc tgtactcggt tgtaagaatt gatgagacac cgcttccggg gtttgcgggc      780
gagacacggc gttactatct tccggttgtt ccggccgaga acgcatcaaa gattctcaca      840
cccggttcat tgggatcaga gatcatcatt atcaatccaa ttccaaatgc aagttgcaag      900
cgggagcggc caccaattat cctaccacac gaccgtgagg aaacatgcga gcgtcactac      960
gatgagggcc acgttagaca taatggagtt gagaaatgcg agcgacattg tgatgaggag     1020
tactacgatg atgaggagta ctacgatgag gagtga                               1056
```

<210> SEQ ID NO 31
<211> LENGTH: 23
<212> TYPE: PRT
<213> ORGANISM: Artificial Sequence
<220> FEATURE:
<223> OTHER INFORMATION: M0
<220> FEATURE:
<221> NAME/KEY: VARIANT
<222> LOCATION: (7)..(7)
<223> OTHER INFORMATION: is N or T
<220> FEATURE:
<221> NAME/KEY: VARIANT
<222> LOCATION: (14)..(14)
<223> OTHER INFORMATION: is D or A

```
<220> FEATURE:
<221> NAME/KEY: VARIANT
<222> LOCATION: (18)..(18)
<223> OTHER INFORMATION: is I or T
<220> FEATURE:
<221> NAME/KEY: VARIANT
<222> LOCATION: (20)..(20)
<223> OTHER INFORMATION: is R or S
<220> FEATURE:
<221> NAME/KEY: DOMAIN
<222> LOCATION: (13)..(21)
<223> OTHER INFORMATION: core

<400> SEQUENCE: 31

Tyr Gln Leu Thr Asn Val Xaa Val Ser Pro Arg Asn Gln Xaa Phe Gln
1               5                   10                  15

Thr Xaa Pro Xaa Leu Gln His
            20

<210> SEQ ID NO 32
<211> LENGTH: 23
<212> TYPE: PRT
<213> ORGANISM: Artificial Sequence
<220> FEATURE:
<223> OTHER INFORMATION: M0.1
<220> FEATURE:
<223> OTHER INFORMATION: an amino acid sequence corresponding to the
      consensus sequence of SEQ ID NO: 31

<400> SEQUENCE: 32

Tyr Gln Leu Thr Asn Val Asn Val Ser Pro Arg Asn Gln Asp Phe Gln
1               5                   10                  15

Thr Ile Pro Arg Leu Gln His
            20

<210> SEQ ID NO 33
<211> LENGTH: 23
<212> TYPE: PRT
<213> ORGANISM: Artificial Sequence
<220> FEATURE:
<223> OTHER INFORMATION: M0.2
<220> FEATURE:
<223> OTHER INFORMATION: an amino acid sequence corresponding to the
      consensus sequence of SEQ ID NO: 31

<400> SEQUENCE: 33

Tyr Gln Leu Thr Asn Val Asn Val Ser Pro Arg Asn Gln Asp Phe Gln
1               5                   10                  15

Thr Ile Pro Ser Leu Gln His
            20

<210> SEQ ID NO 34
<211> LENGTH: 23
<212> TYPE: PRT
<213> ORGANISM: Artificial Sequence
<220> FEATURE:
<223> OTHER INFORMATION: M0.3
<220> FEATURE:
<223> OTHER INFORMATION: an amino acid sequence corresponding to the
      consensus sequence of SEQ ID NO: 31

<400> SEQUENCE: 34

Tyr Gln Leu Thr Asn Val Asn Val Ser Pro Arg Asn Gln Asp Phe Gln
1               5                   10                  15

Thr Thr Pro Arg Leu Gln His
            20
```

```
<210> SEQ ID NO 35
<211> LENGTH: 23
<212> TYPE: PRT
<213> ORGANISM: Artificial Sequence
<220> FEATURE:
<223> OTHER INFORMATION: M0.4
<220> FEATURE:
<223> OTHER INFORMATION: an amino acid sequence corresponding to the
      consensus sequence of SEQ ID NO: 31

<400> SEQUENCE: 35

Tyr Gln Leu Thr Asn Val Asn Val Ser Pro Arg Asn Gln Asp Phe Gln
1               5                   10                  15

Thr Thr Pro Ser Leu Gln His
            20

<210> SEQ ID NO 36
<211> LENGTH: 23
<212> TYPE: PRT
<213> ORGANISM: Artificial Sequence
<220> FEATURE:
<223> OTHER INFORMATION: M0.5
<220> FEATURE:
<223> OTHER INFORMATION: an amino acid sequence corresponding to the
      consensus sequence of SEQ ID NO: 31

<400> SEQUENCE: 36

Tyr Gln Leu Thr Asn Val Asn Val Ser Pro Arg Asn Gln Ala Phe Gln
1               5                   10                  15

Thr Ile Pro Arg Leu Gln His
            20

<210> SEQ ID NO 37
<211> LENGTH: 23
<212> TYPE: PRT
<213> ORGANISM: Artificial Sequence
<220> FEATURE:
<223> OTHER INFORMATION: M0.6
<220> FEATURE:
<223> OTHER INFORMATION: an amino acid sequence corresponding to the
      consensus sequence of SEQ ID NO: 31

<400> SEQUENCE: 37

Tyr Gln Leu Thr Asn Val Asn Val Ser Pro Arg Asn Gln Ala Phe Gln
1               5                   10                  15

Thr Thr Pro Ser Leu Gln His
            20

<210> SEQ ID NO 38
<211> LENGTH: 23
<212> TYPE: PRT
<213> ORGANISM: Artificial Sequence
<220> FEATURE:
<223> OTHER INFORMATION: M0.7
<220> FEATURE:
<223> OTHER INFORMATION: an amino acid sequence corresponding to the
      consensus sequence of SEQ ID NO: 31

<400> SEQUENCE: 38

Tyr Gln Leu Thr Asn Val Asn Val Ser Pro Arg Asn Gln Ala Phe Gln
1               5                   10                  15

Thr Ile Pro Arg Leu Gln His
            20
```

```
<210> SEQ ID NO 39
<211> LENGTH: 23
<212> TYPE: PRT
<213> ORGANISM: Artificial Sequence
<220> FEATURE:
<223> OTHER INFORMATION: M0.8
<220> FEATURE:
<223> OTHER INFORMATION: an amino acid sequence corresponding to the
      consensus sequence of SEQ ID NO: 31

<400> SEQUENCE: 39

Tyr Gln Leu Thr Asn Val Asn Val Ser Pro Arg Asn Gln Ala Phe Gln
1               5                   10                  15

Thr Thr Pro Ser Leu Gln His
            20

<210> SEQ ID NO 40
<211> LENGTH: 23
<212> TYPE: PRT
<213> ORGANISM: Artificial Sequence
<220> FEATURE:
<223> OTHER INFORMATION: M0.9
<220> FEATURE:
<223> OTHER INFORMATION: an amino acid sequence corresponding to the
      consensus sequence of SEQ ID NO: 31

<400> SEQUENCE: 40

Tyr Gln Leu Thr Asn Val Thr Val Ser Pro Arg Asn Gln Asp Phe Gln
1               5                   10                  15

Thr Ile Pro Arg Leu Gln His
            20

<210> SEQ ID NO 41
<211> LENGTH: 23
<212> TYPE: PRT
<213> ORGANISM: Artificial Sequence
<220> FEATURE:
<223> OTHER INFORMATION: M0.10
<220> FEATURE:
<223> OTHER INFORMATION: an amino acid sequence corresponding to the
      consensus sequence of SEQ ID NO: 31

<400> SEQUENCE: 41

Tyr Gln Leu Thr Asn Val Thr Val Ser Pro Arg Asn Gln Asp Phe Gln
1               5                   10                  15

Thr Thr Pro Ser Leu Gln His
            20

<210> SEQ ID NO 42
<211> LENGTH: 23
<212> TYPE: PRT
<213> ORGANISM: Artificial Sequence
<220> FEATURE:
<223> OTHER INFORMATION: M0.11
<220> FEATURE:
<223> OTHER INFORMATION: an amino acid sequence corresponding to the
      consensus sequence of SEQ ID NO: 31

<400> SEQUENCE: 42

Tyr Gln Leu Thr Asn Val Thr Val Ser Pro Arg Asn Gln Asp Phe Gln
1               5                   10                  15

Thr Ile Pro Arg Leu Gln His
            20
```

```
<210> SEQ ID NO 43
<211> LENGTH: 23
<212> TYPE: PRT
<213> ORGANISM: Artificial Sequence
<220> FEATURE:
<223> OTHER INFORMATION: M0.12
<220> FEATURE:
<223> OTHER INFORMATION: an amino acid sequence corresponding to the
      consensus sequence of SEQ ID NO: 31

<400> SEQUENCE: 43

Tyr Gln Leu Thr Asn Val Thr Val Ser Pro Arg Asn Gln Asp Phe Gln
1               5                   10                  15

Thr Thr Pro Ser Leu Gln His
            20

<210> SEQ ID NO 44
<211> LENGTH: 23
<212> TYPE: PRT
<213> ORGANISM: Artificial Sequence
<220> FEATURE:
<223> OTHER INFORMATION: M0.13
<220> FEATURE:
<223> OTHER INFORMATION: an amino acid sequence corresponding to the
      consensus sequence of SEQ ID NO: 31

<400> SEQUENCE: 44

Tyr Gln Leu Thr Asn Val Thr Val Ser Pro Arg Asn Gln Ala Phe Gln
1               5                   10                  15

Thr Ile Pro Arg Leu Gln His
            20

<210> SEQ ID NO 45
<211> LENGTH: 23
<212> TYPE: PRT
<213> ORGANISM: Artificial Sequence
<220> FEATURE:
<223> OTHER INFORMATION: M0.14
<220> FEATURE:
<223> OTHER INFORMATION: an amino acid sequence corresponding to the
      consensus sequence of SEQ ID NO: 31

<400> SEQUENCE: 45

Tyr Gln Leu Thr Asn Val Thr Val Ser Pro Arg Asn Gln Ala Phe Gln
1               5                   10                  15

Thr Thr Pro Ser Leu Gln His
            20

<210> SEQ ID NO 46
<211> LENGTH: 23
<212> TYPE: PRT
<213> ORGANISM: Artificial Sequence
<220> FEATURE:
<223> OTHER INFORMATION: M0.15
<220> FEATURE:
<223> OTHER INFORMATION: an amino acid sequence corresponding to the
      consensus sequence of SEQ ID NO: 31

<400> SEQUENCE: 46

Tyr Gln Leu Thr Asn Val Thr Val Ser Pro Arg Asn Gln Ala Phe Gln
1               5                   10                  15

Thr Ile Pro Arg Leu Gln His
            20
```

```
<210> SEQ ID NO 47
<211> LENGTH: 23
<212> TYPE: PRT
<213> ORGANISM: Artificial Sequence
<220> FEATURE:
<223> OTHER INFORMATION: M0.16
<220> FEATURE:
<223> OTHER INFORMATION: an amino acid sequence corresponding to the
      consensus sequence of SEQ ID NO: 31

<400> SEQUENCE: 47

Tyr Gln Leu Thr Asn Val Thr Val Ser Pro Arg Asn Gln Ala Phe Gln
1               5                   10                  15

Thr Thr Pro Ser Leu Gln His
            20

<210> SEQ ID NO 48
<211> LENGTH: 43
<212> TYPE: PRT
<213> ORGANISM: Artificial Sequence
<220> FEATURE:
<223> OTHER INFORMATION: M1
<220> FEATURE:
<221> NAME/KEY: VARIANT
<222> LOCATION: (13)..(13)
<223> OTHER INFORMATION: is V or I
<220> FEATURE:
<221> NAME/KEY: VARIANT
<222> LOCATION: (18)..(18)
<223> OTHER INFORMATION: is R or K
<220> FEATURE:
<221> NAME/KEY: DOMAIN
<222> LOCATION: (11)..(20)
<223> OTHER INFORMATION: core

<400> SEQUENCE: 48

Ile Glu Asn Asn Thr Ser Val Thr Gln Ser Gln Thr Xaa Ser Phe Asn
1               5                   10                  15

Glu Xaa Thr Thr Asp Thr Phe Thr Thr Ser Val Thr Thr Gly Phe Lys
            20                  25                  30

Thr Gly Thr Ser Val Lys Ser Thr Thr Lys Phe
        35                  40

<210> SEQ ID NO 49
<211> LENGTH: 43
<212> TYPE: PRT
<213> ORGANISM: Artificial Sequence
<220> FEATURE:
<223> OTHER INFORMATION: M1.1
<220> FEATURE:
<223> OTHER INFORMATION: an amino acid sequence corresponding to the
      consensus sequence of SEQ ID NO: 48

<400> SEQUENCE: 49

Ile Glu Asn Asn Thr Ser Val Thr Gln Ser Gln Thr Val Ser Phe Asn
1               5                   10                  15

Glu Lys Thr Thr Asp Thr Phe Thr Thr Ser Val Thr Thr Gly Phe Lys
            20                  25                  30

Thr Gly Thr Ser Val Lys Ser Thr Thr Lys Phe
        35                  40

<210> SEQ ID NO 50
<211> LENGTH: 43
<212> TYPE: PRT
<213> ORGANISM: Artificial Sequence
<220> FEATURE:
<223> OTHER INFORMATION: M1.2
```

-continued

```
<220> FEATURE:
<223> OTHER INFORMATION: an amino acid sequence corresponding to the
      consensus sequence of SEQ ID NO: 48

<400> SEQUENCE: 50

Ile Glu Asn Asn Thr Ser Val Thr Gln Ser Gln Thr Val Ser Phe Asn
1               5                   10                  15

Glu Arg Thr Thr Asp Thr Phe Thr Thr Ser Val Thr Thr Gly Phe Lys
            20                  25                  30

Thr Gly Thr Ser Val Lys Ser Thr Thr Lys Phe
        35                  40

<210> SEQ ID NO 51
<211> LENGTH: 43
<212> TYPE: PRT
<213> ORGANISM: Artificial Sequence
<220> FEATURE:
<223> OTHER INFORMATION: M1.3
<220> FEATURE:
<223> OTHER INFORMATION: an amino acid sequence corresponding to the
      consensus sequence of SEQ ID NO: 48

<400> SEQUENCE: 51

Ile Glu Asn Asn Thr Ser Val Thr Gln Ser Gln Thr Ile Ser Phe Asn
1               5                   10                  15

Glu Lys Thr Thr Asp Thr Phe Thr Thr Ser Val Thr Thr Gly Phe Lys
            20                  25                  30

Thr Gly Thr Ser Val Lys Ser Thr Thr Lys Phe
        35                  40

<210> SEQ ID NO 52
<211> LENGTH: 43
<212> TYPE: PRT
<213> ORGANISM: Artificial Sequence
<220> FEATURE:
<223> OTHER INFORMATION: M1.4
<220> FEATURE:
<223> OTHER INFORMATION: an amino acid sequence corresponding to the
      consensus sequence of SEQ ID NO: 48

<400> SEQUENCE: 52

Ile Glu Asn Asn Thr Ser Val Thr Gln Ser Gln Thr Ile Ser Phe Asn
1               5                   10                  15

Glu Arg Thr Thr Asp Thr Phe Thr Thr Ser Val Thr Thr Gly Phe Lys
            20                  25                  30

Thr Gly Thr Ser Val Lys Ser Thr Thr Lys Phe
        35                  40

<210> SEQ ID NO 53
<211> LENGTH: 37
<212> TYPE: PRT
<213> ORGANISM: Artificial Sequence
<220> FEATURE:
<223> OTHER INFORMATION: M2
<220> FEATURE:
<221> NAME/KEY: VARIANT
<222> LOCATION: (4)..(4)
<223> OTHER INFORMATION: is S or A
<220> FEATURE:
<221> NAME/KEY: VARIANT
<222> LOCATION: (26)..(26)
<223> OTHER INFORMATION: is V or T
<220> FEATURE:
<221> NAME/KEY: VARIANT
<222> LOCATION: (28)..(28)
<223> OTHER INFORMATION: is T or S
```

```
<400> SEQUENCE: 53

Val Glu Val Xaa Val Asn Phe Glu Tyr Asn Tyr Ser Ser Thr Thr Thr
1               5                   10                  15

Glu Thr His Ser Val Glu Arg Gly Trp Xaa Ile Xaa Gln Pro Ile Ile
            20                  25                  30

Ala Pro Pro Arg Thr
            35

<210> SEQ ID NO 54
<211> LENGTH: 37
<212> TYPE: PRT
<213> ORGANISM: Artificial Sequence
<220> FEATURE:
<223> OTHER INFORMATION: M2.1
<220> FEATURE:
<223> OTHER INFORMATION: an amino acid sequence corresponding to the
      consensus sequence of SEQ ID NO: 53

<400> SEQUENCE: 54

Val Glu Val Ser Val Asn Phe Glu Tyr Asn Tyr Ser Ser Thr Thr Thr
1               5                   10                  15

Glu Thr His Ser Val Glu Arg Gly Trp Val Ile Thr Gln Pro Ile Ile
            20                  25                  30

Ala Pro Pro Arg Thr
            35

<210> SEQ ID NO 55
<211> LENGTH: 37
<212> TYPE: PRT
<213> ORGANISM: Artificial Sequence
<220> FEATURE:
<223> OTHER INFORMATION: M2.2
<220> FEATURE:
<223> OTHER INFORMATION: an amino acid sequence corresponding to the
      consensus sequence of SEQ ID NO: 53

<400> SEQUENCE: 55

Val Glu Val Ser Val Asn Phe Glu Tyr Asn Tyr Ser Ser Thr Thr Thr
1               5                   10                  15

Glu Thr His Ser Val Glu Arg Gly Trp Val Ile Ser Gln Pro Ile Ile
            20                  25                  30

Ala Pro Pro Arg Thr
            35

<210> SEQ ID NO 56
<211> LENGTH: 37
<212> TYPE: PRT
<213> ORGANISM: Artificial Sequence
<220> FEATURE:
<223> OTHER INFORMATION: M2.3
<220> FEATURE:
<223> OTHER INFORMATION: an amino acid sequence corresponding to the
      consensus sequence of SEQ ID NO: 53

<400> SEQUENCE: 56

Val Glu Val Ser Val Asn Phe Glu Tyr Asn Tyr Ser Ser Thr Thr Thr
1               5                   10                  15

Glu Thr His Ser Val Glu Arg Gly Trp Thr Ile Thr Gln Pro Ile Ile
            20                  25                  30

Ala Pro Pro Arg Thr
            35
```

```
<210> SEQ ID NO 57
<211> LENGTH: 37
<212> TYPE: PRT
<213> ORGANISM: Artificial Sequence
<220> FEATURE:
<223> OTHER INFORMATION: M2.4
<220> FEATURE:
<223> OTHER INFORMATION: an amino acid sequence corresponding to the
      consensus sequence of SEQ ID NO: 53

<400> SEQUENCE: 57

Val Glu Val Ser Val Asn Phe Glu Tyr Asn Tyr Ser Ser Thr Thr Thr
1               5                   10                  15

Glu Thr His Ser Val Glu Arg Gly Trp Thr Ile Ser Gln Pro Ile Ile
            20                  25                  30

Ala Pro Pro Arg Thr
        35

<210> SEQ ID NO 58
<211> LENGTH: 37
<212> TYPE: PRT
<213> ORGANISM: Artificial Sequence
<220> FEATURE:
<223> OTHER INFORMATION: M2.5
<220> FEATURE:
<223> OTHER INFORMATION: an amino acid sequence corresponding to the
      consensus sequence of SEQ ID NO: 53

<400> SEQUENCE: 58

Val Glu Val Ala Val Asn Phe Glu Tyr Asn Tyr Ser Ser Thr Thr Thr
1               5                   10                  15

Glu Thr His Ser Val Glu Arg Gly Trp Val Ile Thr Gln Pro Ile Ile
            20                  25                  30

Ala Pro Pro Arg Thr
        35

<210> SEQ ID NO 59
<211> LENGTH: 37
<212> TYPE: PRT
<213> ORGANISM: Artificial Sequence
<220> FEATURE:
<223> OTHER INFORMATION: M2.6
<220> FEATURE:
<223> OTHER INFORMATION: an amino acid sequence corresponding to the
      consensus sequence of SEQ ID NO: 53

<400> SEQUENCE: 59

Val Glu Val Ala Val Asn Phe Glu Tyr Asn Tyr Ser Ser Thr Thr Thr
1               5                   10                  15

Glu Thr His Ser Val Glu Arg Gly Trp Val Ile Ser Gln Pro Ile Ile
            20                  25                  30

Ala Pro Pro Arg Thr
        35

<210> SEQ ID NO 60
<211> LENGTH: 37
<212> TYPE: PRT
<213> ORGANISM: Artificial Sequence
<220> FEATURE:
<223> OTHER INFORMATION: M2.7
<220> FEATURE:
<223> OTHER INFORMATION: an amino acid sequence corresponding to the
      consensus sequence of SEQ ID NO: 53
```

```
<400> SEQUENCE: 60

Val Glu Val Ala Val Asn Phe Glu Tyr Asn Tyr Ser Ser Thr Thr Thr
1               5                   10                  15

Glu Thr His Ser Val Glu Arg Gly Trp Thr Ile Thr Gln Pro Ile Ile
            20                  25                  30

Ala Pro Pro Arg Thr
        35

<210> SEQ ID NO 61
<211> LENGTH: 37
<212> TYPE: PRT
<213> ORGANISM: Artificial Sequence
<220> FEATURE:
<223> OTHER INFORMATION: M2.8
<220> FEATURE:
<223> OTHER INFORMATION: an amino acid sequence corresponding to the
      consensus sequence of SEQ ID NO: 53

<400> SEQUENCE: 61

Val Glu Val Ala Val Asn Phe Glu Tyr Asn Tyr Ser Ser Thr Thr Thr
1               5                   10                  15

Glu Thr His Ser Val Glu Arg Gly Trp Thr Ile Ser Gln Pro Ile Ile
            20                  25                  30

Ala Pro Pro Arg Thr
        35

<210> SEQ ID NO 62
<211> LENGTH: 29
<212> TYPE: PRT
<213> ORGANISM: Artificial Sequence
<220> FEATURE:
<223> OTHER INFORMATION: M3
<220> FEATURE:
<221> NAME/KEY: VARIANT
<222> LOCATION: (13)..(13)
<223> OTHER INFORMATION: is D or N
<220> FEATURE:
<221> NAME/KEY: DOMAIN
<222> LOCATION: (9)..(17)
<223> OTHER INFORMATION: core

<400> SEQUENCE: 62

Val Glu Ala Thr Leu Leu Ile Tyr Ala Gly Ser Val Xaa Val Pro Ile
1               5                   10                  15

Asp Leu Asn Ala Thr Ile Val Gly Asp Pro Ile Pro Trp
            20                  25

<210> SEQ ID NO 63
<211> LENGTH: 29
<212> TYPE: PRT
<213> ORGANISM: Artificial Sequence
<220> FEATURE:
<223> OTHER INFORMATION: M3.1
<220> FEATURE:
<223> OTHER INFORMATION: an amino acid sequence corresponding to the
      consensus sequence of SEQ ID NO: 62

<400> SEQUENCE: 63

Val Glu Ala Thr Leu Leu Ile Tyr Ala Gly Ser Val Asp Val Pro Ile
1               5                   10                  15

Asp Leu Asn Ala Thr Ile Val Gly Asp Pro Ile Pro Trp
            20                  25
```

```
<210> SEQ ID NO 64
<211> LENGTH: 29
<212> TYPE: PRT
<213> ORGANISM: Artificial Sequence
<220> FEATURE:
<223> OTHER INFORMATION: M3.2
<220> FEATURE:
<223> OTHER INFORMATION: an amino acid sequence corresponding to the
      consensus sequence of SEQ ID NO: 62

<400> SEQUENCE: 64

Val Glu Ala Thr Leu Leu Ile Tyr Ala Gly Ser Val Asn Val Pro Ile
1               5                   10                  15

Asp Leu Asn Ala Thr Ile Val Gly Asp Pro Ile Pro Trp
            20                  25

<210> SEQ ID NO 65
<211> LENGTH: 28
<212> TYPE: PRT
<213> ORGANISM: Artificial Sequence
<220> FEATURE:
<223> OTHER INFORMATION: M4
<220> FEATURE:
<221> NAME/KEY: VARIANT
<222> LOCATION: (21)..(21)
<223> OTHER INFORMATION: is P or T
<220> FEATURE:
<221> NAME/KEY: VARIANT
<222> LOCATION: (22)..(22)
<223> OTHER INFORMATION: is D or N
<220> FEATURE:
<221> NAME/KEY: DOMAIN
<222> LOCATION: (17)..(26)
<223> OTHER INFORMATION: core

<400> SEQUENCE: 65

Pro Leu Pro Gly Phe Thr Gly Glu Thr Arg Arg Tyr Tyr Leu Pro Pro
1               5                   10                  15

Ser Leu Ala Thr Xaa Xaa Gln Ile Leu Ser Thr Asn
            20                  25

<210> SEQ ID NO 66
<211> LENGTH: 28
<212> TYPE: PRT
<213> ORGANISM: Artificial Sequence
<220> FEATURE:
<223> OTHER INFORMATION: M4.1
<220> FEATURE:
<223> OTHER INFORMATION: an amino acid sequence corresponding to the
      consensus sequence of SEQ ID NO: 65

<400> SEQUENCE: 66

Pro Leu Pro Gly Phe Thr Gly Glu Thr Arg Arg Tyr Tyr Leu Pro Pro
1               5                   10                  15

Ser Leu Ala Thr Pro Asp Gln Ile Leu Ser Thr Asn
            20                  25

<210> SEQ ID NO 67
<211> LENGTH: 28
<212> TYPE: PRT
<213> ORGANISM: Artificial Sequence
<220> FEATURE:
<223> OTHER INFORMATION: M4.2
<220> FEATURE:
<223> OTHER INFORMATION: an amino acid sequence corresponding to the
      consensus sequence of SEQ ID NO: 65
```

```
<400> SEQUENCE: 67

Pro Leu Pro Gly Phe Thr Gly Glu Thr Arg Arg Tyr Tyr Leu Pro Pro
1               5                   10                  15

Ser Leu Ala Thr Pro Asn Gln Ile Leu Ser Thr Asn
            20                  25

<210> SEQ ID NO 68
<211> LENGTH: 28
<212> TYPE: PRT
<213> ORGANISM: Artificial Sequence
<220> FEATURE:
<223> OTHER INFORMATION: M4.3
<220> FEATURE:
<223> OTHER INFORMATION: an amino acid sequence corresponding to the
      consensus sequence of SEQ ID NO: 65

<400> SEQUENCE: 68

Pro Leu Pro Gly Phe Thr Gly Glu Thr Arg Arg Tyr Tyr Leu Pro Pro
1               5                   10                  15

Ser Leu Ala Thr Thr Asp Gln Ile Leu Ser Thr Asn
            20                  25

<210> SEQ ID NO 69
<211> LENGTH: 28
<212> TYPE: PRT
<213> ORGANISM: Artificial Sequence
<220> FEATURE:
<223> OTHER INFORMATION: M4.4
<220> FEATURE:
<223> OTHER INFORMATION: an amino acid sequence corresponding to the
      consensus sequence of SEQ ID NO: 65

<400> SEQUENCE: 69

Pro Leu Pro Gly Phe Thr Gly Glu Thr Arg Arg Tyr Tyr Leu Pro Pro
1               5                   10                  15

Ser Leu Ala Thr Thr Asn Gln Ile Leu Ser Thr Asn
            20                  25

<210> SEQ ID NO 70
<211> LENGTH: 19
<212> TYPE: PRT
<213> ORGANISM: Artificial Sequence
<220> FEATURE:
<223> OTHER INFORMATION: M1t
<220> FEATURE:
<221> NAME/KEY: VARIANT
<222> LOCATION: (5)..(5)
<223> OTHER INFORMATION: is V or F
<220> FEATURE:
<221> NAME/KEY: VARIANT
<222> LOCATION: (7)..(7)
<223> OTHER INFORMATION: is S or T
<220> FEATURE:
<221> NAME/KEY: VARIANT
<222> LOCATION: (11)..(11)
<223> OTHER INFORMATION: is H or T
<220> FEATURE:
<221> NAME/KEY: VARIANT
<222> LOCATION: (17)..(17)
<223> OTHER INFORMATION: is V or T

<400> SEQUENCE: 70

Thr Thr Asp Thr Xaa Thr Xaa Ser Val Thr Xaa Gly Phe Lys Thr Gly
1               5                   10                  15

Xaa Ser Val
```

```
<210> SEQ ID NO 71
<211> LENGTH: 19
<212> TYPE: PRT
<213> ORGANISM: Artificial Sequence
<220> FEATURE:
<223> OTHER INFORMATION: M1t.1
<220> FEATURE:
<223> OTHER INFORMATION: an amino acid sequence corresponding to the
      consensus sequence of SEQ ID NO: 70

<400> SEQUENCE: 71

Thr Thr Asp Thr Val Thr Ser Ser Val Thr His Gly Phe Lys Thr Gly
1               5                   10                  15

Val Ser Val

<210> SEQ ID NO 72
<211> LENGTH: 19
<212> TYPE: PRT
<213> ORGANISM: Artificial Sequence
<220> FEATURE:
<223> OTHER INFORMATION: M1t.2
<220> FEATURE:
<223> OTHER INFORMATION: an amino acid sequence corresponding to the
      consensus sequence of SEQ ID NO: 70

<400> SEQUENCE: 72

Thr Thr Asp Thr Val Thr Ser Ser Val Thr His Gly Phe Lys Thr Gly
1               5                   10                  15

Thr Ser Val

<210> SEQ ID NO 73
<211> LENGTH: 19
<212> TYPE: PRT
<213> ORGANISM: Artificial Sequence
<220> FEATURE:
<223> OTHER INFORMATION: M1t.3
<220> FEATURE:
<223> OTHER INFORMATION: an amino acid sequence corresponding to the
      consensus sequence of SEQ ID NO: 70

<400> SEQUENCE: 73

Thr Thr Asp Thr Val Thr Ser Ser Val Thr Thr Gly Phe Lys Thr Gly
1               5                   10                  15

Val Ser Val

<210> SEQ ID NO 74
<211> LENGTH: 19
<212> TYPE: PRT
<213> ORGANISM: Artificial Sequence
<220> FEATURE:
<223> OTHER INFORMATION: M1t.4
<220> FEATURE:
<223> OTHER INFORMATION: an amino acid sequence corresponding to the
      consensus sequence of SEQ ID NO: 70

<400> SEQUENCE: 74

Thr Thr Asp Thr Val Thr Ser Ser Val Thr Thr Gly Phe Lys Thr Gly
1               5                   10                  15

Thr Ser Val

<210> SEQ ID NO 75
<211> LENGTH: 19
<212> TYPE: PRT
<213> ORGANISM: Artificial Sequence
<220> FEATURE:
<223> OTHER INFORMATION: M1t.5
```

```
<220> FEATURE:
<223> OTHER INFORMATION: an amino acid sequence corresponding to the
      consensus sequence of SEQ ID NO: 70

<400> SEQUENCE: 75

Thr Thr Asp Thr Val Thr Thr Ser Val Thr His Gly Phe Lys Thr Gly
1               5                   10                  15

Val Ser Val

<210> SEQ ID NO 76
<211> LENGTH: 19
<212> TYPE: PRT
<213> ORGANISM: Artificial Sequence
<220> FEATURE:
<223> OTHER INFORMATION: M1t.6
<220> FEATURE:
<223> OTHER INFORMATION: an amino acid sequence corresponding to the
      consensus sequence of SEQ ID NO: 70

<400> SEQUENCE: 76

Thr Thr Asp Thr Val Thr Thr Ser Val Thr His Gly Phe Lys Thr Gly
1               5                   10                  15

Thr Ser Val

<210> SEQ ID NO 77
<211> LENGTH: 19
<212> TYPE: PRT
<213> ORGANISM: Artificial Sequence
<220> FEATURE:
<223> OTHER INFORMATION: M1t.7
<220> FEATURE:
<223> OTHER INFORMATION: an amino acid sequence corresponding to the
      consensus sequence of SEQ ID NO: 70

<400> SEQUENCE: 77

Thr Thr Asp Thr Val Thr Thr Ser Val Thr Thr Gly Phe Lys Thr Gly
1               5                   10                  15

Val Ser Val

<210> SEQ ID NO 78
<211> LENGTH: 19
<212> TYPE: PRT
<213> ORGANISM: Artificial Sequence
<220> FEATURE:
<223> OTHER INFORMATION: M1t.8
<220> FEATURE:
<223> OTHER INFORMATION: an amino acid sequence corresponding to the
      consensus sequence of SEQ ID NO: 70

<400> SEQUENCE: 78

Thr Thr Asp Thr Val Thr Thr Ser Val Thr Thr Gly Phe Lys Thr Gly
1               5                   10                  15

Thr Ser Val

<210> SEQ ID NO 79
<211> LENGTH: 19
<212> TYPE: PRT
<213> ORGANISM: Artificial Sequence
<220> FEATURE:
<223> OTHER INFORMATION: M1t.9
<220> FEATURE:
<223> OTHER INFORMATION: an amino acid sequence corresponding to the
      consensus sequence of SEQ ID NO: 70
```

-continued

```
<400> SEQUENCE: 79

Thr Thr Asp Thr Phe Thr Ser Ser Val Thr His Gly Phe Lys Thr Gly
1               5                   10                  15

Val Ser Val

<210> SEQ ID NO 80
<211> LENGTH: 19
<212> TYPE: PRT
<213> ORGANISM: Artificial Sequence
<220> FEATURE:
<223> OTHER INFORMATION: M1t.10
<220> FEATURE:
<223> OTHER INFORMATION: an amino acid sequence corresponding to the
      consensus sequence of SEQ ID NO: 70

<400> SEQUENCE: 80

Thr Thr Asp Thr Phe Thr Ser Ser Val Thr His Gly Phe Lys Thr Gly
1               5                   10                  15

Thr Ser Val

<210> SEQ ID NO 81
<211> LENGTH: 19
<212> TYPE: PRT
<213> ORGANISM: Artificial Sequence
<220> FEATURE:
<223> OTHER INFORMATION: M1t.11
<220> FEATURE:
<223> OTHER INFORMATION: an amino acid sequence corresponding to the
      consensus sequence of SEQ ID NO: 70

<400> SEQUENCE: 81

Thr Thr Asp Thr Phe Thr Ser Ser Val Thr Thr Gly Phe Lys Thr Gly
1               5                   10                  15

Val Ser Val

<210> SEQ ID NO 82
<211> LENGTH: 19
<212> TYPE: PRT
<213> ORGANISM: Artificial Sequence
<220> FEATURE:
<223> OTHER INFORMATION: M1t.12
<220> FEATURE:
<223> OTHER INFORMATION: an amino acid sequence corresponding to the
      consensus sequence of SEQ ID NO: 70

<400> SEQUENCE: 82

Thr Thr Asp Thr Phe Thr Ser Ser Val Thr Thr Gly Phe Lys Thr Gly
1               5                   10                  15

Thr Ser Val

<210> SEQ ID NO 83
<211> LENGTH: 19
<212> TYPE: PRT
<213> ORGANISM: Artificial Sequence
<220> FEATURE:
<223> OTHER INFORMATION: M1t.13
<220> FEATURE:
<223> OTHER INFORMATION: an amino acid sequence corresponding to the
      consensus sequence of SEQ ID NO: 70

<400> SEQUENCE: 83

Thr Thr Asp Thr Phe Thr Thr Ser Val Thr His Gly Phe Lys Thr Gly
1               5                   10                  15

Val Ser Val
```

```
<210> SEQ ID NO 84
<211> LENGTH: 19
<212> TYPE: PRT
<213> ORGANISM: Artificial Sequence
<220> FEATURE:
<223> OTHER INFORMATION: M1t.14
<220> FEATURE:
<223> OTHER INFORMATION: an amino acid sequence corresponding to the
      consensus sequence of SEQ ID NO: 70

<400> SEQUENCE: 84

Thr Thr Asp Thr Phe Thr Thr Ser Val Thr His Gly Phe Lys Thr Gly
1               5                   10                  15

Thr Ser Val

<210> SEQ ID NO 85
<211> LENGTH: 19
<212> TYPE: PRT
<213> ORGANISM: Artificial Sequence
<220> FEATURE:
<223> OTHER INFORMATION: M1t.15
<220> FEATURE:
<223> OTHER INFORMATION: an amino acid sequence corresponding to the
      consensus sequence of SEQ ID NO: 70

<400> SEQUENCE: 85

Thr Thr Asp Thr Phe Thr Thr Ser Val Thr Thr Gly Phe Lys Thr Gly
1               5                   10                  15

Val Ser Val

<210> SEQ ID NO 86
<211> LENGTH: 19
<212> TYPE: PRT
<213> ORGANISM: Artificial Sequence
<220> FEATURE:
<223> OTHER INFORMATION: M1t.16
<220> FEATURE:
<223> OTHER INFORMATION: an amino acid sequence corresponding to the
      consensus sequence of SEQ ID NO: 70

<400> SEQUENCE: 86

Thr Thr Asp Thr Phe Thr Thr Ser Val Thr Gly Phe Lys Thr Gly
1               5                   10                  15

Thr Ser Val

<210> SEQ ID NO 87
<211> LENGTH: 16
<212> TYPE: PRT
<213> ORGANISM: Artificial Sequence
<220> FEATURE:
<223> OTHER INFORMATION: M2t
<220> FEATURE:
<221> NAME/KEY: VARIANT
<222> LOCATION: (3)..(3)
<223> OTHER INFORMATION: is E or A
<220> FEATURE:
<221> NAME/KEY: VARIANT
<222> LOCATION: (5)..(5)
<223> OTHER INFORMATION: is G or S
<220> FEATURE:
<221> NAME/KEY: VARIANT
<222> LOCATION: (7)..(7)
<223> OTHER INFORMATION: is V or T
<220> FEATURE:
<221> NAME/KEY: VARIANT
<222> LOCATION: (9)..(9)
<223> OTHER INFORMATION: is T or S
```

```
<220> FEATURE:
<221> NAME/KEY: VARIANT
<222> LOCATION: (12)..(12)
<223> OTHER INFORMATION: is L or I

<400> SEQUENCE: 87

Ser Val Xaa Arg Xaa Trp Xaa Ile Xaa Gln Pro Xaa Ile Ala Pro Pro
1               5                   10                  15

<210> SEQ ID NO 88
<211> LENGTH: 16
<212> TYPE: PRT
<213> ORGANISM: Artificial Sequence
<220> FEATURE:
<223> OTHER INFORMATION: M2t.1
<220> FEATURE:
<223> OTHER INFORMATION: an amino acid sequence corresponding to the
      consensus sequence of SEQ ID NO: 87

<400> SEQUENCE: 88

Ser Val Glu Arg Gly Trp Val Ile Thr Gln Pro Leu Ile Ala Pro Pro
1               5                   10                  15

<210> SEQ ID NO 89
<211> LENGTH: 16
<212> TYPE: PRT
<213> ORGANISM: Artificial Sequence
<220> FEATURE:
<223> OTHER INFORMATION: M2t.2
<220> FEATURE:
<223> OTHER INFORMATION: an amino acid sequence corresponding to the
      consensus sequence of SEQ ID NO: 87

<400> SEQUENCE: 89

Ser Val Glu Arg Gly Trp Val Ile Thr Gln Pro Ile Ile Ala Pro Pro
1               5                   10                  15

<210> SEQ ID NO 90
<211> LENGTH: 16
<212> TYPE: PRT
<213> ORGANISM: Artificial Sequence
<220> FEATURE:
<223> OTHER INFORMATION: M2t.3
<220> FEATURE:
<223> OTHER INFORMATION: an amino acid sequence corresponding to the
      consensus sequence of SEQ ID NO: 87

<400> SEQUENCE: 90

Ser Val Glu Arg Gly Trp Val Ile Ser Gln Pro Leu Ile Ala Pro Pro
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: M2t.4
<220> FEATURE:
<223> OTHER INFORMATION: an amino acid sequence corresponding to the
      consensus sequence of SEQ ID NO: 87

<400> SEQUENCE: 91

Ser Val Glu Arg Gly Trp Val Ile Ser Gln Pro Ile Ile Ala Pro Pro
1               5                   10                  15

<210> SEQ ID NO 92
<211> LENGTH: 16
<212> TYPE: PRT
<213> ORGANISM: Artificial Sequence
```

```
<220> FEATURE:
<223> OTHER INFORMATION: M2t.5
<220> FEATURE:
<223> OTHER INFORMATION: an amino acid sequence corresponding to the
      consensus sequence of SEQ ID NO: 87

<400> SEQUENCE: 92

Ser Val Glu Arg Gly Trp Thr Ile Thr Gln Pro Leu Ile Ala Pro Pro
1               5                   10                  15

<210> SEQ ID NO 93
<211> LENGTH: 16
<212> TYPE: PRT
<213> ORGANISM: Artificial Sequence
<220> FEATURE:
<223> OTHER INFORMATION: M2t.6
<220> FEATURE:
<223> OTHER INFORMATION: an amino acid sequence corresponding to the
      consensus sequence of SEQ ID NO: 87

<400> SEQUENCE: 93

Ser Val Glu Arg Gly Trp Thr Ile Thr Gln Pro Ile Ile Ala Pro Pro
1               5                   10                  15

<210> SEQ ID NO 94
<211> LENGTH: 16
<212> TYPE: PRT
<213> ORGANISM: Artificial Sequence
<220> FEATURE:
<223> OTHER INFORMATION: M2t.7
<220> FEATURE:
<223> OTHER INFORMATION: an amino acid sequence corresponding to the
      consensus sequence of SEQ ID NO: 87

<400> SEQUENCE: 94

Ser Val Glu Arg Gly Trp Thr Ile Ser Gln Pro Leu Ile Ala Pro Pro
1               5                   10                  15

<210> SEQ ID NO 95
<211> LENGTH: 16
<212> TYPE: PRT
<213> ORGANISM: Artificial Sequence
<220> FEATURE:
<223> OTHER INFORMATION: M2t.8
<220> FEATURE:
<223> OTHER INFORMATION: an amino acid sequence corresponding to the
      consensus sequence of SEQ ID NO: 87

<400> SEQUENCE: 95

Ser Val Glu Arg Gly Trp Thr Ile Ser Gln Pro Ile Ile Ala Pro Pro
1               5                   10                  15

<210> SEQ ID NO 96
<211> LENGTH: 16
<212> TYPE: PRT
<213> ORGANISM: Artificial Sequence
<220> FEATURE:
<223> OTHER INFORMATION: M2t.9
<220> FEATURE:
<223> OTHER INFORMATION: an amino acid sequence corresponding to the
      consensus sequence of SEQ ID NO: 87

<400> SEQUENCE: 96

Ser Val Glu Arg Ser Trp Val Ile Thr Gln Pro Leu Ile Ala Pro Pro
1               5                   10                  15
```

```
<210> SEQ ID NO 97
<211> LENGTH: 16
<212> TYPE: PRT
<213> ORGANISM: Artificial Sequence
<220> FEATURE:
<223> OTHER INFORMATION: M2t.10
<220> FEATURE:
<223> OTHER INFORMATION: an amino acid sequence corresponding to the
      consensus sequence of SEQ ID NO: 87

<400> SEQUENCE: 97

Ser Val Glu Arg Ser Trp Val Ile Thr Gln Pro Ile Ile Ala Pro Pro
1               5                   10                  15

<210> SEQ ID NO 98
<211> LENGTH: 16
<212> TYPE: PRT
<213> ORGANISM: Artificial Sequence
<220> FEATURE:
<223> OTHER INFORMATION: M2t.11
<220> FEATURE:
<223> OTHER INFORMATION: an amino acid sequence corresponding to the
      consensus sequence of SEQ ID NO: 87

<400> SEQUENCE: 98

Ser Val Glu Arg Ser Trp Val Ile Ser Gln Pro Leu Ile Ala Pro Pro
1               5                   10                  15

<210> SEQ ID NO 99
<211> LENGTH: 16
<212> TYPE: PRT
<213> ORGANISM: Artificial Sequence
<220> FEATURE:
<223> OTHER INFORMATION: M2t.12
<220> FEATURE:
<223> OTHER INFORMATION: an amino acid sequence corresponding to the
      consensus sequence of SEQ ID NO: 87

<400> SEQUENCE: 99

Ser Val Glu Arg Ser Trp Val Ile Ser Gln Pro Ile Ile Ala Pro Pro
1               5                   10                  15

<210> SEQ ID NO 100
<211> LENGTH: 16
<212> TYPE: PRT
<213> ORGANISM: Artificial Sequence
<220> FEATURE:
<223> OTHER INFORMATION: M2t.13
<220> FEATURE:
<223> OTHER INFORMATION: an amino acid sequence corresponding to the
      consensus sequence of SEQ ID NO: 87

<400> SEQUENCE: 100

Ser Val Glu Arg Ser Trp Thr Ile Thr Gln Pro Leu Ile Ala Pro Pro
1               5                   10                  15

<210> SEQ ID NO 101
<211> LENGTH: 16
<212> TYPE: PRT
<213> ORGANISM: Artificial Sequence
<220> FEATURE:
<223> OTHER INFORMATION: M2t.14
<220> FEATURE:
<223> OTHER INFORMATION: an amino acid sequence corresponding to the
      consensus sequence of SEQ ID NO: 87

<400> SEQUENCE: 101

Ser Val Glu Arg Ser Trp Thr Ile Thr Gln Pro Ile Ile Ala Pro Pro
1               5                   10                  15
```

```
<210> SEQ ID NO 102
<211> LENGTH: 16
<212> TYPE: PRT
<213> ORGANISM: Artificial Sequence
<220> FEATURE:
<223> OTHER INFORMATION: M2t.15
<220> FEATURE:
<223> OTHER INFORMATION: an amino acid sequence corresponding to the
      consensus sequence of SEQ ID NO: 87

<400> SEQUENCE: 102

Ser Val Glu Arg Ser Trp Thr Ile Ser Gln Pro Leu Ile Ala Pro Pro
1               5                   10                  15

<210> SEQ ID NO 103
<211> LENGTH: 16
<212> TYPE: PRT
<213> ORGANISM: Artificial Sequence
<220> FEATURE:
<223> OTHER INFORMATION: M2t.16
<220> FEATURE:
<223> OTHER INFORMATION: an amino acid sequence corresponding to the
      consensus sequence of SEQ ID NO: 87

<400> SEQUENCE: 103

Ser Val Glu Arg Ser Trp Thr Ile Ser Gln Pro Ile Ile Ala Pro Pro
1               5                   10                  15

<210> SEQ ID NO 104
<211> LENGTH: 16
<212> TYPE: PRT
<213> ORGANISM: Artificial Sequence
<220> FEATURE:
<223> OTHER INFORMATION: M2t.17
<220> FEATURE:
<223> OTHER INFORMATION: an amino acid sequence corresponding to the
      consensus sequence of SEQ ID NO: 87

<400> SEQUENCE: 104

Ser Val Ala Arg Gly Trp Val Ile Thr Gln Pro Leu Ile Ala Pro Pro
1               5                   10                  15

<210> SEQ ID NO 105
<211> LENGTH: 16
<212> TYPE: PRT
<213> ORGANISM: Artificial Sequence
<220> FEATURE:
<223> OTHER INFORMATION: M2t.18
<220> FEATURE:
<223> OTHER INFORMATION: an amino acid sequence corresponding to the
      consensus sequence of SEQ ID NO: 87

<400> SEQUENCE: 105

Ser Val Ala Arg Gly Trp Val Ile Thr Gln Pro Ile Ile Ala Pro Pro
1               5                   10                  15

<210> SEQ ID NO 106
<211> LENGTH: 16
<212> TYPE: PRT
<213> ORGANISM: Artificial Sequence
<220> FEATURE:
<223> OTHER INFORMATION: M2t.19
<220> FEATURE:
<223> OTHER INFORMATION: an amino acid sequence corresponding to the
      consensus sequence of SEQ ID NO: 87

<400> SEQUENCE: 106

Ser Val Ala Arg Gly Trp Val Ile Ser Gln Pro Leu Ile Ala Pro Pro
1               5                   10                  15
```

```
<210> SEQ ID NO 107
<211> LENGTH: 16
<212> TYPE: PRT
<213> ORGANISM: Artificial Sequence
<220> FEATURE:
<223> OTHER INFORMATION: M2t.20
<220> FEATURE:
<223> OTHER INFORMATION: an amino acid sequence corresponding to the
      consensus sequence of SEQ ID NO: 87

<400> SEQUENCE: 107

Ser Val Ala Arg Gly Trp Val Ile Ser Gln Pro Ile Ile Ala Pro Pro
1               5                   10                  15

<210> SEQ ID NO 108
<211> LENGTH: 16
<212> TYPE: PRT
<213> ORGANISM: Artificial Sequence
<220> FEATURE:
<223> OTHER INFORMATION: M2t.21
<220> FEATURE:
<223> OTHER INFORMATION: an amino acid sequence corresponding to the
      consensus sequence of SEQ ID NO: 87

<400> SEQUENCE: 108

Ser Val Ala Arg Gly Trp Thr Ile Thr Gln Pro Leu Ile Ala Pro Pro
1               5                   10                  15

<210> SEQ ID NO 109
<211> LENGTH: 16
<212> TYPE: PRT
<213> ORGANISM: Artificial Sequence
<220> FEATURE:
<223> OTHER INFORMATION: M2t.22
<220> FEATURE:
<223> OTHER INFORMATION: an amino acid sequence corresponding to the
      consensus sequence of SEQ ID NO: 87

<400> SEQUENCE: 109

Ser Val Ala Arg Gly Trp Thr Ile Thr Gln Pro Ile Ile Ala Pro Pro
1               5                   10                  15

<210> SEQ ID NO 110
<211> LENGTH: 16
<212> TYPE: PRT
<213> ORGANISM: Artificial Sequence
<220> FEATURE:
<223> OTHER INFORMATION: M2t.23
<220> FEATURE:
<223> OTHER INFORMATION: an amino acid sequence corresponding to the
      consensus sequence of SEQ ID NO: 87

<400> SEQUENCE: 110

Ser Val Ala Arg Gly Trp Thr Ile Ser Gln Pro Leu Ile Ala Pro Pro
1               5                   10                  15

<210> SEQ ID NO 111
<211> LENGTH: 16
<212> TYPE: PRT
<213> ORGANISM: Artificial Sequence
<220> FEATURE:
<223> OTHER INFORMATION: M2t.24
<220> FEATURE:
<223> OTHER INFORMATION: an amino acid sequence corresponding to the
      consensus sequence of SEQ ID NO: 87

<400> SEQUENCE: 111

Ser Val Ala Arg Gly Trp Thr Ile Ser Gln Pro Ile Ile Ala Pro Pro
1               5                   10                  15
```

```
<210> SEQ ID NO 112
<211> LENGTH: 16
<212> TYPE: PRT
<213> ORGANISM: Artificial Sequence
<220> FEATURE:
<223> OTHER INFORMATION: M2t.25
<220> FEATURE:
<223> OTHER INFORMATION: an amino acid sequence corresponding to the
      consensus sequence of SEQ ID NO: 87

<400> SEQUENCE: 112

Ser Val Ala Arg Ser Trp Val Ile Thr Gln Pro Leu Ile Ala Pro Pro
1               5                   10                  15

<210> SEQ ID NO 113
<211> LENGTH: 16
<212> TYPE: PRT
<213> ORGANISM: Artificial Sequence
<220> FEATURE:
<223> OTHER INFORMATION: M2t.26
<220> FEATURE:
<223> OTHER INFORMATION: an amino acid sequence corresponding to the
      consensus sequence of SEQ ID NO: 87

<400> SEQUENCE: 113

Ser Val Ala Arg Ser Trp Val Ile Thr Gln Pro Ile Ile Ala Pro Pro
1               5                   10                  15

<210> SEQ ID NO 114
<211> LENGTH: 16
<212> TYPE: PRT
<213> ORGANISM: Artificial Sequence
<220> FEATURE:
<223> OTHER INFORMATION: M2t.27
<220> FEATURE:
<223> OTHER INFORMATION: an amino acid sequence corresponding to the
      consensus sequence of SEQ ID NO: 87

<400> SEQUENCE: 114

Ser Val Ala Arg Ser Trp Val Ile Ser Gln Pro Leu Ile Ala Pro Pro
1               5                   10                  15

<210> SEQ ID NO 115
<211> LENGTH: 16
<212> TYPE: PRT
<213> ORGANISM: Artificial Sequence
<220> FEATURE:
<223> OTHER INFORMATION: M2t.28
<220> FEATURE:
<223> OTHER INFORMATION: an amino acid sequence corresponding to the
      consensus sequence of SEQ ID NO: 87

<400> SEQUENCE: 115

Ser Val Ala Arg Ser Trp Val Ile Ser Gln Pro Ile Ile Ala Pro Pro
1               5                   10                  15

<210> SEQ ID NO 116
<211> LENGTH: 16
<212> TYPE: PRT
<213> ORGANISM: Artificial Sequence
<220> FEATURE:
<223> OTHER INFORMATION: M2t.29
<220> FEATURE:
<223> OTHER INFORMATION: an amino acid sequence corresponding to the
      consensus sequence of SEQ ID NO: 87

<400> SEQUENCE: 116

Ser Val Ala Arg Ser Trp Thr Ile Thr Gln Pro Leu Ile Ala Pro Pro
1               5                   10                  15
```

```
<210> SEQ ID NO 117
<211> LENGTH: 16
<212> TYPE: PRT
<213> ORGANISM: Artificial Sequence
<220> FEATURE:
<223> OTHER INFORMATION: M2t.30
<220> FEATURE:
<223> OTHER INFORMATION: an amino acid sequence corresponding to the
      consensus sequence of SEQ ID NO: 87

<400> SEQUENCE: 117

Ser Val Ala Arg Ser Trp Thr Ile Thr Gln Pro Ile Ile Ala Pro Pro
1               5                   10                  15

<210> SEQ ID NO 118
<211> LENGTH: 16
<212> TYPE: PRT
<213> ORGANISM: Artificial Sequence
<220> FEATURE:
<223> OTHER INFORMATION: M2t.31
<220> FEATURE:
<223> OTHER INFORMATION: an amino acid sequence corresponding to the
      consensus sequence of SEQ ID NO: 87

<400> SEQUENCE: 118

Ser Val Ala Arg Ser Trp Thr Ile Ser Gln Pro Leu Ile Ala Pro Pro
1               5                   10                  15

<210> SEQ ID NO 119
<211> LENGTH: 16
<212> TYPE: PRT
<213> ORGANISM: Artificial Sequence
<220> FEATURE:
<223> OTHER INFORMATION: M2t.32
<220> FEATURE:
<223> OTHER INFORMATION: an amino acid sequence corresponding to the
      consensus sequence of SEQ ID NO: 87

<400> SEQUENCE: 119

Ser Val Ala Arg Ser Trp Thr Ile Ser Gln Pro Ile Ile Ala Pro Pro
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: M4t
<220> FEATURE:
<221> NAME/KEY: VARIANT
<222> LOCATION: (6)..(6)
<223> OTHER INFORMATION: is A or T

<400> SEQUENCE: 120

Pro Leu Pro Gly Phe Xaa Gly Glu Thr Arg Arg Tyr Tyr Leu Pro
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: M4t.1
<220> FEATURE:
<223> OTHER INFORMATION: an amino acid sequence corresponding to the
      consensus sequence of SEQ ID NO: 120

<400> SEQUENCE: 121

Pro Leu Pro Gly Phe Ala Gly Glu Thr Arg Arg Tyr Tyr Leu Pro
1               5                   10                  15
```

```
<210> SEQ ID NO 122
<211> LENGTH: 15
<212> TYPE: PRT
<213> ORGANISM: Artificial Sequence
<220> FEATURE:
<223> OTHER INFORMATION: M4t.2
<220> FEATURE:
<223> OTHER INFORMATION: an amino acid sequence corresponding to the
      consensus sequence of SEQ ID NO: 120
<220> FEATURE:
<221> NAME/KEY: DOMAIN
<222> LOCATION: (3)..(10)
<223> OTHER INFORMATION: core

<400> SEQUENCE: 122

Pro Leu Pro Gly Phe Thr Gly Glu Thr Arg Arg Tyr Tyr Leu Pro
1               5                   10                  15

<210> SEQ ID NO 123
<211> LENGTH: 311
<212> TYPE: PRT
<213> ORGANISM: Artificial Sequence
<220> FEATURE:
<223> OTHER INFORMATION: TIC1497.34225
<220> FEATURE:
<223> OTHER INFORMATION: pesticidal TIC1497 fragment; amino acid
      translation of NT positions 1 through 933 of SEQ ID NO: 5.

<400> SEQUENCE: 123

Ala Ile Ile Asn Gln Ser Ser Leu Asn Ser Arg Ile His Asp Leu Leu
1               5                   10                  15

Glu Asp Ser Arg Glu Ala Phe Asp Ile Phe Tyr Arg Asp Arg Pro Gly
                20                  25                  30

Gly Phe Asn Gly Arg Ile Pro Gly Arg Glu Gln Leu Asp Asn Tyr Gln
            35                  40                  45

Leu Thr Asn Val Asn Val Ser Pro Arg Asn Gln Asp Phe Gln Thr Ile
        50                  55                  60

Pro Arg Leu Gln His Thr Ala Thr Gln Val Ile Glu Asn Asn Thr Ser
65                  70                  75                  80

Val Thr Gln Ser Gln Thr Val Ser Phe Asn Glu Arg Thr Thr Asp Thr
                85                  90                  95

Phe Thr Thr Ser Val Thr Thr Gly Phe Lys Thr Gly Thr Ser Val Lys
            100                 105                 110

Ser Thr Thr Lys Phe Lys Ile Ser Val Gly Phe Leu Ala Ala Gly Glu
        115                 120                 125

Leu Glu Gln Ser Val Glu Val Ala Val Asn Phe Glu Tyr Asn Tyr Ser
    130                 135                 140

Ser Thr Thr Thr Glu Thr His Ser Val Glu Arg Gly Trp Val Ile Thr
145                 150                 155                 160

Gln Pro Ile Ile Ala Pro Pro Arg Thr Arg Val Glu Ala Thr Leu Leu
                165                 170                 175

Ile Tyr Ala Gly Ser Val Asp Val Pro Ile Asp Leu Asn Ala Thr Ile
            180                 185                 190

Val Gly Asp Pro Ile Pro Trp Gln Asp Trp Gly Pro Ser Val Tyr Thr
        195                 200                 205

Ala Ser Phe Leu Asp Gly Asn Asn Leu Gly Trp Ser Gly Phe Ile Arg
    210                 215                 220

Pro Asp Glu Leu Ser Leu Ala Ser Ser Ala Tyr Arg Pro Val Gly Arg
225                 230                 235                 240

Thr Ala Ile Phe Ser Gly Leu Ala Thr Thr Asn Val Ala Ser Gly Leu
                245                 250                 255
```

```
Tyr Ser Ile Val Arg Ile Asp Glu Arg Pro Leu Pro Gly Phe Thr Gly
            260                 265                 270

Glu Thr Arg Arg Tyr Tyr Leu Pro Pro Ser Leu Ala Thr Pro Asp Gln
            275                 280                 285

Ile Leu Ser Thr Asn Thr Phe Gly Asn Asn Val Pro Ile Ile Asn Pro
            290                 295                 300

Val Pro Asn Ala His Cys Lys
305                 310

<210> SEQ ID NO 124
<211> LENGTH: 295
<212> TYPE: PRT
<213> ORGANISM: Artificial Sequence
<220> FEATURE:
<223> OTHER INFORMATION: TIC1497.32557
<220> FEATURE:
<223> OTHER INFORMATION: pesticidal TIC1497 fragment; amino acid
      translation of NT positions 1 through 885 of SEQ ID NO: 5.

<400> SEQUENCE: 124

Ala Ile Ile Asn Gln Ser Ser Leu Asn Ser Arg Ile His Asp Leu Leu
1               5                   10                  15

Glu Asp Ser Arg Glu Ala Phe Asp Ile Phe Tyr Arg Asp Arg Pro Gly
            20                  25                  30

Gly Phe Asn Gly Arg Ile Pro Gly Arg Glu Gln Leu Asp Asn Tyr Gln
            35                  40                  45

Leu Thr Asn Val Asn Val Ser Pro Arg Asn Gln Asp Phe Gln Thr Ile
        50                  55                  60

Pro Arg Leu Gln His Thr Ala Thr Gln Val Ile Glu Asn Asn Thr Ser
65                  70                  75                  80

Val Thr Gln Ser Gln Thr Val Ser Phe Asn Glu Arg Thr Thr Asp Thr
            85                  90                  95

Phe Thr Thr Ser Val Thr Thr Gly Phe Lys Thr Gly Thr Ser Val Lys
            100                 105                 110

Ser Thr Thr Lys Phe Lys Ile Ser Val Gly Phe Leu Ala Ala Gly Glu
            115                 120                 125

Leu Glu Gln Ser Val Glu Val Ala Val Asn Phe Glu Tyr Asn Tyr Ser
        130                 135                 140

Ser Thr Thr Thr Glu Thr His Ser Val Glu Arg Gly Trp Val Ile Thr
145                 150                 155                 160

Gln Pro Ile Ile Ala Pro Pro Arg Thr Arg Val Glu Ala Thr Leu Leu
            165                 170                 175

Ile Tyr Ala Gly Ser Val Asp Val Pro Ile Asp Leu Asn Ala Thr Ile
            180                 185                 190

Val Gly Asp Pro Ile Pro Trp Gln Asp Trp Gly Pro Ser Val Tyr Thr
            195                 200                 205

Ala Ser Phe Leu Asp Gly Asn Asn Leu Gly Trp Ser Gly Phe Ile Arg
        210                 215                 220

Pro Asp Glu Leu Ser Leu Ala Ser Ala Tyr Arg Pro Val Gly Arg
225                 230                 235                 240

Thr Ala Ile Phe Ser Gly Leu Ala Thr Thr Asn Val Ala Ser Gly Leu
            245                 250                 255

Tyr Ser Ile Val Arg Ile Asp Glu Arg Pro Leu Pro Gly Phe Thr Gly
            260                 265                 270
```

```
Glu Thr Arg Arg Tyr Tyr Leu Pro Pro Ser Leu Ala Thr Pro Asp Gln
            275                 280                 285

Ile Leu Ser Thr Asn Thr Phe
        290                 295

<210> SEQ ID NO 125
<211> LENGTH: 313
<212> TYPE: PRT
<213> ORGANISM: Artificial Sequence
<220> FEATURE:
<223> OTHER INFORMATION: TIC1497.34485
<220> FEATURE:
<223> OTHER INFORMATION: pesticidal TIC1497 fragment; amino acid
      translation of NT positions 1 through 939 of SEQ ID NO: 5.

<400> SEQUENCE: 125

Ala Ile Ile Asn Gln Ser Ser Leu Asn Ser Arg Ile His Asp Leu Leu
1               5                   10                  15

Glu Asp Ser Arg Glu Ala Phe Asp Ile Phe Tyr Arg Asp Arg Pro Gly
            20                  25                  30

Gly Phe Asn Gly Arg Ile Pro Gly Arg Glu Gln Leu Asp Asn Tyr Gln
        35                  40                  45

Leu Thr Asn Val Asn Val Ser Pro Arg Asn Gln Asp Phe Gln Thr Ile
    50                  55                  60

Pro Arg Leu Gln His Thr Ala Thr Gln Val Ile Glu Asn Asn Thr Ser
65                  70                  75                  80

Val Thr Gln Ser Gln Thr Val Ser Phe Asn Glu Arg Thr Thr Asp Thr
                85                  90                  95

Phe Thr Thr Ser Val Thr Thr Gly Phe Lys Thr Gly Thr Ser Val Lys
            100                 105                 110

Ser Thr Thr Lys Phe Lys Ile Ser Val Gly Phe Leu Ala Ala Gly Glu
        115                 120                 125

Leu Glu Gln Ser Val Glu Val Ala Val Asn Phe Glu Tyr Asn Tyr Ser
    130                 135                 140

Ser Thr Thr Thr Glu Thr His Ser Val Glu Arg Gly Trp Val Ile Thr
145                 150                 155                 160

Gln Pro Ile Ile Ala Pro Pro Arg Thr Arg Val Glu Ala Thr Leu Leu
                165                 170                 175

Ile Tyr Ala Gly Ser Val Asp Val Pro Ile Asp Leu Asn Ala Thr Ile
            180                 185                 190

Val Gly Asp Pro Ile Pro Trp Gln Asp Trp Gly Pro Ser Val Tyr Thr
        195                 200                 205

Ala Ser Phe Leu Asp Gly Asn Asn Leu Gly Trp Ser Gly Phe Ile Arg
    210                 215                 220

Pro Asp Glu Leu Ser Leu Ala Ser Ser Ala Tyr Arg Pro Val Gly Arg
225                 230                 235                 240

Thr Ala Ile Phe Ser Gly Leu Ala Thr Thr Asn Val Ala Ser Gly Leu
                245                 250                 255

Tyr Ser Ile Val Arg Ile Asp Glu Arg Pro Leu Pro Gly Phe Thr Gly
            260                 265                 270

Glu Thr Arg Arg Tyr Tyr Leu Pro Pro Ser Leu Ala Thr Pro Asp Gln
        275                 280                 285

Ile Leu Ser Thr Asn Thr Phe Gly Asn Asn Val Pro Ile Ile Asn Pro
    290                 295                 300

Val Pro Asn Ala His Cys Lys Lys Glu
305                 310
```

<210> SEQ ID NO 126
<211> LENGTH: 294
<212> TYPE: PRT
<213> ORGANISM: Artificial Sequence
<220> FEATURE:
<223> OTHER INFORMATION: TIC1497.32411
<220> FEATURE:
<223> OTHER INFORMATION: pesticidal TIC1497 fragment; amino acid
      translation of NT positions 1 through 882 of SEQ ID NO: 5.

<400> SEQUENCE: 126

Ala Ile Ile Asn Gln Ser Ser Leu Asn Ser Arg Ile His Asp Leu Leu
1               5                   10                  15

Glu Asp Ser Arg Glu Ala Phe Asp Ile Phe Tyr Arg Asp Arg Pro Gly
            20                  25                  30

Gly Phe Asn Gly Arg Ile Pro Gly Arg Glu Gln Leu Asp Asn Tyr Gln
        35                  40                  45

Leu Thr Asn Val Asn Val Ser Pro Arg Asn Gln Asp Phe Gln Thr Ile
50                  55                  60

Pro Arg Leu Gln His Thr Ala Thr Gln Val Ile Glu Asn Asn Thr Ser
65                  70                  75                  80

Val Thr Gln Ser Gln Thr Val Ser Phe Asn Glu Arg Thr Thr Asp Thr
                85                  90                  95

Phe Thr Thr Ser Val Thr Thr Gly Phe Lys Thr Gly Thr Ser Val Lys
            100                 105                 110

Ser Thr Thr Lys Phe Lys Ile Ser Val Gly Phe Leu Ala Ala Gly Glu
        115                 120                 125

Leu Glu Gln Ser Val Glu Val Ala Val Asn Phe Glu Tyr Asn Tyr Ser
130                 135                 140

Ser Thr Thr Thr Glu Thr His Ser Val Glu Arg Gly Trp Val Ile Thr
145                 150                 155                 160

Gln Pro Ile Ile Ala Pro Pro Arg Thr Arg Val Glu Ala Thr Leu Leu
                165                 170                 175

Ile Tyr Ala Gly Ser Val Asp Val Pro Ile Asp Leu Asn Ala Thr Ile
            180                 185                 190

Val Gly Asp Pro Ile Pro Trp Gln Asp Trp Gly Pro Ser Val Tyr Thr
        195                 200                 205

Ala Ser Phe Leu Asp Gly Asn Asn Leu Gly Trp Ser Gly Phe Ile Arg
210                 215                 220

Pro Asp Glu Leu Ser Leu Ala Ser Ser Ala Tyr Arg Pro Val Gly Arg
225                 230                 235                 240

Thr Ala Ile Phe Ser Gly Leu Ala Thr Thr Asn Val Ala Ser Gly Leu
                245                 250                 255

Tyr Ser Ile Val Arg Ile Asp Glu Arg Pro Leu Pro Gly Phe Thr Gly
            260                 265                 270

Glu Thr Arg Arg Tyr Tyr Leu Pro Pro Ser Leu Ala Thr Pro Asp Gln
        275                 280                 285

Ile Leu Ser Thr Asn Thr
    290

<210> SEQ ID NO 127
<211> LENGTH: 29
<212> TYPE: DNA
<213> ORGANISM: Artificial Sequence
<220> FEATURE:
<223> OTHER INFORMATION: tic1415 forward primer

```
<220> FEATURE:
<223> OTHER INFORMATION: an oligonucleotide primer for hybridizing to
      the (-) strand of the 5 prime end of DNA corresponding to
      positions 1..29 of SEQ ID NO: 3 (tic1415).

<400> SEQUENCE: 127
atggcaatta taaatcaatc atcactaaa                                            29

<210> SEQ ID NO 128
<211> LENGTH: 31
<212> TYPE: DNA
<213> ORGANISM: Artificial Sequence
<220> FEATURE:
<223> OTHER INFORMATION: tic1415 reverse primer
<220> FEATURE:
<223> OTHER INFORMATION: an oligonucleotide primer for hybridizing to
      the (+) strand of the 3 prime end of DNA corresponding to
      positions 1131..1161 of SEQ ID NO: 3 (tic1415).

<400> SEQUENCE: 128
ttattcttca tcataattgt gttcgcactt c                                         31

<210> SEQ ID NO 129
<211> LENGTH: 40
<212> TYPE: DNA
<213> ORGANISM: Artificial Sequence
<220> FEATURE:
<223> OTHER INFORMATION: tic1414 forward primer
<220> FEATURE:
<223> OTHER INFORMATION: an oligonucleotide primer for hybridizing to
      the (-) strand of the 5 prime end of DNA corresponding to
      positions 1..40 of SEQ ID NO: 11 (tic1414).

<400> SEQUENCE: 129
atggcaatta taaatcaatc atcactaaat tcaagaatac                                40

<210> SEQ ID NO 130
<211> LENGTH: 42
<212> TYPE: DNA
<213> ORGANISM: Artificial Sequence
<220> FEATURE:
<223> OTHER INFORMATION: tic1414 reverse primer
<220> FEATURE:
<223> OTHER INFORMATION: an oligonucleotide primer for hybridizing to
      the (+) strand of the 3 prime end of DNA corresponding to
      positions 1015..1056 of SEQ ID NO: 11 (tic1414).

<400> SEQUENCE: 130
ttattcttca tcataattgt gttcgtactt ctctacttga tc                             42

<210> SEQ ID NO 131
<211> LENGTH: 35
<212> TYPE: DNA
<213> ORGANISM: Artificial Sequence
<220> FEATURE:
<223> OTHER INFORMATION: tic1422 forward primer
<220> FEATURE:
<223> OTHER INFORMATION: an oligonucleotide primer for hybridizing to
      the (-) strand of the 5 prime end of DNA corresponding to
      positions 1..35 of SEQ ID NO: 17 (tic1422).

<400> SEQUENCE: 131
atggcaatta taaatcaatc atcactaaat tcaag                                     35

<210> SEQ ID NO 132
<211> LENGTH: 39
<212> TYPE: DNA
<213> ORGANISM: Artificial Sequence
```

```
<220> FEATURE:
<223> OTHER INFORMATION: tic1422 reverse primer
<220> FEATURE:
<223> OTHER INFORMATION: an oligonucleotide primer for hybridizing to
      the (+) strand of the 3 prime end of DNA corresponding to
      positions 1021..1059 of SEQ ID NO: 17 (tic1422).

<400> SEQUENCE: 132
ttattcttca tcataattgt gttcgcactt ctctacttg                          39

<210> SEQ ID NO 133
<211> LENGTH: 28
<212> TYPE: DNA
<213> ORGANISM: Artificial Sequence
<220> FEATURE:
<223> OTHER INFORMATION: tic1362 forward primer
<220> FEATURE:
<223> OTHER INFORMATION: an oligonucleotide primer for hybridizing to
      the (-) strand of the 5 prime end of DNA corresponding to
      positions 1..28 of SEQ ID NO: 25 (tic1362).

<400> SEQUENCE: 133
atggcaatta ttgatgatat tgcacaag                                     28

<210> SEQ ID NO 134
<211> LENGTH: 32
<212> TYPE: DNA
<213> ORGANISM: Artificial Sequence
<220> FEATURE:
<223> OTHER INFORMATION: tic1362 reverse primer
<220> FEATURE:
<223> OTHER INFORMATION: an oligonucleotide primer for hybridizing to
      the (+) strand of the 3 prime end of DNA corresponding to
      positions 1025..1056 of SEQ ID NO: 25 (tic1362).

<400> SEQUENCE: 134
ttattcttca tcatagtatt cttcatcatc at                                32
```

What is claimed is:

1. A recombinant nucleic acid molecule comprising a heterologous promoter operably linked to a polynucleotide segment encoding an insect inhibitory protein, wherein said polynucleotide segment comprises at least 80% nucleic acid sequence identity to SEQ ID NO: 27, and further comprises sequences corresponding to motifs M0, M1, M2, M3, M4, and M5, and wherein said insect inhibitory protein exhibits insect inhibitory activity against a Hemipteran or Lepidopteran pest species.

2. The recombinant nucleic acid molecule of claim 1, wherein said polynucleotide segment comprises a polynucleotide sequence having at least 90% identity to SEQ ID NO: 27.

3. The recombinant nucleic acid molecule of claim 1, wherein said polynucleotide segment comprises a polynucleotide sequence having at least 95% identity to SEQ ID NO: 27.

4. An insect inhibitory composition comprising the recombinant nucleic acid molecule of claim 1.

5. The insect inhibitory composition of claim 4, further comprising at least one other pesticidal agent, wherein said pesticidal agent is structurally different from said insect inhibitory protein, wherein said pesticidal agent is selected from the group consisting of an insect inhibitory protein, an insect inhibitory dsRNA molecule, and an ancillary protein.

6. The insect inhibitory composition of claim 5, wherein said pesticidal agent is selected from the group consisting of a TIC807 protein, a TIC853 protein, a Cry51Aa1 protein, and a AXMI-171 protein.

7. A method of controlling a Lepidopteran or Hemipteran species pest, said method comprising contacting said pest with an insect inhibitory amount of the insect inhibitory protein encoded by the recombinant nucleic acid of claim 1.

8. The method of claim 7, wherein said Lepidopteran or Hemipteran species pest is in a crop field.

9. A host cell comprising the recombinant nucleic acid molecule of claim 1, wherein the host cell is selected from the group consisting of a bacterial cell and a plant cell.

10. The host cell of claim 9, wherein said bacterial host cell is from a genus of bacteria selected from the group consisting of: *Bacillus, Escherichia, Salmonella, Agrobacterium, Pseudomonas*, and *Rhizobium*.

11. The host cell of claim 9, wherein said plant host cell is a cell of a plant selected from the group consisting of alfalfa, banana, barley, bean, broccoli, cabbage, *brassica*, carrot, cassava, castor, cauliflower, celery, chickpea, Chinese cabbage, coconut, coffee, corn, clover, cotton, cucumber, Douglas fir, eggplant, *eucalyptus*, flax, garlic, grape, hops, leek, lettuce, Loblolly pine, millet, melon, oat, olive, onion, palm, pasture grass, pea, peanut, pepper, pigeonpea, potato, poplar, pumpkin, *Radiata* pine, radish, rapeseed, rice, rye, safflower, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and wheat.

12. The host cell of claim 9, wherein said plant host cell is from a plant part selected from the group consisting of a seed, a boll, a leaf, a flower, a stem, and a root.

13. The host cell of claim 9, wherein said host cell further comprises an herbicide tolerance marker.

14. The recombinant nucleic acid molecule of claim 1, wherein the recombinant nucleic acid molecule:
  (a) further comprises a sequence that functions to express said protein in a plant; or
  (b) is expressed in a plant cell to produce an insect inhibitory amount of said protein.

15. A plant comprising a recombinant nucleic acid molecule comprising a heterologous promoter operably linked to a polynucleotide segment encoding an insect inhibitory protein, wherein said polynucleotide segment comprises at least 80% nucleic acid sequence identity to SEQ ID NO:27, and further comprises sequences corresponding to motifs M0, M1, M2, M3, M4, and M5, and wherein said insect inhibitory protein exhibits insect inhibitory activity against a Hemipteran or Lepidopteran pest species.

16. A seed from the plant of claim 15, wherein the seed comprises said recombinant nucleic acid molecule.

17. A method of producing seed comprising the recombinant nucleic acid molecule of claim 1, the method comprising:
  (a) planting at least one seed that comprises the recombinant nucleic acid molecule of claim 1;
  (b) growing at least one plant from said at least one seed;
  (c) harvesting seed from said at least one plant, wherein said harvested seed comprises said recombinant nucleic acid molecule.

18. A plant resistant to insect infestation, wherein the cells of the plant comprise an insecticidally effective amount of an insect inhibitory protein wherein said amino acid sequence is encoded by a polynucleotide comprising at least 80% nucleic acid sequence identity to SEQ ID NO: 27, and further comprises sequences corresponding to motifs M0, M1, M2, M3, M4, and M5, and wherein said insect inhibitory protein exhibits insect inhibitory activity against a Hemipteran or Lepidopteran pest species.

19. The recombinant nucleic acid molecule of claim 18, wherein said polynucleotide segment comprises a polynucleotide sequence having at least 90% identity to SEQ ID NO: 27.

20. The recombinant nucleic acid molecule of claim 18, wherein said polynucleotide segment comprises a polynucleotide sequence having at least 95% identity to SEQ ID NO: 27.

* * * * *